United States Patent
Zhang

(10) Patent No.: US 12,168,678 B2
(45) Date of Patent: *Dec. 17, 2024

(54) HEME SEQUESTING PEPTIDES AND USES THEREFOR

(71) Applicant: Board of Regents, The University of Texas System, Austin, TX (US)

(72) Inventor: Li Zhang, Plano, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/743,835

(22) Filed: May 13, 2022

(65) Prior Publication Data

US 2022/0396601 A1 Dec. 15, 2022

Related U.S. Application Data

(63) Continuation of application No. 16/827,015, filed on Mar. 23, 2020, now Pat. No. 11,358,991.

(60) Provisional application No. 62/821,823, filed on Mar. 21, 2019.

(51) Int. Cl.
| | | |
|---|---|---|
| A61K 38/16 | (2006.01) | |
| A61K 45/06 | (2006.01) | |
| A61P 31/10 | (2006.01) | |
| A61P 35/00 | (2006.01) | |
| C07K 14/24 | (2006.01) | |
| A61K 38/00 | (2006.01) | |

(52) U.S. Cl.
CPC ............ *C07K 14/24* (2013.01); *A61K 38/164* (2013.01); *A61K 45/06* (2013.01); *A61P 31/10* (2018.01); *A61P 35/00* (2018.01); *A61K 38/00* (2013.01)

(58) Field of Classification Search
None
See application file for complete search history.

(56) References Cited

U.S. PATENT DOCUMENTS 11,358,991 B2 * 6/2022 Zhang .................... C07K 14/21

OTHER PUBLICATIONS

Lowe, Derek; "Not alphafold's fault." blog "In the pipeline," entry of Sep. 7, 2022.*
Wandersman, Cecile and Delepelaire, Philippe; "Bacterial iron sources: from siderophores to hemophores." Annu. Rev. Microbiol. (2004) 58 p. 611-647.*
Theocharis, Achilleas D. et al; "Proteoglycans in health and disease: novel roles for proteoglycans in malignancy and their pharacological targeting." FEBS J. (2010)277 p. 3904-3923.*
NCBI protein database for decorin, Accession No. AAA53201 (2016).*
Hooda, Jagmohan et al; "Enhanced heme function and mitochondrial respiration promotethe progression of lung cancer cells." PLoS One (2013) 8(5) e6342.*
Gao, Cuicui et al; "Cancer stem cells in small cell lung cancer cell line h446: higher dependency on oxadative phosphorylation and mitochondrial substrate level phosphorylation than non-stem cancer cells." PLoS One (2016) 11(5) e0154576.*
Bairwa, G., Jung, W.H. & Kronstad, J.W. "Iron acquisition in fungal pathogens of humans," Metallomics 9, 215-227 (2017).
Deniau, C. et al. "Thermodynamics of heme binding to the HasA(SM) hemophore: effect of mutations at three key residues for heme uptake," Biochemistry 42, 10627-10633 (2003).
D'Souza, A., Wu, X., Yeow, E.K.L. & Bhattacharjya, S. "Designed Heme-Cage beta-Sheet Miniproteins," Angew Chem Int Ed Engl 56, 5904-5908 (2017).
D'Souza et al., "Designed multi-strantded heme binding beta-sheet peptides in membrane", Chem. Sci., 7, p. 2563-2571, (2016).
Gibney, B.R., Mulholland, S.E., Rabanal, F. & Dutton, P.L. "Ferredoxin and ferredoxin-heme maquettes," Proc Natl Acad Sci U S A 93, 15041-15046 (1996).
Guo et al., "Protein tolerance to random amino acid changes", PNAS, 101(25), 9205-9210, (2004).
Hosogaya, et al., "The heme binding protein dap1 links iron homeostasis to azole resistance via the p450 protein erg11 in candida glabrata", FEMS Yeast Res., 13, p. 411-421, (2013).
Huang, W. & Wilks, A. "Extracellular Heme Uptake and the Challenge of Bacterial Cell Membranes," Annu Rev Biochem 86, 799-823 (2017).
Kumar R, Lovell S, Matsumura H, Battaile KP, Moenne-Loccoz P, Rivera M. "The hemophore HasA from *Yersinia pestis* (HasAyp) coordinates hemin with a single residue, Tyr75, and with minimal conformational change," Biochemistry 2013;52:2705-7.
Kumar et al., "Replacing arginine 33 for alanine in the hemophore hasa from pseudomonas aeruginosa causes closure of the h32 loop in the apo-protein", Biochemistry, 55(18), p. 2622-2631, 2016.
Kuznets, G. et al. "A relay network of extracellular heme-binding proteins drives *C. albicans* iron acquisition from hemoglobin," PLoS pathogens 10, e1004407 (2014).
Rojas, N.R. et al. "De novo heme proteins from designed combinatorial libraries," Protein Sci 6, 2512-2524 (1997).
Roy, U. & Kornitzer, D. "Heme-iron acquisition in fungi," Curr Opin Microbiol 52, 77-83 (2019).
Smith, A. & McCulloh, R.J. "Hemopexin and haptoglobin: allies against heme toxicity from hemoglobin not contenders," Front Physiol 6, 187 (2015).
Solomon, L.A., Kodali, G., Moser, C.C. & Dutton, P.L. "Engineering the assembly of heme cofactors in man-made proteins," J Am Chem Soc 136, 3192-3199 (2014).

(Continued)

*Primary Examiner* — Fred H Reynolds
(74) *Attorney, Agent, or Firm* — Parker Highlander PLLC

(57) ABSTRACT

The disclosure relates to engineered heme sequestering peptides and their use in treating cancer and inhibiting microbial infections and colonization.

27 Claims, 30 Drawing Sheets
Specification includes a Sequence Listing.

(56) References Cited

OTHER PUBLICATIONS

Wandersman, C. & Delepelaire, P. "Haemophore functions revisited," Mol Microbiol 85, 618-631 (2012).
Van Campen et al "Effect of histidine and certain other amino acids on the absorption of iron 59 by rats", J. Nutrition 99, p. 68-74, (1969).

* cited by examiner

```
                                                    Heme binding segment 1
                         1                                                                              15
Yersinia pestis            MSTTTQYNSNYADYSISSYLREMANNFQDIDQAPAETK------DRGSFSGSSTLFSGTQYA
Erwinia carotovora         MSFAITYDAYYANYSIANYLTEWSAAFGDVNHTTGNTQVGGNNTEGFYGGDTFIDSQYA
Pectobacterium carotovorum MSFAITYDAYYANYSIASYLTEWSAAFGDVNHTAGNTQVGGNNTEGFYGGDTFIDSTQYA
Pseudomonas fluorescens    MSISISYSATYGGNTVAQYLTDWSAYPGDVNHRPGEVV-DGTNTGGFNPG--PFDGTQYA 110
                                               Heme binding segment 2
                         60                                                                            100
Yersinia pestis            IGSSHSNPEGMIAEGDLKYSFM---FQHTFHGQIDTLQFGKDLATNAGGPSAGK--HLEKI
Erwinia carotovora         ITSTQNDFSALIAGGDLTYSLESPPANTLYGDLDSLSFGNVLQG---GTTAGTTYSLVEP
Pectobacterium carotovorum ITSTQNDFSALIAGGDLTYSLFTPPANTLYGDLDSLSFGNVLQG---GTTAGTTYSLAEP
Pseudomonas fluorescens    IKSTASD-AAFVADGNLHVTLFSNPSHTLWGSVDTISLGDTLAG---GS--GSNYNLVSQ Heme binding segment 3
                                                                                                       150
Yersinia pestis            DITFNELDLSGEFDSGKSMTENHQGDMHKSVRGLMKGNPDPMLEVMKAKGIN------VD
Erwinia carotovora         EVTFSGLDLSTDV----ANLTVSDRGVHDVTYQLMGGQVPLLDALTNAGI------DIN
Pectobacterium carotovorum EVTFSGLDLSTDV----ANLTVSDRGVHDVIYGIMSGQVQPLLDALTNAGI------DIN
Pseudomonas fluorescens    EVSFTNIGLNSLR----EEGRAGEVHKVVYGLMSGDSSALAGEIDALLKAIDPSLSVN 205
Yersinia pestis            TAFKDLSIASQYPDSGYMSDAPMVDTVGVDC-HDMLLAA
Erwinia carotovora         ASLDSLSFATAT-SDAALSADTVDVVGVAETAD--LLAA
Pectobacterium carotovorum ASLDSLSFATAT-SDAALSADTVDVVGVAETAD--LLAA
Pseudomonas fluorescens    STFDDLAAAGVAHVNPAAAAAADVGLVGVQDVAQDWALAA
```

FIG. 8A

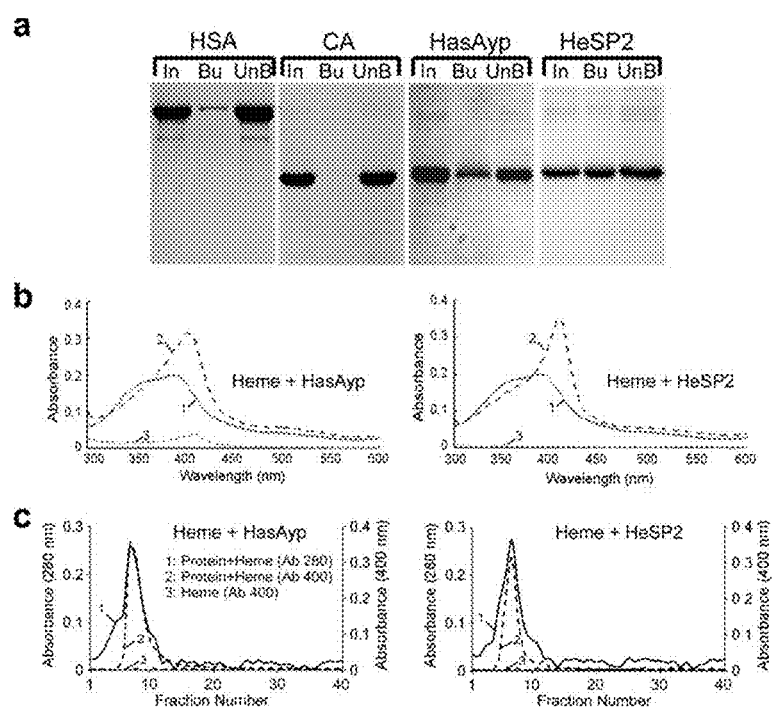
FIGS. 9A-C

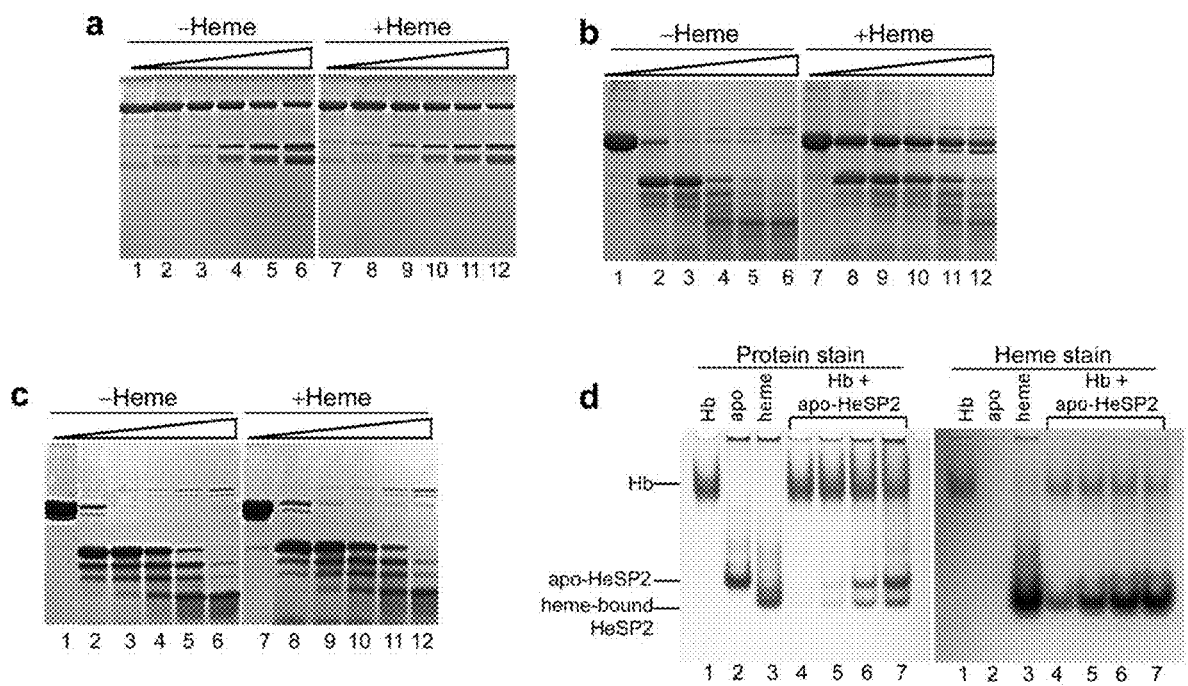
FIGS. 10A-D
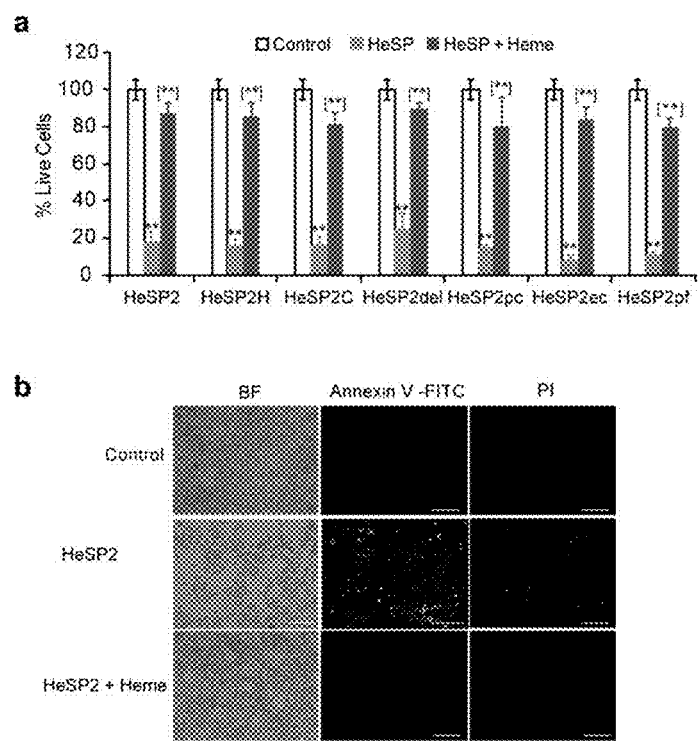
FIGS. 11A-B

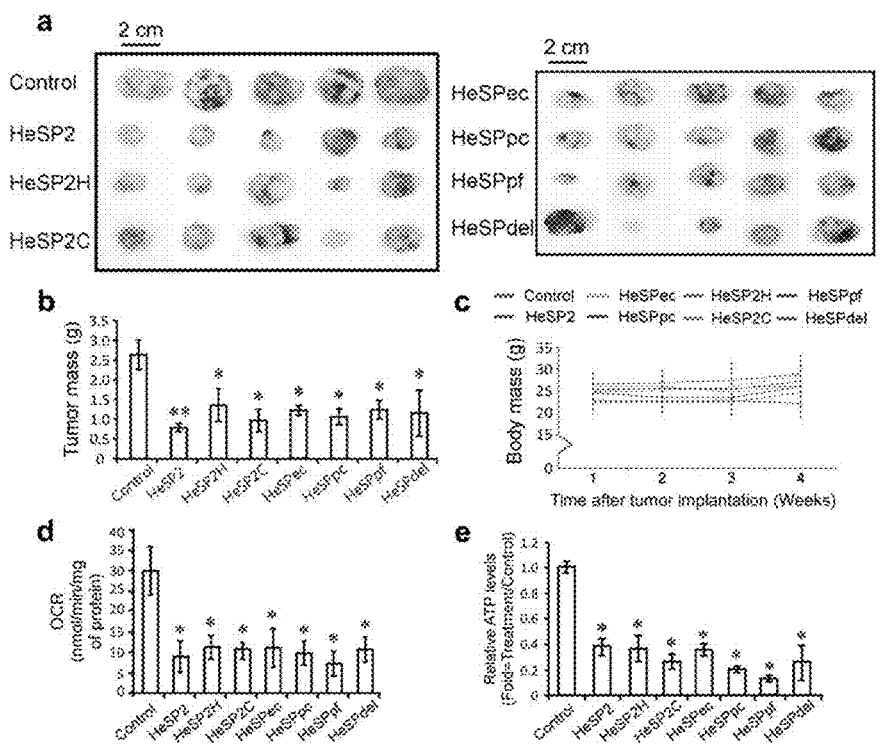
FIGS. 12A-E

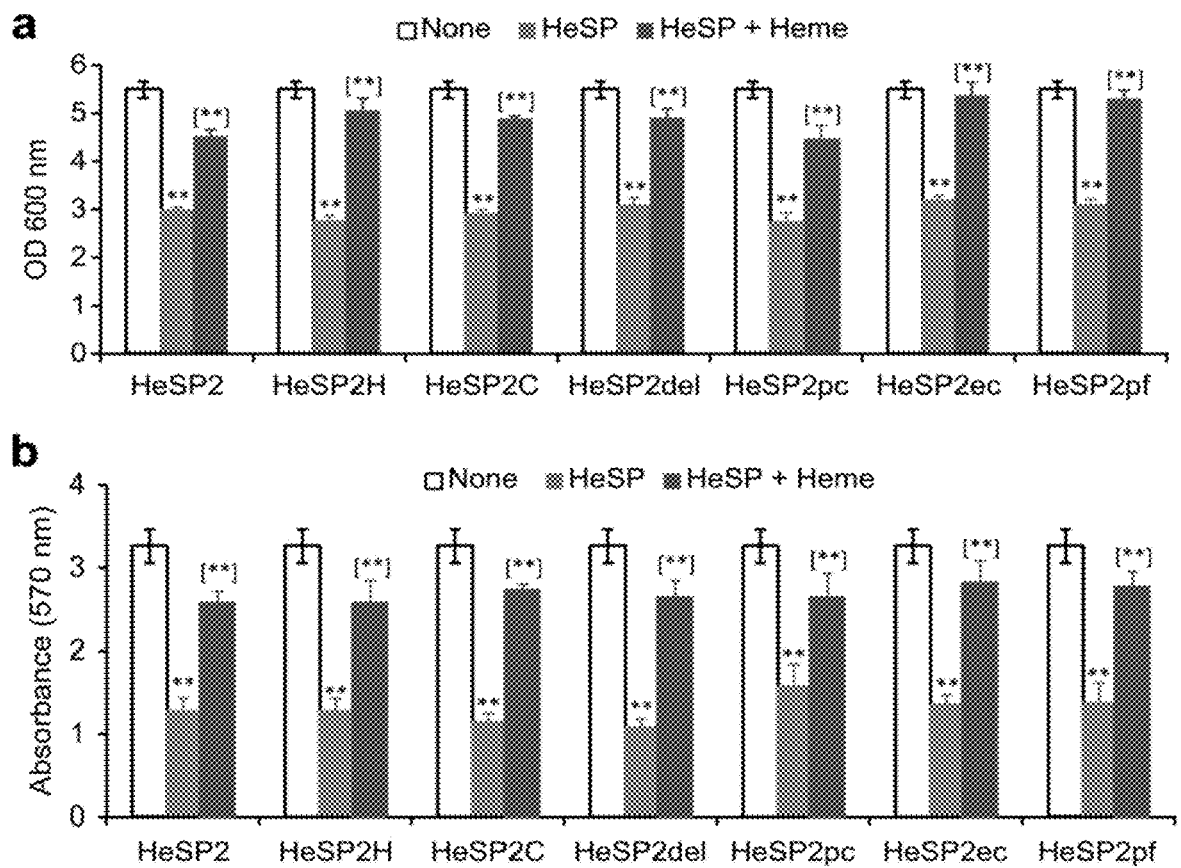
FIGS. 13A-B

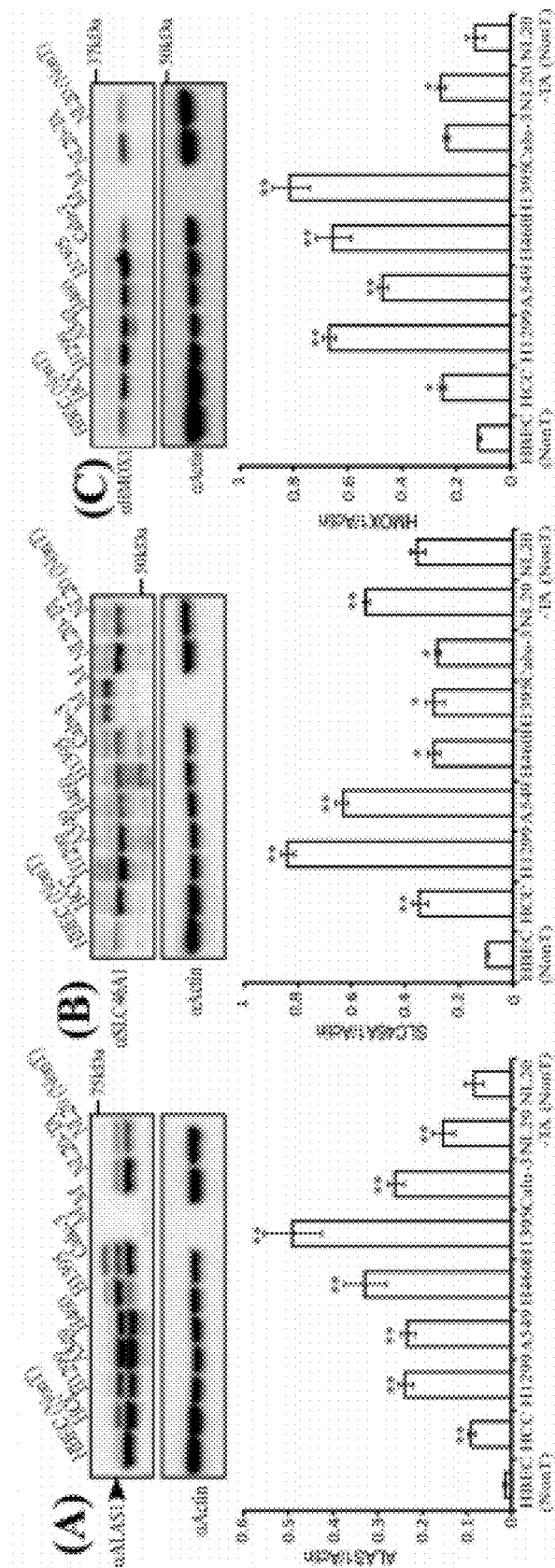
FIGS. 15A-C

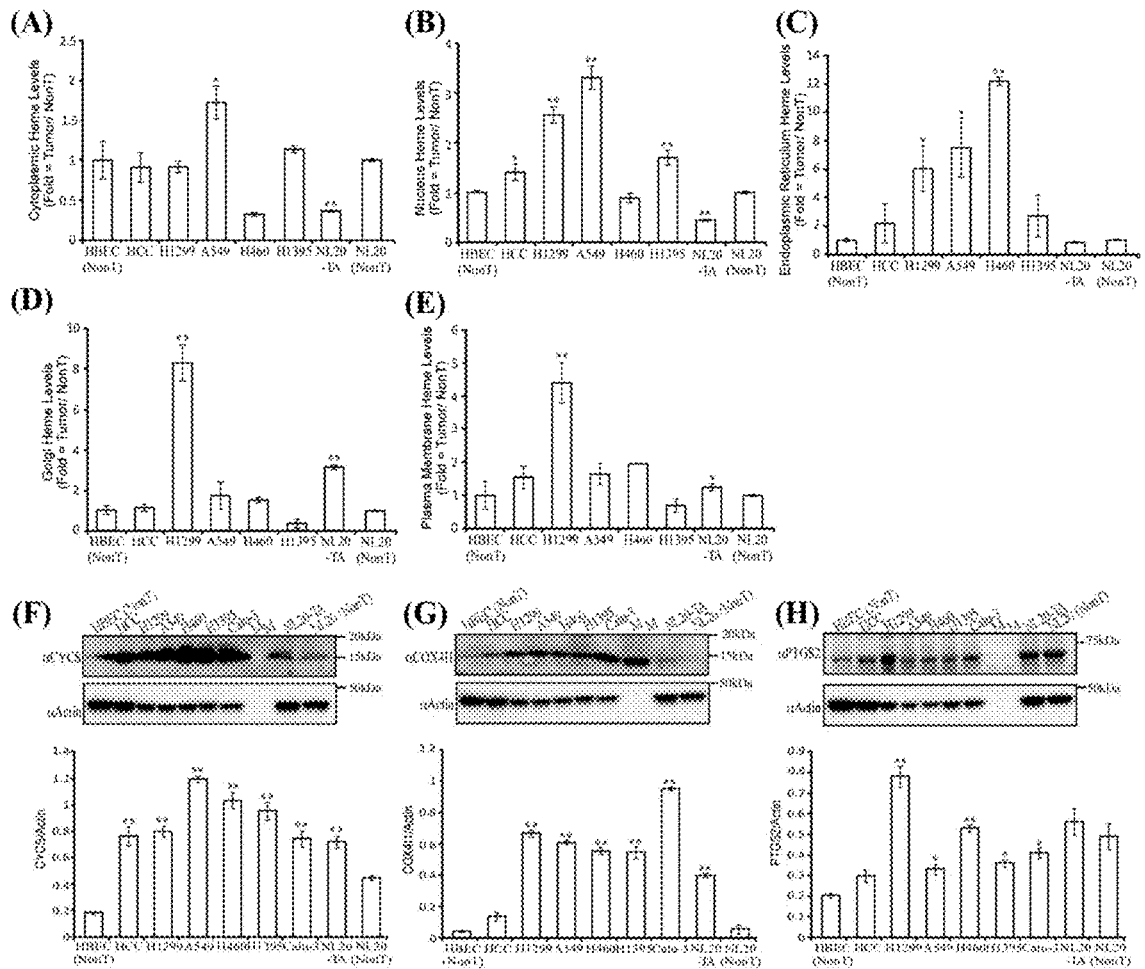
FIGS. 16A-H

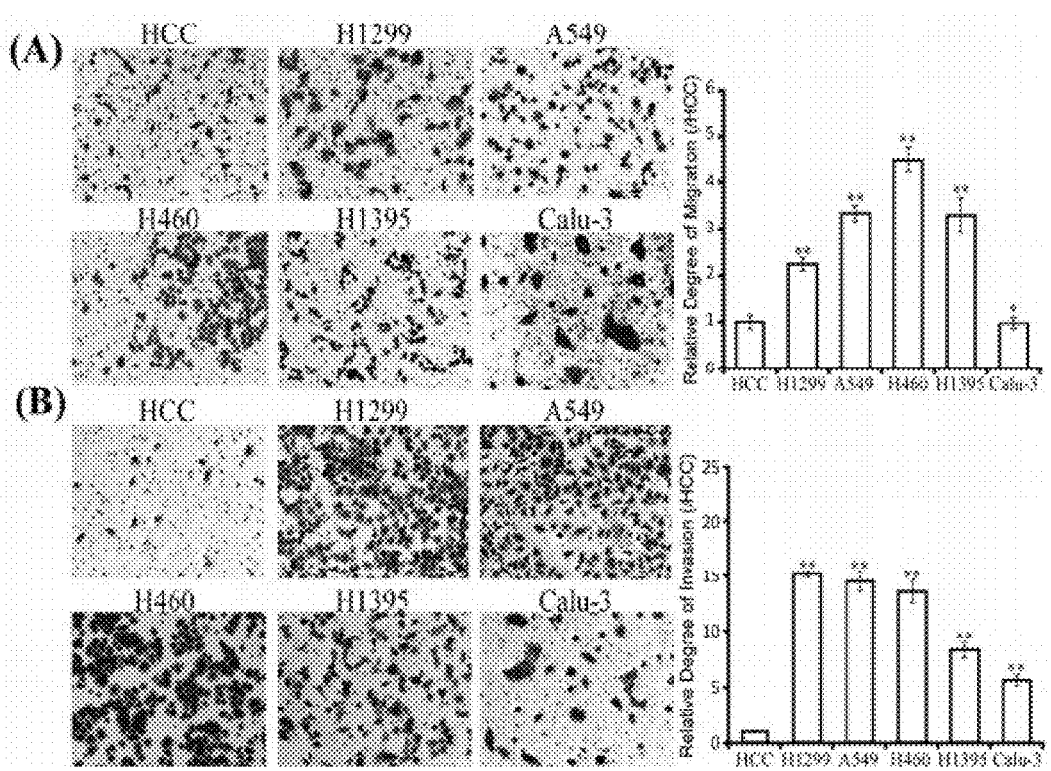
FIGS. 17A-B

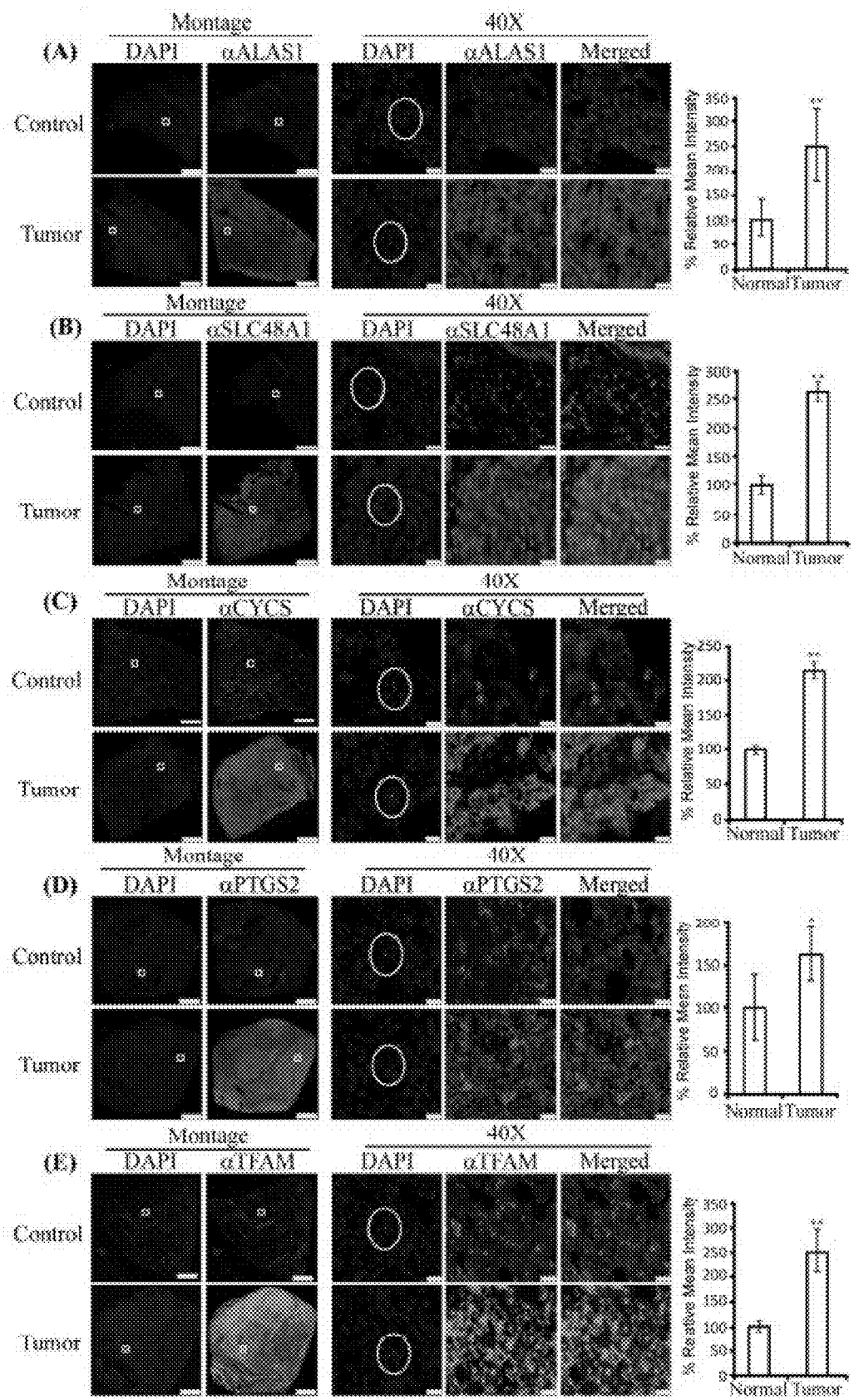
FIGS. 18A-E

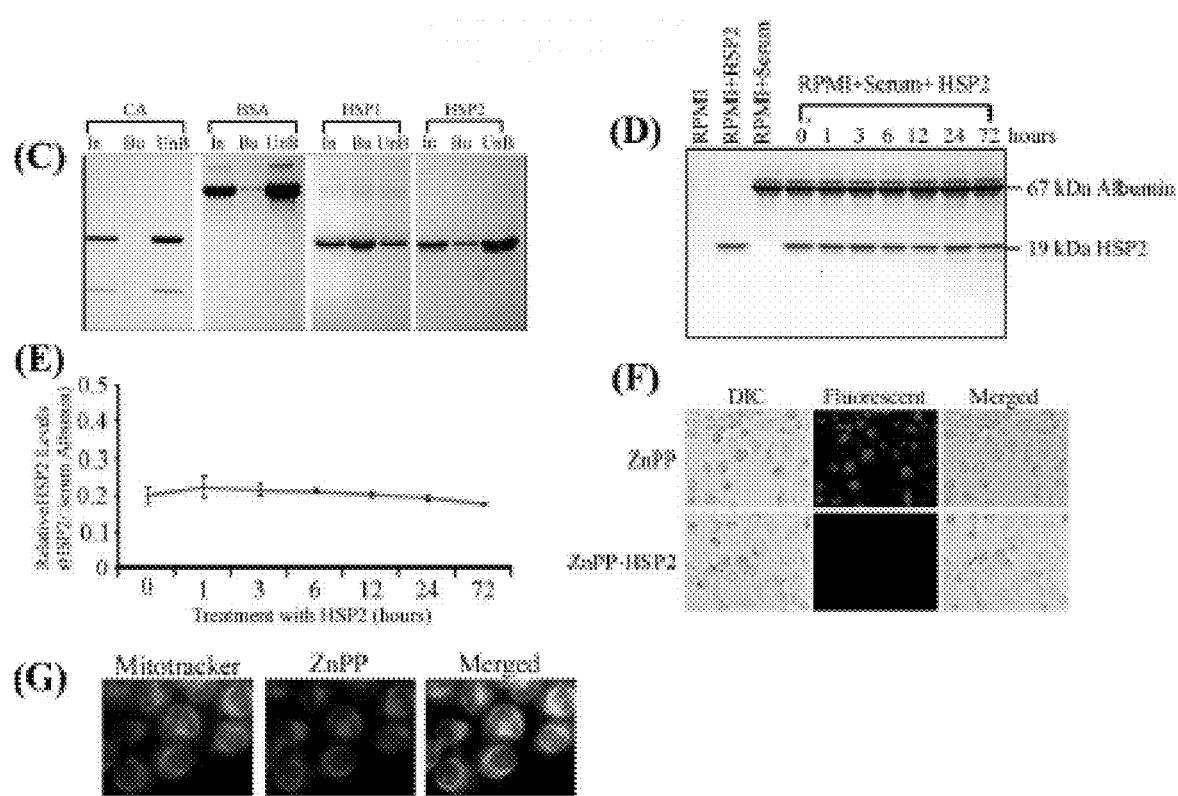
FIGS. 19C-G

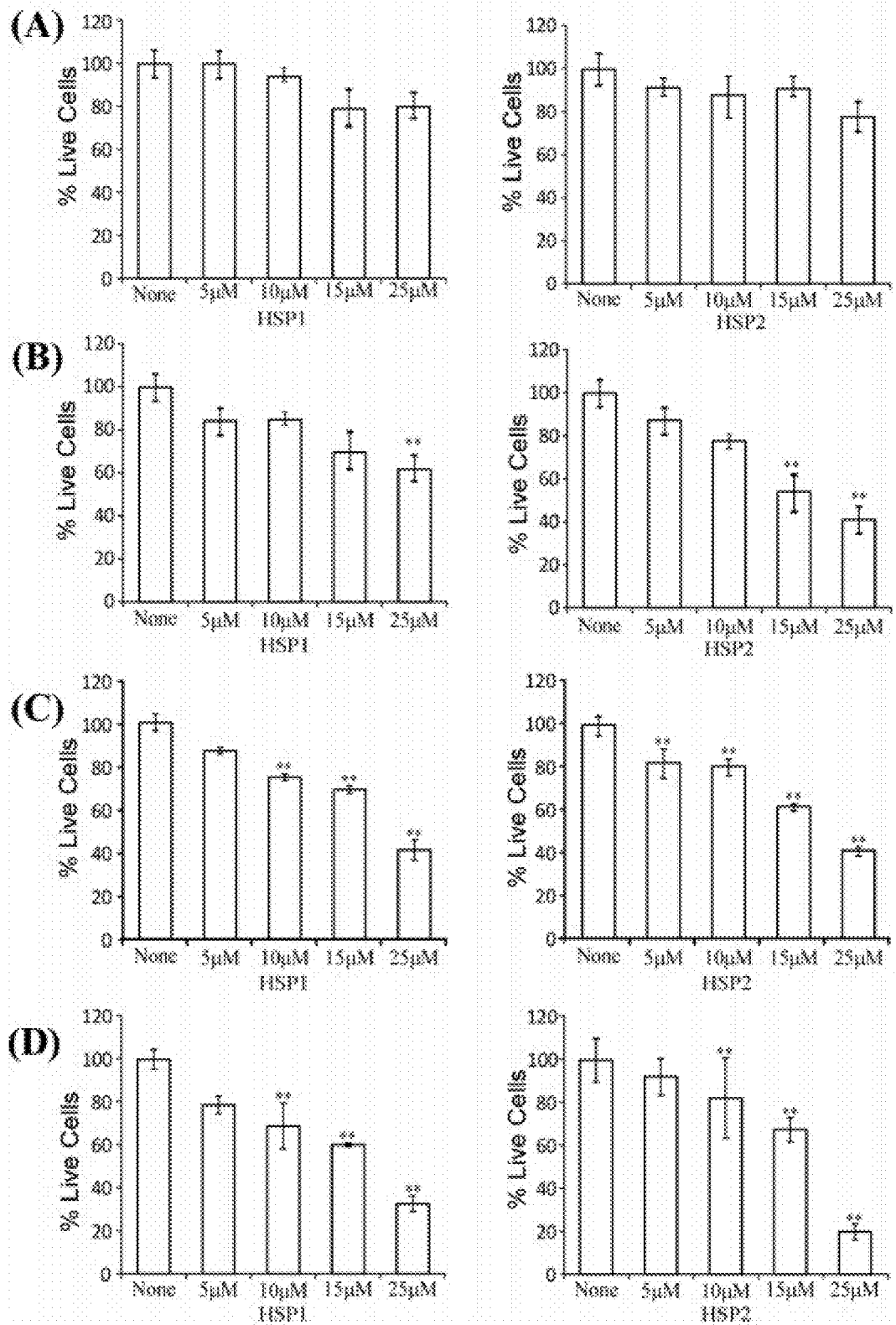
FIGS. 20A-D

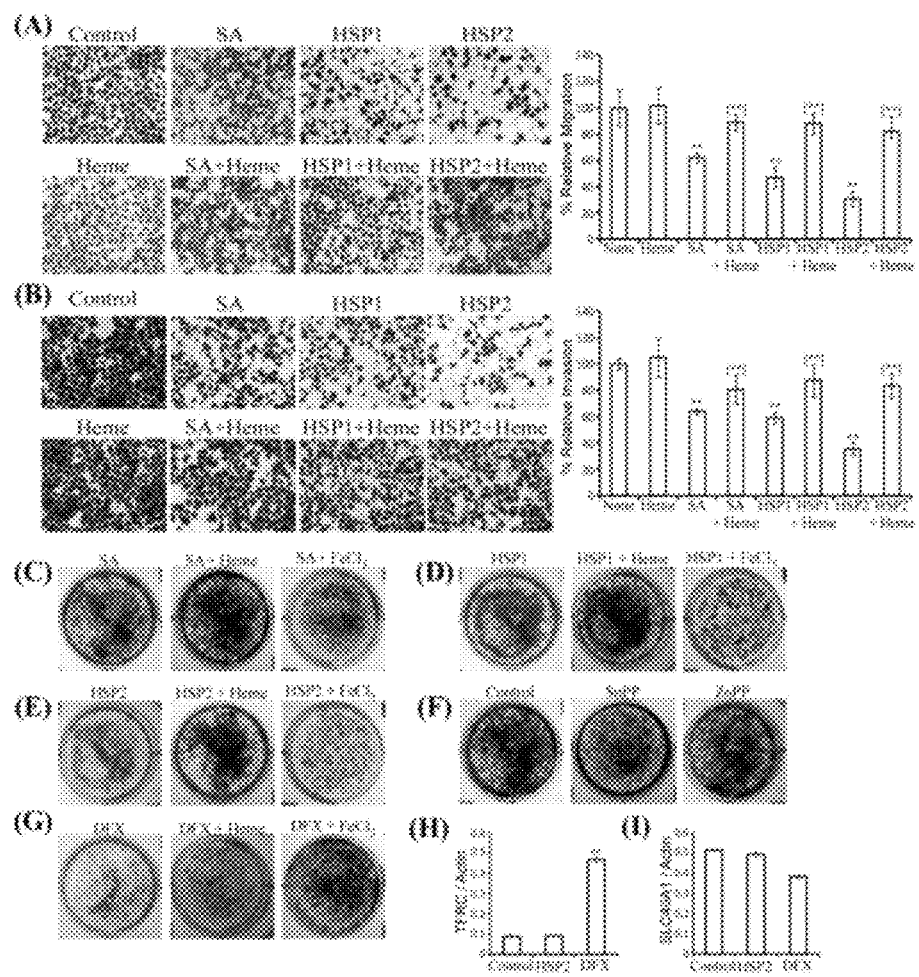
FIGS. 21A-I

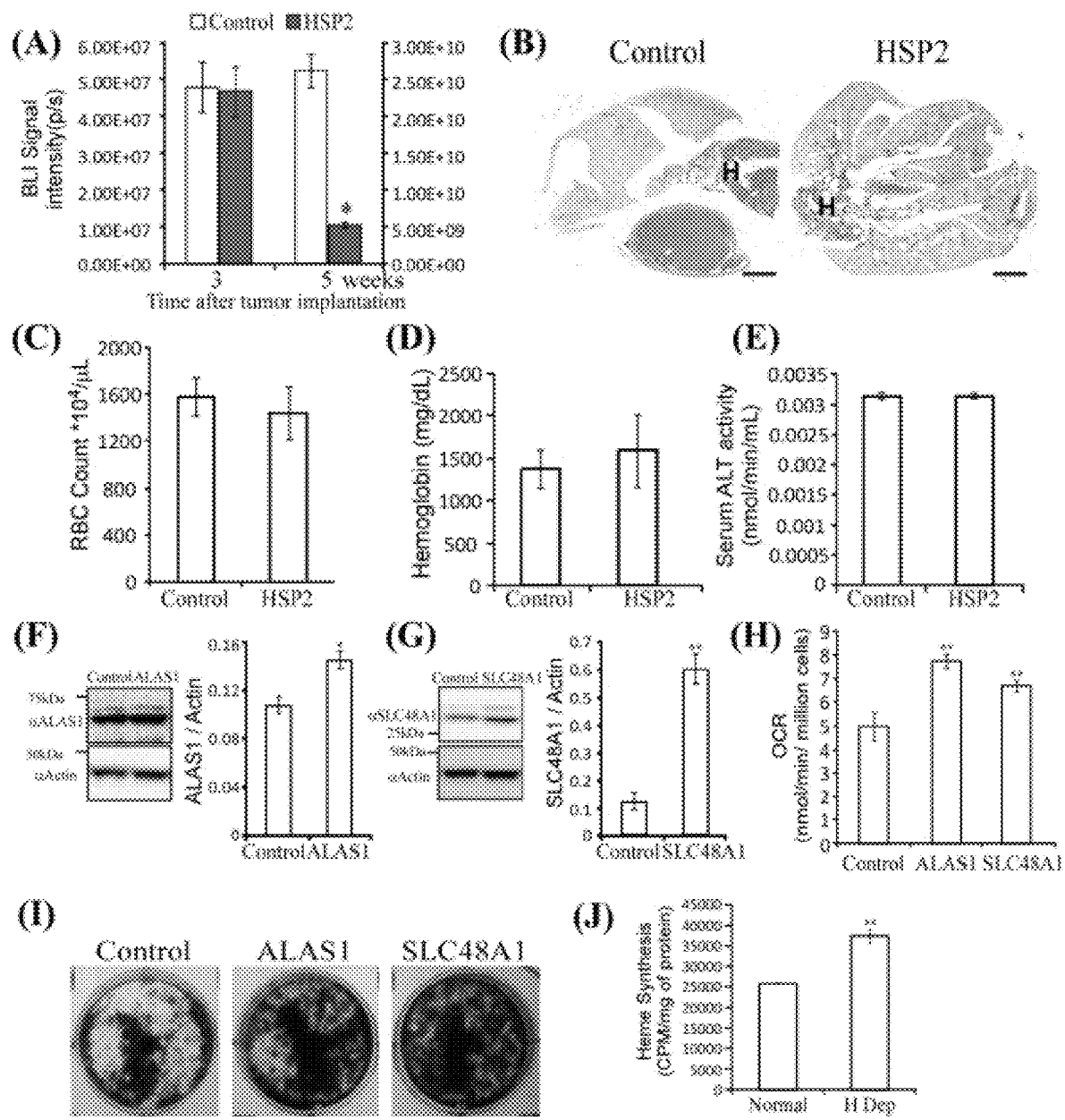
FIGS. 22A-J

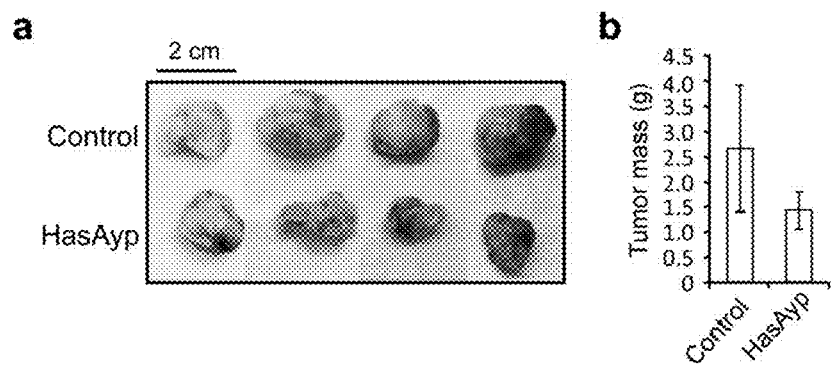
FIGS. 23A-B
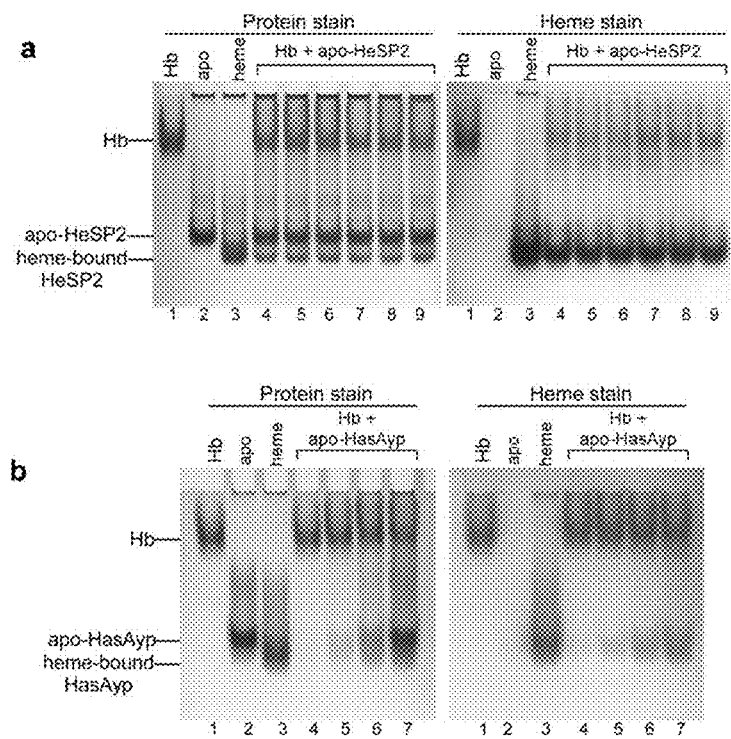
FIGS. 24A-B

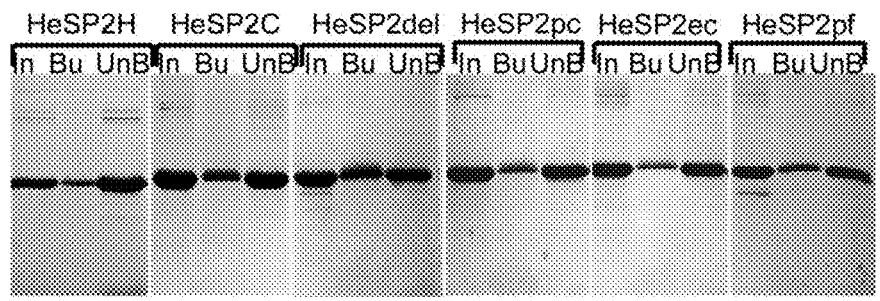
FIG. 25
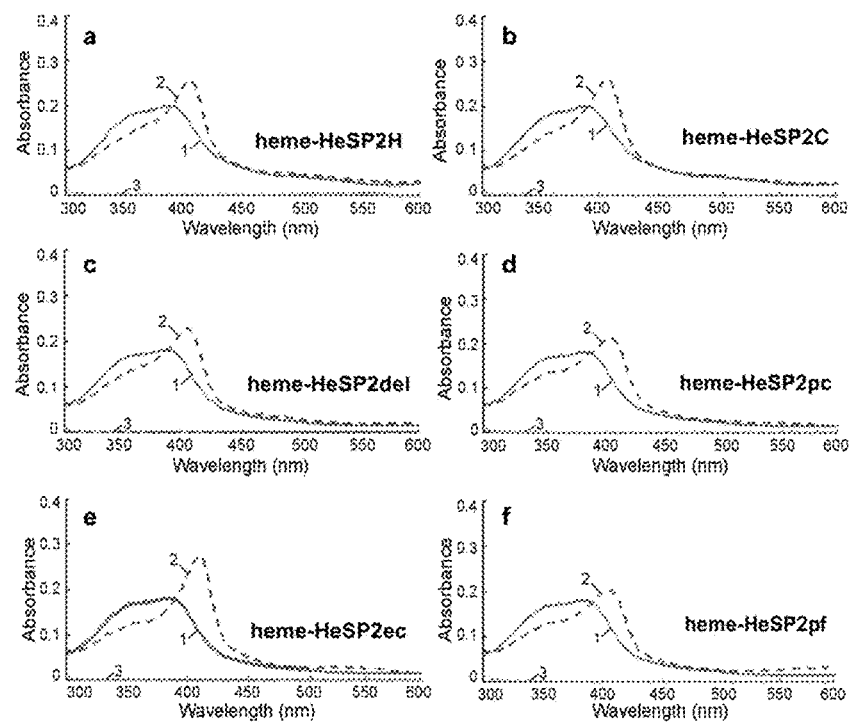
FIGS. 26A-F

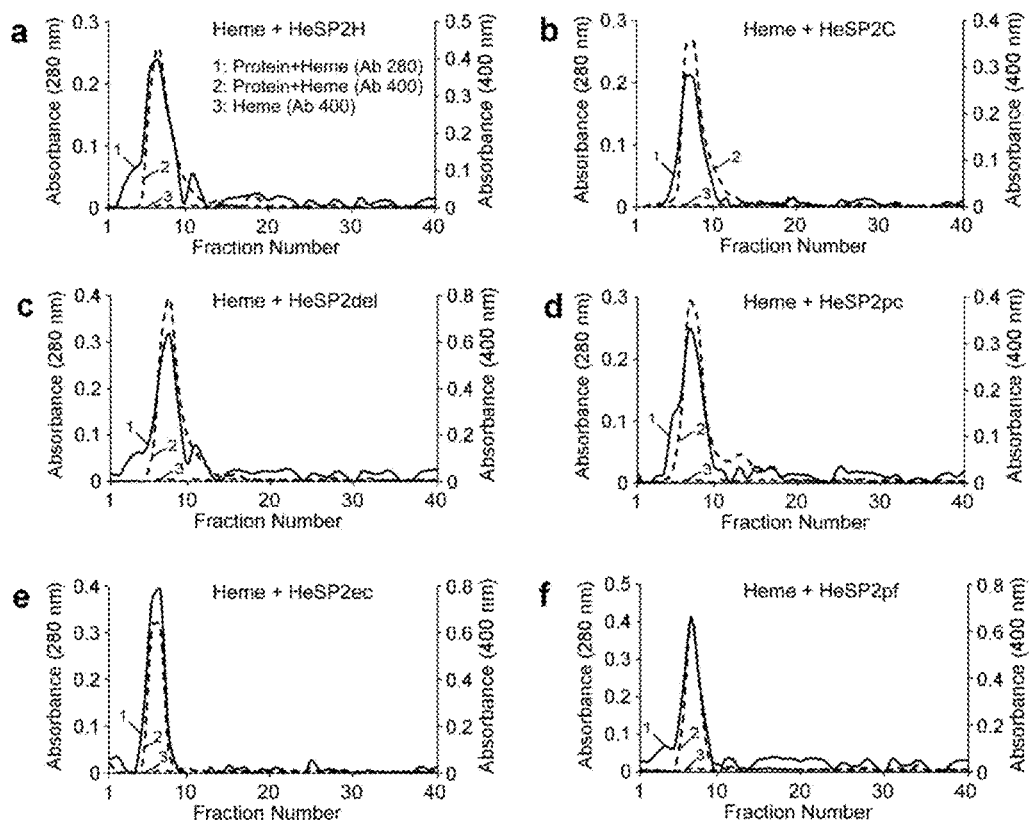
FIGS. 27A-F
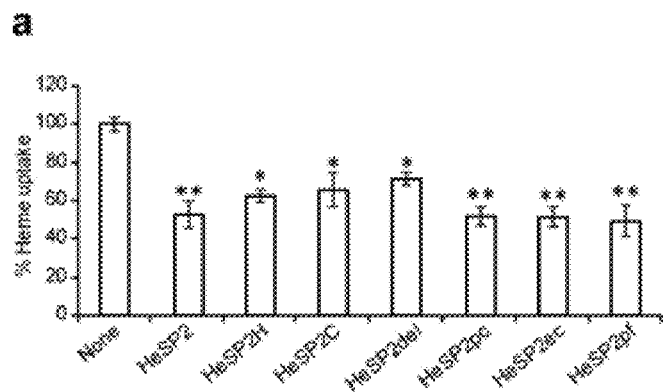
FIG. 28A

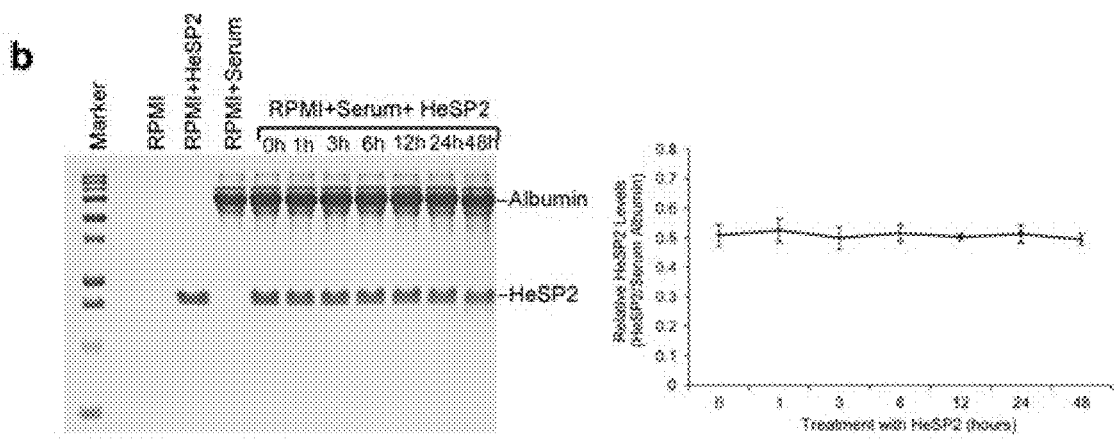
FIG. 28B
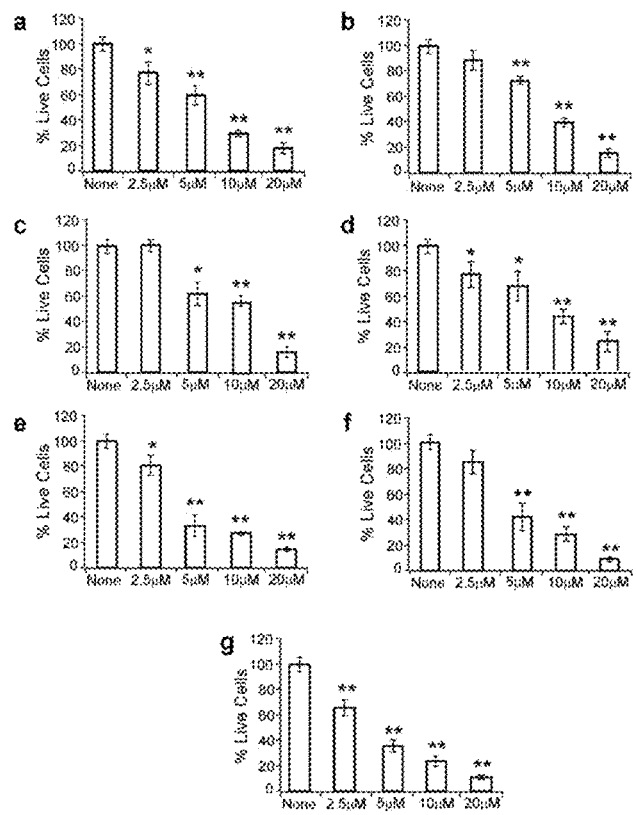
FIGS. 29A-G

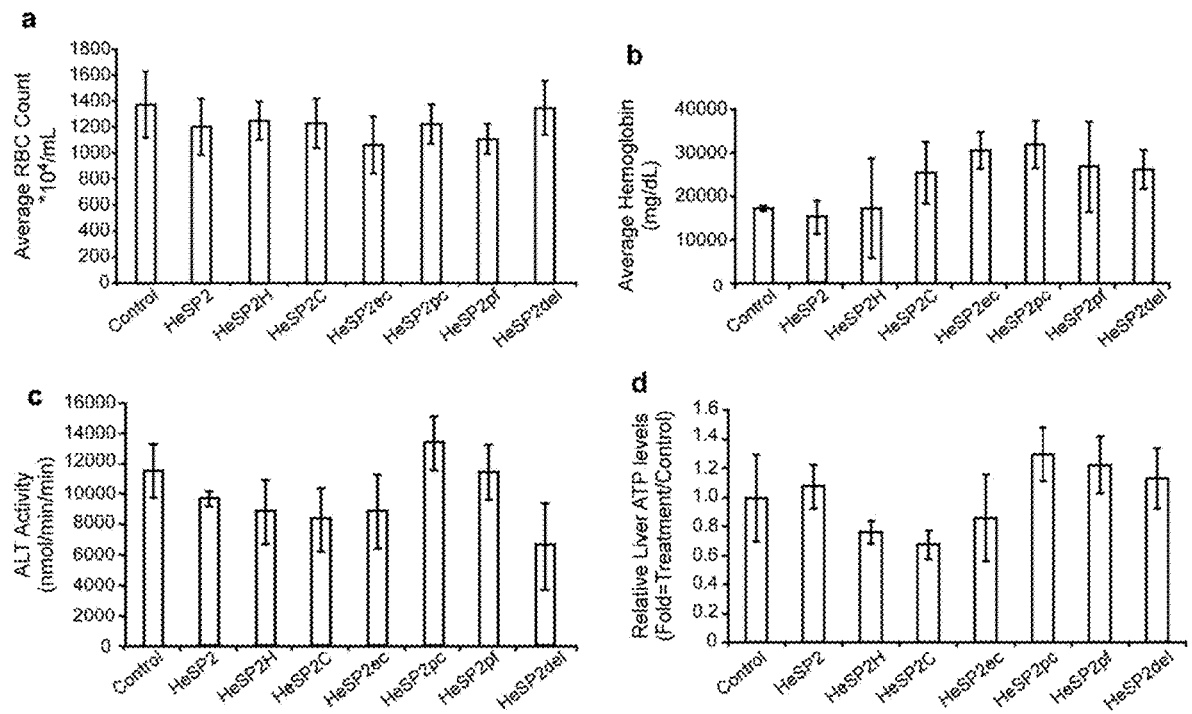
FIGS. 31A-D
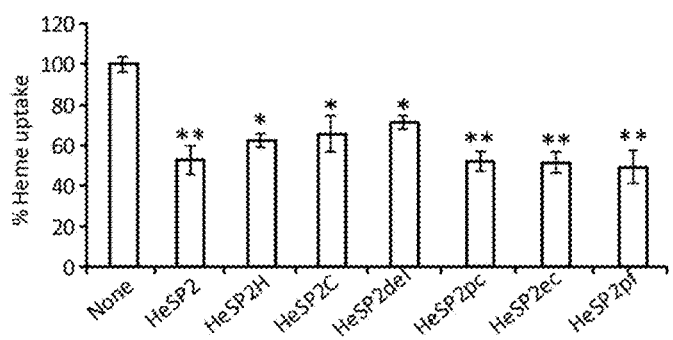
FIG. 32

SEQUENCE LISTING

<160> NUMBER OF SEQ ID NOS: 15

<210> SEQ ID NO 1
<211> LENGTH: 205
<212> TYPE: PRT
<213> ORGANISM: Yersinia pestis

<400> SEQUENCE: 1

Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp Gln
            20                  25                  30

Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
    50                  55                  60

Glu Gly Met Ile Ala Glu Gly Asp Leu Lys Tyr Ser Phe Met Pro Gln
65                  70                  75                  80

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100                 105                 110

Asp Ile Thr Phe Asn Glu Leu Asp Leu Ser Gly Glu Phe Asp Ser Gly
        115                 120                 125

Lys Ser Met Thr Glu Asn His Gln Gly Asp Met His Lys Ser Val Arg
    130                 135                 140

Gly Leu Met Lys Gly Asn Pro Asp Pro Met Leu Glu Val Met Lys Ala
145                 150                 155                 160

Lys Gly Ile Asn Val Asp Thr Ala Phe Lys Asp Leu Ser Ile Ala Ser
                165                 170                 175

Gln Tyr Pro Asp Ser Gly Tyr Met Ser Asp Ala Pro Met Val Asp Thr
            180                 185                 190

Val Gly Val Val Asp Cys His Asp Met Leu Leu Ala Ala
        195                 200                 205

<210> SEQ ID NO 2
<211> LENGTH: 193
<212> TYPE: PRT
<213> ORGANISM: Artificial sequence
<220> FEATURE:
<223> OTHER INFORMATION: Synthetic polypeptide

<400> SEQUENCE: 2

Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp Gln
            20                  25                  30

Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
    50                  55                  60

Glu Gly Met Ile Ala Glu Gly Asp Leu Lys Tyr Ser Phe Met Pro Gln
65                  70                  75                  80

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100                 105                 110

Asp Ile Thr Phe Asn Glu Leu Asp Leu Ser Gly Glu Phe Asp Ser Gly
        115                 120                 125

Lys Ser Met Thr Glu Asn His Gln Gly Asp Met His Lys Ser Val Arg
    130                 135                 140

Gly Leu Met Lys Gly Asn Pro Asp Pro Met Leu Glu Val Met Lys Ala
145                 150                 155                 160

```
Lys Gly Ile Asn Val Asp Thr Ala Phe Lys Asp Leu Ser Ile Ala Ser
            165                 170                 175

Gln Tyr Pro Asp Ser Gly Tyr Met Ser Asp Ala Pro Met Val Asp Thr
        180                 185                 190

Val

<210> SEQ ID NO 3
<211> LENGTH: 193
<212> TYPE: PRT
<213> ORGANISM: Artificial sequence
<220> FEATURE:
<223> OTHER INFORMATION: Synthetic polypeptide

<400> SEQUENCE: 3

Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
            20                  25                  30

Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
    50                  55                  60

Glu Gly Met Ile Ala Glu Gly Asp Leu Lys Tyr Ser Phe Met Pro Gln
65                  70                  75                  80

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100                 105                 110

Asp Ile Thr Phe Asn Glu Leu Asp Leu Ser Gly Glu Phe Asp Ser Gly
        115                 120                 125

Lys Ser Met Thr Glu Asn His Gln Gly Asp Met His Lys Ser Val Arg
    130                 135                 140

Gly Leu Met Lys Gly Asn Pro Asp Pro Met Leu Glu Val Met Lys Ala
145                 150                 155                 160

Lys Gly Ile Asn Val Asp Thr Ala Phe Lys Asp Leu Ser Ile Ala Ser
                165                 170                 175

Gln Tyr Pro Asp Ser Gly Tyr Met Ser Asp Ala Pro Met Val Asp Thr
            180                 185                 190

Val

<210> SEQ ID NO 4
<211> LENGTH: 193
<212> TYPE: PRT
<213> ORGANISM: Artificial sequence
<220> FEATURE:
<223> OTHER INFORMATION: Synthetic polypeptide

<400> SEQUENCE: 4

Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
            20                  25                  30

Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
    50                  55                  60

Glu Gly Met Ile Ala Glu Gly Asp Leu Lys Met Ser Phe Met Pro Gln
```

```
                    65                  70                  75                  80
His Thr Phe His Gly Gln Ile Asp Thr Leu Gln Phe Gly Lys Asp Leu
                    85                  90                  95

Ala Thr Asn Ala Gly Gly Pro Ser Ala Gly Lys His Leu Glu Lys Ile
                100                 105                 110

Asp Ile Thr Phe Asn Glu Leu Asp Leu Ser Gly Glu Phe Asp Ser Gly
                115                 120                 125

Lys Ser Met Thr Glu Asn His Gln Gly Asp Met His Lys Ser Val Arg
                130                 135                 140

Gly Leu Met Lys Gly Asn Pro Asp Pro Met Leu Glu Val Met Lys Ala
145                 150                 155                 160

Lys Gly Ile Asn Val Asp Thr Ala Phe Lys Asp Leu Ser Ile Ala Ser
                    165                 170                 175

Gln Tyr Pro Asp Ser Gly Tyr Met Ser Asp Ala Pro Met Val Asp Thr
                180                 185                 190

Val

<210> SEQ ID NO 5
<211> LENGTH: 193
<212> TYPE: PRT
<213> ORGANISM: Artificial sequence
<220> FEATURE:
<223> OTHER INFORMATION: Synthetic polypeptide

<400> SEQUENCE: 5

Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
                20                  25                  30

Ala Pro Ala Glu Thr Lys Asp Arg Gly Ser Phe Ser Gly Ser Ser Thr
                35                  40                  45

Leu Phe Ser Gly Thr Gln Tyr Ala Ile Gly Ser Ser His Ser Asn Pro
            50                  55                  60

Glu Gly Met Ile Ala Glu Gly Asp Leu Lys His Ser Phe Met Pro Gln
65                  70                  75                  80

His Thr Phe His Gly Gln Ile Asp Thr Leu Gln Phe Gly Lys Asp Leu
                    85                  90                  95

Ala Thr Asn Ala Gly Gly Pro Ser Ala Gly Lys His Leu Glu Lys Ile
                100                 105                 110

Asp Ile Thr Phe Asn Glu Leu Asp Leu Ser Gly Glu Phe Asp Ser Gly
                115                 120                 125

Lys Ser Met Thr Glu Asn His Gln Gly Asp Met His Lys Ser Val Arg
                130                 135                 140

Gly Leu Met Lys Gly Asn Pro Asp Pro Met Leu Glu Val Met Lys Ala
145                 150                 155                 160

Lys Gly Ile Asn Val Asp Thr Ala Phe Lys Asp Leu Ser Ile Ala Ser
                    165                 170                 175

Gln Tyr Pro Asp Ser Gly Tyr Met Ser Asp Ala Pro Met Val Asp Thr
                180                 185                 190

Val

<210> SEQ ID NO 6
<211> LENGTH: 193
<212> TYPE: PRT
<213> ORGANISM: Artificial sequence
<220> FEATURE:
```

<223> OTHER INFORMATION: Synthetic polypeptide

<400> SEQUENCE: 6

```
Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
            20                  25                  30

Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
50                  55                  60

Glu Gly Met Ile Ala Glu Gly Asp Leu Lys Cys Ser Phe Met Pro Gln
65                  70                  75                  80

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100                 105                 110

Asp Ile Thr Phe Asn Glu Leu Asp Leu Ser Gly Glu Phe Asp Ser Gly
        115                 120                 125

Lys Ser Met Thr Glu Asn His Gln Gly Asp Met His Lys Ser Val Arg
130                 135                 140

Gly Leu Met Lys Gly Asn Pro Asp Pro Met Leu Glu Val Met Lys Ala
145                 150                 155                 160

Lys Gly Ile Asn Val Asp Thr Ala Phe Lys Asp Leu Ser Ile Ala Ser
                165                 170                 175

Gln Tyr Pro Asp Ser Gly Tyr Met Ser Asp Ala Pro Met Val Asp Thr
            180                 185                 190

Val
```

<210> SEQ ID NO 7
<211> LENGTH: 184
<212> TYPE: PRT
<213> ORGANISM: Artificial sequence
<220> FEATURE:
<223> OTHER INFORMATION: Synthetic polypeptide

<400> SEQUENCE: 7

```
Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
            20                  25                  30

Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
50                  55                  60

Glu Gly Met Ile Ala Glu Gly Asp Leu Lys Met Ser Phe Met Pro Gln
65                  70                  75                  80

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100                 105                 110

Asp Ile Thr Phe Asn Glu Leu Asp Leu Ser Gly Glu Asn His Gln Gly
        115                 120                 125

Asp Met His Lys Ser Val Arg Gly Leu Met Lys Gly Asn Pro Asp Pro
130                 135                 140
```

```
Met Leu Glu Val Met Lys Ala Lys Gly Ile Asn Val Asp Thr Ala Phe
145                 150                 155                 160

Lys Asp Leu Ser Ile Ala Ser Gln Tyr Pro Asp Ser Gly Tyr Met Ser
                165                 170                 175

Asp Ala Pro Met Val Asp Thr Val
                180
```

<210> SEQ ID NO 8
<211> LENGTH: 192
<212> TYPE: PRT
<213> ORGANISM: Artificial sequence
<220> FEATURE:
<223> OTHER INFORMATION: Synthetic polypeptide

<400> SEQUENCE: 8

```
Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
                20                  25                  30

Ala Pro Ala Glu Thr Lys Asp Arg Gly Ser Phe Ser Gly Ser Ser Thr
            35                  40                  45

Leu Phe Ser Gly Thr Gln Tyr Ala Ile Gly Ser Ser His Ser Asn Pro
    50                  55                  60

Glu Gly Met Ile Ala Glu Gly Asp Leu Lys Met Ser Phe Met Pro Gln
65                  70                  75                  80

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100                 105                 110

Asp Ile Thr Phe Asn Glu Leu Asp Leu Ser Gly Glu Phe Asp Ser Gly
        115                 120                 125

Leu Thr Val Ser Asp Arg Gly Val Val His Asp Val Ile Tyr Gly Leu
    130                 135                 140

Met Gly Gly Gln Val Gln Pro Leu Leu Asp Ala Leu Thr Asn Ala Gly
145                 150                 155                 160

Ile Asp Ile Asn Ala Ser Leu Asp Ser Leu Ser Phe Ala Thr Ala Thr
                165                 170                 175

Ser Asp Ala Ala Leu Ser Ala Asp Thr Val Val Asp Val Val Gly Val
            180                 185                 190
```

<210> SEQ ID NO 9
<211> LENGTH: 194
<212> TYPE: PRT
<213> ORGANISM: Artificial sequence
<220> FEATURE:
<223> OTHER INFORMATION: Synthetic polypeptide

<400> SEQUENCE: 9

```
Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
                20                  25                  30

Ala Pro Ala Glu Thr Lys Asp Arg Gly Ser Phe Ser Gly Ser Ser Thr
            35                  40                  45

Leu Phe Ser Gly Thr Gln Tyr Ala Ile Gly Ser Ser His Ser Asn Pro
    50                  55                  60

Glu Gly Met Ile Ala Glu Gly Asp Leu Lys Met Ser Phe Met Pro Gln
65                  70                  75                  80
```

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100                 105                 110

Asp Ile Thr Phe Asn Glu Leu Asp Leu Ser Gly Glu Phe Asp Ser Gly
        115                 120                 125

Lys Ser Met Thr Glu Asn His Gln Gly Val Val His Asp Val Ile Tyr
130                 135                 140

Gly Leu Met Ser Gly Gln Val Gln Pro Leu Leu Asp Ala Leu Thr Asn
145                 150                 155                 160

Ala Gly Ile Asp Ile Asn Ala Ser Leu Asp Ser Leu Ser Phe Ala Thr
                165                 170                 175

Ala Thr Ser Asp Ala Ala Leu Ser Ala Asp Thr Val Val Asp Val Val
            180                 185                 190

Gly Val

<210> SEQ ID NO 10
<211> LENGTH: 192
<212> TYPE: PRT
<213> ORGANISM: Artificial sequence
<220> FEATURE:
<223> OTHER INFORMATION: Synthetic polypeptide

<400> SEQUENCE: 10

Met Ser Thr Thr Ile Gln Tyr Asn Ser Asn Tyr Ala Asp Tyr Ser Ile
1               5                   10                  15

Ser Ser Tyr Leu Arg Glu Trp Ala Asn Asn Phe Gly Asp Ile Asp His
            20                  25                  30

Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
50                  55                  60

Glu Gly Met Ile Ala Glu Gly Asp Leu Lys Met Ser Phe Met Pro Gln
65                  70                  75                  80

His Thr Phe His Gly Gln Ile Asp Thr Leu Gln Phe Gly Lys Asp Leu
                85                  90                  95

Ala Thr Asn Ala Gly Ser Asn Tyr Asn Leu Val Ser Gln Glu Val Ser
            100                 105                 110

Phe Thr Asn Leu Gly Leu Asn Ser Leu Lys Glu Glu Gly Arg Ala Gly
        115                 120                 125

Glu Val His Lys Val Val Tyr Gly Leu Met Ser Gly Asp Ser Ser Ala
130                 135                 140

Leu Ala Gly Glu Ile Asp Ala Leu Leu Lys Ala Ile Asp Pro Ser Leu
145                 150                 155                 160

Ser Val Asn Ser Thr Phe Asp Asp Leu Ala Ala Ala Gly Val Ala His
                165                 170                 175

Val Asn Pro Ala Ala Ala Ala Ala Asp Val Gly Leu Val Gly Val
            180                 185                 190

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Phe Asp Ser Gly Lys Ser Met Thr Glu
1               5

<210> SEQ ID NO 12
<211> LENGTH: 205
<212> TYPE: PRT
<213> ORGANISM: Erwinia carotovora

<400> SEQUENCE: 12

Met Ser Phe Ala Ile Thr Tyr Asp Ala Tyr Tyr Ala Asn Tyr Ser Ile
1               5                   10                  15

Ala Asn Tyr Leu Thr Glu Trp Ser Ala Ala Phe Gly Asp Val Asn His
            20                  25                  30

Thr Thr Gly Asn Thr Gln Val Gly Gly Asn Asn Thr Gly Gly Phe Tyr
        35                  40                  45

Gly Gly Asp Thr Phe Ile Asp Gly Ser Gln Tyr Ala Ile Thr Ser Thr
    50                  55                  60

Gln Asn Asp Phe Ser Ala Leu Ile Ala Gly Gly Asp Leu Thr Tyr Ser
65                  70                  75                  80

Leu Phe Ser Pro Pro Ala His Thr Leu Tyr Gly Asp Leu Asp Ser Leu
                85                  90                  95

Ser Phe Gly Asn Val Leu Gln Gly Gly Thr Thr Ala Gly Thr Thr Tyr
            100                 105                 110

Ser Leu Val Glu Pro Glu Val Thr Phe Ser Gly Leu Asp Leu Ser Thr
        115                 120                 125

Asp Val Ala Asn Leu Thr Val Ser Asp Arg Gly Val Val His Asp Val
    130                 135                 140

Ile Tyr Gly Leu Met Gly Gly Gln Val Gln Pro Leu Leu Asp Ala Leu
145                 150                 155                 160

Thr Asn Ala Gly Ile Asp Ile Asn Ala Ser Leu Asp Ser Leu Ser Phe
                165                 170                 175

Ala Thr Ala Thr Ser Asp Ala Ala Leu Ser Ala Asp Thr Val Val Asp
            180                 185                 190

Val Val Gly Val Ala Glu Thr Ala Asp Leu Leu Ala Ala
        195                 200                 205

<210> SEQ ID NO 13
<211> LENGTH: 205
<212> TYPE: PRT
<213> ORGANISM: Pectobacterium carotovorum

<400> SEQUENCE: 13

Met Ser Phe Ala Ile Thr Tyr Asp Ala Tyr Tyr Ala Asn Tyr Ser Ile
1               5                   10                  15

Ala Ser Tyr Leu Thr Glu Trp Ser Ala Ala Phe Gly Asp Val Asn His
            20                  25                  30

Thr Ala Gly Asn Thr Gln Val Gly Gly Asn Asn Thr Gly Gly Phe Tyr
        35                  40                  45

Gly Gly Asp Thr Phe Ile Asp Gly Thr Gln Tyr Ala Ile Thr Ser Thr
    50                  55                  60

Gln Asn Asp Phe Ser Ala Leu Ile Ala Gly Gly Asp Leu Thr Tyr Ser
65                  70                  75                  80

Leu Phe Ser Pro Pro Ala His Thr Leu Trp Gly Gln Leu Asp Ser Leu
                85                  90                  95

Ser Phe Gly Asn Val Leu Gln Gly Gly Thr Thr Ala Gly Thr Thr Tyr
            100                 105                 110

Ser Leu Ala Glu Pro Glu Val Thr Phe Ser Gly Leu Asp Leu Ser Thr
        115                 120                 125

Asp Ile Ala Asn Gln Thr Val Ser Asp Arg Gly Val His Asp Val
        130                 135                 140

Ile Tyr Gly Leu Met Ser Gly Gln Val Gln Pro Leu Leu Thr Ala Leu
145                 150                 155                 160

Thr Asn Ala Gly Ile Asp Ile Asn Ala Ser Leu Asp Ser Leu Ser Phe
                165                 170                 175

Ala Thr Ala Thr Ala Asp Ala Ala Leu Ser Ala Asp Thr Val Val Asp
                180                 185                 190

Val Val Gly Val Ala Glu Thr Ala Asp Leu Leu Ala Ala
                195                 200                 205

<210> SEQ ID NO 14
<211> LENGTH: 206
<212> TYPE: PRT
<213> ORGANISM: Pseudomonas fluorescens

<400> SEQUENCE: 14

Met Ser Ile Ser Ile Ser Tyr Ser Thr Thr Tyr Ala Ala Ser Thr Val
1               5                   10                  15

Ala Gln Tyr Leu Asn Asp Trp Ser Ala Tyr Phe Gly Asp Leu Asn His
                20                  25                  30

Arg Glu Gly Ser Val Lys Glu Gly Val Asn Thr Gly Phe Asn Pro
            35                  40                  45

Gly Pro Phe Asp Gly Thr Gln Tyr Gly Val Thr Ser Ser Val Ser Asp
        50                  55                  60

Ala Ala Val Val Ala Glu Gly Ser Leu His Tyr Thr Leu Phe Asn Pro
65                  70                  75                  80

Pro Thr His Thr Leu Trp Gly Ser Leu Asp Gly Leu Thr Leu Gly Asp
                85                  90                  95

Thr Leu Ala Gly Gly Ala Ser Ser Gly Gly Tyr Thr Ile Ala Asn Gln
                100                 105                 110

Glu Val Ser Phe Thr Asn Leu Gly Leu Ser Ser Leu Gln Ser Glu Gly
                115                 120                 125

Arg Asp Gly Gln Val His Lys Val Val Tyr Gly Leu Met Ser Gly Asp
        130                 135                 140

Ser Ser Ala Leu Ala Ser Ala Ile Asp Thr Leu Leu Lys Gly Ile Asp
145                 150                 155                 160

Pro Ser Leu Ser Val Asn Ser Thr Phe Asp Gln Leu Ala Ala Ala Gly
                165                 170                 175

Val Ala His Gln Glu Pro Ala Ala Phe Ala Ala Ala Asp Val Gly Leu
                180                 185                 190

Val Gly Ile Gln Asp Ala Pro His Asp Phe Ala Leu Ala Ala
                195                 200                 205

<210> SEQ ID NO 15
<211> LENGTH: 193
<212> TYPE: PRT
<213> ORGANISM: Yersinia pestis

<400> SEQUENCE: 15

Met Ser Thr Thr Ile Gln Tyr Asn Ser Asn Tyr Ala Asp Tyr Ser Ile
1               5                   10 15

Ser Ser Tyr Leu Arg Glu Trp Ala Asn Asn Phe Gly Asp Ile Asp Gln
20 25 30

-continued

```
Ala Pro Ala Glu Thr Lys Asp Arg Gly Ser Phe Ser Gly Ser Ser Thr
        35                  40                  45

Leu Phe Ser Gly Thr Gln Tyr Ala Ile Gly Ser Ser His Ser Asn Pro
        50              55                  60

Glu Gly Met Ile Ala Glu Gly Asp Leu Lys Tyr Ser Phe Met Pro Gln
65              70                  75                      80

His Thr Phe His Gly Gln Ile Asp Thr Leu Gln Phe Gly Lys Asp Leu
                85                  90                  95

Ala Thr Asn Ala Gly Gly Pro Ser Ala Gly Lys His Leu Glu Lys Ile
            100             105                 110

Asp Ile Thr Phe Asn Glu Leu Asp Leu Ser Gly Glu Phe Asp Ser Gly
        115                 120                 125

Lys Ser Met Thr Glu Asn His Gln Gly Asp Met His Lys Ser Val Arg
        130                 135                 140

Gly Leu Met Lys Gly Asn Pro Asp Pro Met Leu Glu Val Met Lys Ala
145                 150                 155                 160

Lys Gly Ile Asn Val Asp Thr Ala Phe Lys Asp Leu Ser Ile Ala Ser
                165                 170                 175

Gln Tyr Pro Asp Ser Gly Tyr Met Ser Asp Ala Pro Met Val Asp Thr
            180                 185                 190

Val
```

HEME SEQUESTING PEPTIDES AND USES THEREFOR

PRIORITY CLAIM

This application is a continuation of U.S. application Ser. No. 16/827,015, filed Mar. 23, 2020, which claims benefit of priority to U.S. Provisional Application Ser. No. 62/821,823, filed Mar. 21, 2019, the entire contents of which are hereby incorporated by reference.

FUNDING

The subject matter of the present was developed with funding from the Cancer Prevention and Research Institute of Texas under Grant No. RP160617.

BACKGROUND

Iron is an essential nutrient for virtually all living organisms due to its ability to accept and donate electrons with relative ease. In humans and mammals, 95% of functional iron is in the form of heme, particularly hemoglobin, which account for two thirds of total body iron (Beutler et al., 2009). In the human blood, cell-free heme exists in micromolar concentrations predominantly in the form of hemoglobin (Oh et al., 2016). Pathogenic microbes have developed sophisticated mechanisms to extract and use heme directly or as an iron source. One effective mechanism of heme acquisition in pathogenic bacteria is the use of hemophores, which are functionally analogous to siderophores (Wandersman & Delepelaire, 2012). Particularly, the HasA-type hemophores have been identified in many Gram-negative bacteria and bind to heme with very high affinity (Kd=18 pM) (Deniau et al., 2003). HasA binds to hemoglobin and extracts heme and delivers heme to the bacterial outer membrane receptor HasR for internalization. In the same vein, pathogenic fungi have also developed sophisticated mechanisms to scavenge and extract heme from human hosts (Bairwa et al., 2017; Roy and Kornitzer, 2019). For example, *Candida albicans* expresses a network of heme-binding proteins to acquire heme from hemoglobin (Kuznets et al., 2014).

In humans, it is increasingly clear that heme import and export are critical for the proper functioning of many cells and tissues, including erythroid and neuronal cells and systems (Khan and Quigley, 2011; Chiabrando et al., 2018; Reddi and Hamza, 2016). While most normal cells in the human body are not exposed to blood directly, tumor cells can be exposed to blood and heme due to leaky vessels. Interestingly, recent studies in the authors' lab showed that non-small cell lung cancer (NSCLC) cells exhibit intensified heme uptake relative to normal cells, leading to elevated and mitochondrial heme levels, mitochondrial oxidative phosphorylation, and ATP generation (Sohoni et al., 2019). Elevated ATP levels promote tumorigenic functions of NSCLC cells. Overexpression of heme uptake proteins further potentiate tumorigenic functions of NSCLC cells. Notably, lung cancer is the leading cause of cancer-related death in the US. About 85-90% of cases are classified as NSCLC (Siegel et al., 2012). Despite the advent of targeted therapies and immunotherapies, an effective treatment or cure for lung cancer remains an unlikely outcome for most patients. The five-year survival rate remains 10-20%, lower than many other cancers, including breast (90%) and prostate (99%) cancers (American Cancer Society, 2019). Thus, novel therapeutic strategies are necessary for dramatically improving the survival rate of lung cancer patients. The elevated need of NSCLC cells for heme affords a new potential strategy for lung cancer treatment.

Heme is a central metabolic and signaling molecule that regulates diverse processes ranging from transcription to microRNA processing (Barr et al., 2012; Mense and Zhang, 2019; Chen and Zhang, 2019; Wissbrock et al., 2019; Small et al., 2009; Shimizu et al., 2019). Heme also serves as a prosthetic group in proteins and enzymes involved in oxygen utilization and metabolism. Heme function and mitochondrial respiration are tightly linked. Multiple subunits in oxidative phosphorylation (OXPHOS) complexes II-IV contain heme. Heme also coordinates the expression and assembly of OXPHOS complexes (Ortiz de Montellano, 2009; Kim et al., 2012; Padmanaban et al., 1989). Clearly, heme possesses unique signaling and structural properties that enable it to coordinate elevated OXPHOS in not only NSCLC cells, but also an array of drug-resistant cancer cells. Recent studies have shown that drug-resistant cells of acute and chronic myeloid leukemia, breast cancer, and melanoma depend on OXPHOS and that targeting oxidative metabolism and mitochondrial respiration overcomes their drug resistance (Farge et al., 2017; Kuntz et al., 2017; Navarro et al., 2016; Zhang et al., 2016; Lee et al., 2017). Thus, it is likely that these drug-resistant cells depend on ample heme supply for their resilient tumorigenicity. Further, a plethora of epidemiological studies have shown that elevated heme intake is associated with an array of common diseases, including several types of cancer, diabetes, and heart disease (Hooda et al., 2014).

SUMMARY

In accordance with the present disclosure, there is provided a recombinant heme sequestering peptide (HeSP) comprising one or more of (a) one or more neutral amino acid substitutions in a heme binding pocket; (b) a fusion of heme binding protein (HBP) sequences from distinct heme binding proteins; and/or (c) a heme binding protein (HBP) having a truncation and/or internal deletion that reduces the immunogenicity of said heme binding protein. The HBP may comprise *Yersinia pestis* HasA sequences. The HeSP may have a single neutral amino acid substitution in a heme binding pocket, such as Q32H, or may have only two neutral amino acid substitutions, such as Q32H and Y75M, Q32H and Y75H, or Q32H and Y75C. The HeSP may comprise distinct heme binding protein are selected from two or more of *Yersinia pestis* HasA, *Erwinia carotovora* HasA, *Pectobacterium carotvorum* HasA and *Pseudomonas fluorescens* HasA. The HeSP may comprise a truncation that reduces immunogenicity is a C-terminal truncation. The HeSP may comprise a deletion that reduces immunogenicity is in the C-terminal half of said heme binding protein. The HeSP may exhibit (a) and (b), (b) and (c), (a) and (c), or all of (a), (b) and (c). The HeSP has the amino acid sequence of SEQ ID NOS: 2-10. The HeSP may be bound to zinc protopoprhyrin.

In another embodiment, there is provided a method of sequestering heme from an environment comprising contact said environment with an HeSP as described herein. The environment may be a biological sample, a cell culture, a surface, such as a plate, tube or well surface, the surface of a medical device. The HeSP may be fixed to a support, such as a column matrix, a well, a plate, a slide, a tube, a dipstick, a bead, or a nanoparticle. The method may further comprise detecting sequestered heme. The method may further comprise quantifying the detected sequestered heme. The environment may be an air handling device or system, a heating/ cooling device or system, a water processing device or system, a water storage device or system, a water transport device or system, or a food processing device or system.

In yet another embodiment, there is provided a method of treating a disease, disorder or condition comprising administering to said subject an HeSP as described herein. The disease may be cancer, such as lung cancer (such as non-small cell lung cancer), colon cancer, head & neck cancer, brain cancer, liver cancer, pancreatic cancer, prostate cancer, ovarian cancer, testicular cancer, uterine cancer, breast cancer (such as triple negative breast cancer), skin cancer (such as melanoma), lymphoma, or leukemia. The cancer may be a recurrent cancer, drug resistant cancer, primary cancer or metastatic cancer. The method may further comprise treating said subject with another cancer therapy such as chemotherapy, radiotherapy, immunotherapy, toxin therapy, hormonal therapy, or surgery. The HeSP may be administered local to a cancer site, regional to a cancer site, or systemically.

The disease may be an infectious disease, such as a fungal disease. The method may further comprise treating said subject with another anti-fungal therapy. The HeSP may be administered local to a site of infection, regional to a site of infection, or systemically.

In a further embodiment, there is provided a method of diagnosing a heme/iron/lead-related disease or disorder in a subject or a sample comprising contacting said sample or subject with an HeSP as described herein.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure.

The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by particular embodiments and optional features, modification and variation of the concepts herein disclosed may be resorted to by those skilled in the art, and that such modifications and variations are considered to be within the scope of this disclosure as defined by the appended claims.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

(FIG. 1A) The levels of heme biosynthesis are elevated, though to a varying degree, in NSCLC cell lines. (FIG. 1B) The levels of heme uptake are elevated in NSCLC cell lines. (FIG. 1C) Elevated heme biosynthesis and uptake can both contribute to increased heme availability to NSCLC cells. (FIG. 1D) The levels of heme degradation are elevated in certain NSCLC cell lines. (FIG. 1E) The levels of transferrin receptor TFRC are not uniformly elevated in NSCLC cell lines. M: molecular marker. (FIG. 1F) Consistent with elevated heme biosynthesis and uptake, the levels of mitochondrial heme are elevated in NSCLC cells. Data are plotted as mean ± SD. For statistical analysis, the levels in tumorigenic cells were compared to the levels in non-tumorigenic cells with a Welch 2-sample t-test. *, p-value, 0.05, **, p-value <0.005.

(FIG. 2A) Oxygen consumption rates are elevated, though to a varying degree, in NSCLC cell lines. (FIG. 2B) ATP levels are elevated in NSCLC cell lines. (FIG. 2C) The levels of mitochondrial biogenesis regulator NRF1 are upregulated in NSCLC cell lines relative to non-tumorigenic cell lines. (FIG. 2D) The levels of mitochondrial biogenesis regulator TFAM are upregulated in NSCLC cell lines relative to non-tumorigenic cell lines. M: molecular marker. Data are plotted as mean ± SD. For statistical analysis, the levels in tumorigenic cells were compared to the levels in non-tumorigenic cells with a Welch 2-sample t-test. *, p-value, 0.05, **, p-value <0.005.

(FIG. 3A) Heme-sequestering peptides (HSPs) inhibit heme uptake in NSCLC cell lines in a reversible manner. In the absence of HSPs, the presence of 60 mM (1×ZnPP) or 120 mM (2×ZnPP) ZnPP resulted the same levels of intracellular uptake, as uptake was saturated above 60 mM. The inhibition of ZnPP uptake by HSPs occurred only at 1×ZnPP, whereas 2×ZnPP completely reversed the inhibition by HSP2, indicating that the presence of HSP2 did not cause irreversible effects on the cells. HSP contains HasA residues 1-193 with no mutations. (FIG. 3B) Mitochondrial heme levels in NSCLC cells gradually decrease as treatment with HSP2 continues. H1299 NSCLC cells bearing the expression plasmid for the peroxidase reporter for mitochondrial heme were treated with 25 mM HSP2 for the indicated time periods, and then reporter activities were measured as described in Methods. The activities were normalized to eGFP fluorescent signals which serve as a control for transfection efficiencies. In FIG. 3B, values were presented as fold changes relative to untreated cells. (FIG. 3C) HSP1 and HSP2 significantly reduce proliferation of NSCLC cell lines but not non-tumorigenic cell line HBEC30KT (HBEC). Data are plotted as mean ± SD. For statistical analysis, the levels in treated cells were compared to the levels in untreated cells (0 hour) with a Welch 2-sample t-test. *, p-value, 0.05, **, p-value <0.005.

(FIG. 4C) The effect of SA on colony formation in H1299 cells. (FIG. 4D) The effect of HSP1 on colony formation in H1299 cells. (FIG. 4E) The effect of HSP2 on colony formation in H1299 cells.

(FIG. 4F) The effects of heme oxygenase inhibitor SnPP and ZnPP on colony formation in H1299 cells. (FIG. 4G) The effect of DFX on colony formation in H1299 cells.

(FIG. 5A) Representative bioluminescence images of mice bearing H1299 lung tumor xenografts treated without (Control) or with HSP2 (25 mg/kg) or HSP2 (10 mg/kg) (n=6/group). Treatment started at 4.5 weeks after tumor cell implantation when authentic BLI signals (>5×10$^6$ photons/second) were detected from tumors of all tested mice. Treatments were stopped, and mice were sacrificed after the untreated mice with tumors appeared moribund. (FIG. 5B) The quantified luminescence signals representing tumor volumes. Data are plotted as mean ± SD. For statistical analysis, the levels in treated tumors were compared to the levels in untreated tumors with a Welch 2-sample t-test. *, p-value <0.05. (FIG. 5C) The body masses of mice under each treatment condition. (FIG. 5D) Representative H&E images of control tumors and tumors treated with HSP2 or control saline. Tumors are marked with light blue outlines. Montage (scale bar: 2 mm), 10× (scale bar: 200 mm), and 40× (scale bar: 50 mm) images of the H&E sections are shown from left to right. The rectangles in Montage and 10× denote the regions shown in 10× and 40×, respectively. (FIG. 5E) Representative IHC images of H1299 NSCLC tumor tissue sections and graph showing the levels of COX5A in control and HSP2-treated tumors. (FIG. 5F) Representative IHC images of H1299 NSCLC tumor tissue sections and graph showing the levels of COX4I1 in control and HSP2-treated tumors. (FIG. 5G) Representative IHC images of H1299 NSCLC tumor tissue sections and graph showing the levels of UQCRC2 in control and HSP2-treated tumors. (FIG. 5H) Representative IHC images of H1299 NSCLC tumor tissue sections and graph showing the levels of CYCS in control and HSP2-treated tumors. Shown are montages and 10× images of control and HSP2-treated tumor tissue sections stained with DAPI or antibodies against the indicated protein. The light blue lines in DAPI images outline the tumors in the lung. The white rectangles in DAPI images denote the regions shown in 10× images. The heart was often stained and is marked with "H". Scale bar: montage, 1 mm; 10×, 20 mm. Protein levels were quantified, and data are plotted as mean ± SEM. The values shown in the graphs are averages of signals quantified from three independent IHC experiments. For statistical analysis, the levels in treated tumors were compared to the levels in control tumors with a Welch 2-sample t-test. **, p-value <0.005.

(FIG. 6A) Images showing dissected tumors from mice implanted with subcutaneous xenografts (H1299-luc cells), treated with saline (control) or HSP2. Treatment started at 1.5 weeks after tumor implantation when authentic BLI signals were detected, and tumors were visible. Mice were sacrificed when tumors in untreated mice reach about 1 cm$^3$. (FIG. 6B) The quantified bioluminescence signals representing tumor volumes from mice bearing subcutaneous xenografts treated with saline (control) or HSP2 (25 mg/kg I.V. every 3 days) (n=4/group). (FIG. 6C) Average masses for control and HSP2-treated tumors (n=4/group). (FIG. 6D) Average body masses of control and HSP2-treated mice. (FIG. 6E) Oxygen consumption rates (OCRs) measured in cells from control and HSP2-treated tumors. (FIG. 6F) ATP levels measured in cells from control and HSP2-treated tumors. Data are plotted as mean ± SEM. For statistical analysis, the levels in HSP2-treated tumors were compared to the levels in control tumors with a Welch 2-sample t-test. **, p-value <0.005.

(FIG. 7A) NSCLC cells overexpressing ALAS1 exhibit increased heme synthesis. (FIG. 7B) NSCLC cells overexpressing SLC48A1 exhibit increased heme uptake. (FIG. 7C) Migration is enhanced in NSCLC cells with elevated heme synthesis or uptake due to overexpression of ALAS1 or SLC48A1. (FIG. 7D) Invasion is enhanced in NSCLC cells with elevated heme synthesis or uptake due to overexpression of ALAS1 or SLC48A1. (FIG. 7E) Images showing tumor xenografts isolated from NOD/SCID mice implanted with control NSCLC cells or cells overexpressing ALAS1 or SLC48A1. (FIG. 7F) Average masses of control tumors and tumors formed by cells overexpressing ALAS1 or SLC48A1 (n=5/group). (FIG. 7G) Oxygen consumption rates (OCRs) measured in cells from control tumors and those with cells overexpressing ALAS1 or SLC48A1. (FIG. 7H) ATP levels measured in cells from control tumors and those with cells overexpressing ALAS1 or SLC48A1. Data are plotted as mean ± SEM. For statistical analysis, the levels in tumors formed by cells overexpressing ALAS1 or SLC48A1 were compared to the levels in control tumors with a Welch 2-sample t-test. **, p-value <0.005.

FIGS. 8A-B. The sequences of bacterial HasA proteins and heme-sequestering proteins (HeSPs). (FIG. 8A) The sequences of hemophore HasA proteins from *Yersinia pestis* (SEQ ID NO: 1) and non-human pathogens *Erwinia carotovora* (SEQ ID NO: 12), *Pectobacterium carotovorum* (SEQ ID NO: 13), and *Pseudomonas fluorescens* (SEQ ID NO: 14). The sequences are divided into three segments. Key heme-binding residues 32 (H or Q) and 75 (Y) are designated with red dots. Residues of the heme-binding pocket in HasA protein from *Yersinia pestis* are in red, conserved residues across the alignment are in green and conservative substitutions in blue. Residues are numbered according to the *Yersinia pestis* sequence. (FIG. 8B) Protein sequence maps of HeSPs generated based on HasA proteins from *Yersinia pestis* and non-pathogenic bacteria.

FIGS. 9A-C. HeSP2, like HasA$_{yp}$, binds to heme strongly. (FIG. 9A) The pull-down of HasA$_{yp}$ and HeSP2 by heme agarose beads. Five hundred picomoles of human serum albumin (HAS, positive control), carbonic anhydrase (CA, negative control), HasA$_{yp}$, and HeSP2 were incubated with heme-agarose beads, respectively. The input (In) proteins, bound (Bu) and unbound proteins (UnB) were analyzed by SDS-PAGE and shown. (FIG. 9B), Absorption spectra of heme in the presence and absence of HasA$_{yp}$ or HeSP2. Line 1: 5 μM heme, line 2: 5 μM heme+10 μM HasA$_{yp}$ or HeSP2, line 3: 10 μM HasA$_{yp}$ or HeSP2. (FIG. 9C) Elution profiles of heme-HeSP mixtures on Sephadex-G50 columns. line1: 0.25 mM heme+0.25 mM HasA$_{yp}$ or HeSP2 (protein absorption at 280 nm), line2: 0.25 mM heme+0.25 mM HasA$_{yp}$ or HeSP2 (heme absorption at 400 nm), line 3: 0.25 mM (heme absorption at 400 nm).

FIGS. 10A-D. (FIGS. 10A-C) HasA$_{yp}$ or HeSP2 exhibit differential sensitivity to chymotrypsin. β-amylase (FIG. 10A, for control), HasAyp (FIG. 10B), and HeSP2 (FIG. 10C) were incubated with or without heme, then chymotrypsin was added to the proteins with increasing concentrations. Untreated (lanes 1 and 7) and chymotrypsin-treated proteins (lanes 2-6 and 8-12) were analyzed by SDS-PAGE. Chymotrypsin concentrations: lanes 2 and 8, 6.25 μg/ml; lanes 3 and 9, 12.5 μg/ml; lanes 4 and 10, 25

µg/ml; lanes 5 and 11, 50 µg/ml; lanes 6 and 12, 100 µg/ml. (FIG. 10D) Detection of heme transfer from hemoglobin (Hb) to HeSP2. Hemoglobin (Hb), Apo-HeSP2, and mixtures of Hb and Apo-HeSP2 were analyzed on native PAGE and stained for protein and heme, respectively. Lane 1, 20 µM Hb; lane 2, 200 µM HeSP2; lane 3, 200 µM HeSP2+200 µM Heme; lane 4, 20 µM Hb+20 µM HeSP2; lane 5, 20 µM Hb+50 µM HeSP2; lane 6, 20 µM Hb+100 µM HeSP2; lane 7, 20 µM Hb+200 µM HeSP2.

FIGS. 11A-B. The effects of HeSPs on NSCLC cell proliferation and survival. (FIG. 11A) HeSPs inhibit NSCLC cell proliferation and addition of heme largely reverses the inhibition. NSCLC cells were treated with 20 µM HeSPs in the presence or absence of 20 µM heme in medium. Data are plotted as mean ± SD. For statistical analysis, the levels in treated cells were compared to the levels in untreated cells with a Welch two-sample t-test. (**, $P<0.005$). (FIG. 11B) HeSP2 induces apoptosis in NSCLC cell line and addition of heme largely reverses this effect. The NSCLC cell line H1299 were treated with 20 µM HeSP2 in the presence or absence of 20 µM heme. Then cells were subjected to apoptosis assay using Annexin V-FITC and Propidium Iodide (PI) staining. The images of cells were captured with bright field microscopy (BF) or fluorescent microscopy with a GFP or Texas Red (for PI) filters. Scale bar, 100 µm.

FIGS. 12A-E. HeSP2 effectively suppresses the growth, oxygen consumption rates (OCRs), and ATP generation in subcutaneous NSCLC tumor xenografts. (FIG. 12A) Images showing resected tumors from mice implanted with subcutaneous xenografts (H1299-luc cells) treated with saline (control) or the indicated HeSP. Treatment started at 1.5 weeks after tumor implantation when authentic BLI signals were detected, and tumors were visible. Mice were sacrificed and tumors were resected when tumors in untreated mice reached about 1 cm³. (FIG. 12B) Average masses for control and HeSPs-treated tumors (n=5/group). (FIG. 12C) Average body masses of control and HeSPs-treated mice. (FIG. 12D) OCR measured in cells from control and HeSPs-treated tumors. (FIG. 12E) ATP levels measured in cells from control and HeSP-treated tumors. Data are plotted as mean ± SEM. For statistical analysis, the levels in HeSP-treated tumors were compared with the levels in control tumors with a Welch two-sample t-test (*, $P<0.05$; **, $P<0.005$).

FIGS. 13A-B. The effects of HeSPs on C. albicans cell proliferation and biofilm formation. (FIG. 13A) HeSPs inhibit C. albicans cell proliferation, and addition of heme largely reverses the inhibition. C. albicans cells were treated with 100 nM HeSPs in the presence or absence of 100 nM heme. (FIG. 13B) HeSPs inhibit C. albicans biofilm formation and addition of heme largely reverses the biofilm formation. Biofilm was formed in the presence or absence of 250 nM HeSPs with or without 250 nM heme. For statistical analysis, the levels in treated cells were compared to the levels in untreated cells with a Welch two-sample t-test. (**, $P<0.005$).

FIGS. 15A-C. (FIG. 15A) The levels of the rate-limiting heme biosynthetic enzyme ALAS1 are elevated in NSCLC cells. (FIG. 15B) The levels of heme transporter SLC46A1 are elevated in NSCLC cells. (FIG. 15C) The levels of heme degradation enzyme HMOX1 are elevated in NSCLC cells. Data are plotted as mean ± SD. For statistical analysis, the levels in tumorigenic cells were compared to the levels in non-tumorigenic cells with a Welch 2-sample t-test. *, p-value, 0.05, **, p-value <0.005.

FIGS. 16A-H. The levels of heme in subcellular organelles in NSCLC cell lines. (FIG. 16A) Heme levels in cytoplasm. (FIG. 16B) Heme levels in nucleus. (FIG. 16C) Heme levels in endoplasmic reticulum. (FIG. 16D) Heme levels in Golgi. (FIG. 16E) Heme levels in plasma membrane. (FIG. 16F) The levels of OXPHOS complex subunit cytochrome c (CYCS) are elevated in NSCLC cells. (FIG. 16G) The levels of OXPHOS complex subunit COX4I1 are elevated in NSCLC cells. (FIG. 16H) The levels of heme-containing enzyme cyclooxygenase (PTGS2) are elevated in NSCLC cells. Data are plotted as mean ± SD. For statistical analysis, the levels in tumorigenic cells were compared to the levels in non-tumorigenic cells with a Welch 2-sample t-test. *, p-value, 0.05, **, p-value <0.005.

FIGS. 17A-B. (FIG. 17A) NSCLC cell lines exhibit a varying degree of migration capabilities. (FIG. 17B) NSCLC cell lines exhibit a varying degree of invasion capabilities. The images shown are cells that had migrated across Transwell inserts (in FIG. 17A) or had crossed invasion chambers coated with Corning Matrigel matrix and passed Transwell inserts (in FIG. 17B). At least three independent experiments were carried out for every condition. Data are plotted as mean ± SD. For statistical analysis, the levels in NSCLC cells were compared to the levels in HCC cells with a Welch 2-sample t-test.*, p-value, 0.05, **, p-value <0.005.

FIGS. 18A-E. Proteins and enzymes relating to heme and mitochondrial functions are upregulated in human NSCLC tissues relative to control normal tissues. The examined proteins and enzymes include the rate-limiting heme synthetic enzyme ALAS1 (FIG. 18A), the heme transporter SLC48A1 (FIG. 18B), the hemoprotein OXPHOS subunit cytochrome c (CYCS) (FIG. 18C), hemoprotein PTGS2 (FIG. 18D), and the regulator promoting mitochondrial biogenesis TFAM (FIG. 18E). Shown are the representative Montages and 10× images of control and NSCLC tumor tissue sections stained with DAPI or antibodies against the indicated proteins. The yellow rectangles in Montages denote the regions shown in 10× images. Scale bar: montage, 1 mm; 10×, 20 µm. Protein levels were quantified with cellSens dimension software (Olympus). The values shown in the graphs are averages of signals quantified from six control and NSCLC independent tissue slides, respectively. Signals were calculated as described in Methods. Data are plotted as mean ± SD. For statistical analysis, the levels in treated tumors were compared to the levels in untreated tumors with a Welch 2-sample t-test. **, p-value <0.005.

FIGS. 19A-G. (FIG. 19A) The quantified luminescence signals representing tumor volumes from mice bearing orthotopic H1299 tumor xenografts treated with saline (control), and SA (50 mg/kg, I.V.) every 3 days (n=6/group). Treatments started 4 days after cell implantation. Data are plotted as mean ± SD. For statistical analysis, the levels in treated tumors were compared to the levels in untreated tumors with a Welch 2-sample t-test. The difference between control and SA was not statistically significant. (FIG. 19B) The sequences of Y. pestis HasA (SEQ ID NO: 15) and HSPs. The changed amino acid residues are indicated. (FIG. 19C) HSP1 and HSP2 bind to heme beads. CA (carbonic anhydrase) serves as the negative control while BSA serves as the positive control. These were used and described previously by Lal et al., Nucleic Acids Res, 46: 215-228 (2018). (FIG. 19D) HSP2 remains in the medium even after prolonged incubation with NSCLC cells. H1299 NSCLC cells were incubated with 40 μM HSP2 in the medium for the indicated time periods. Then, the proteins in 5 μl medium was analyzed on SDS-PAGE gels. Medium and HSP2 are usually refreshed after 3 days. Shown in the same gel are samples from RPMI medium (RPMI), RPMI medium with HSP2, and RPMI medium+serum. (FIG. 19E) Quantified levels of HSP2 in the medium relative to the major serum protein albumin. For statistical analysis, the levels in 1-72 hours of incubation were compared to the levels in 0 hour of incubation with a Welch 2-sample t-test. The variations are not statistically significant. (FIG. 19F) The DIC and fluorescent images of cells incubated with ZnPP or ZnPP+HSP2. H1299 NSCLC cells were incubated with 40 μM ZnPP or 40 μM ZnPP+HSP2 for 12 hours. Cells were washed to reduce background fluorescence from the medium before imaging. DIC and fluorescent (from ZnPP) images of the cells were taken and shown here. ZnPP bound with HSP2 did not enter the cells. (FIG. 19G) ZnPP in the absence of HSP2 entered NSCLC cells and co-localized with mitotracker green.

FIGS. 20A-D. HSPs inhibit NSCLC cell proliferation in a dose-dependent manner. (FIG. 20A) The same doses of HSP1 and HSP2 that affect NSCLC cell lines (FIGS. 20B-D) do not affect significantly the HBEC30KT cell lines representing normal lung epithelial cells. Data from representative NSCLC cell lines HCC4017 (FIG. 20B), H1299 (FIG. 20C), and A549 (FIG. 20D) are shown. For statistical analysis, the levels in treated cells were compared to the levels in untreated cells with a Welch 2-sample t-test. **, p-value <0.005.

FIGS. 21A-I. HSPs inhibit tumorigenic functions in A549 NSCLC cells. (FIG. 21A) HSPs inhibit migration in A549 NSCLC cells. (FIG. 21B) HSPs inhibit invasion in A549 NSCLC cells. The potent inhibitor of heme synthesis, succinyl acetone (SA), is shown for comparison. Addition of 10 μM heme largely reversed the effects of SA and HSPs. The images shown are cells that had migrated across Transwell inserts (in FIG. 21A) or had crossed invasion chambers coated with Corning Matrigel matrix and also passed Transwell inserts (in FIG. 21B). Data are plotted as mean ± SD. For statistical analysis, the levels in treated cells were compared to the levels in untreated cells with a Welch 2-sample t-test.*, p-value, 0.05, , p-value <0.005. For heme add-back experiments, the levels in cells treated with heme and SA or HSPs were compared to the levels in cells treated with only SA or HSPs. [], p-value <0.005. The effects SA, HSPs, heme oxygenase inhibitors, and iron chelator DFX on NSCLC cell colony formation are shown in FIGS. 21C-G. (FIG. 21C) The effect of SA on colony formation in A549 cells. (FIG. 21D) The effect of HSP1 on colony formation in A549 cells. (FIG. 21E) The effect of HSP2 on colony formation in A549 cells. (FIG. 21F) The effects of heme oxygenase inhibitor SnPP and ZnPP on colony formation in A549 cells. (FIG. 21G) The effect of DFX on colony formation in A549 cells. (FIG. 21H) Comparison of the effects of HSP2 and DFX treatments on the levels of transferrin receptor TFRC. (FIG. 21I) Comparison of the effects of HSP2 and DFX treatments on the levels of ferroportin SLC40A1. In H & I, data from Western blotting analysis of proteins prepared from NSCLC cells treated with HSP2 or DFX for 6 days were shown. For statistical analysis, the levels in treated cells were compared to the levels in untreated cells (Control) with a Welch 2—sample t-test. **, p-value <0.005.

FIGS. 22A-J. The effect of HSP2 on the growth and progression of H1299 NSCLC lung tumor xenografts and on blood and liver functions in mice. (FIG. 22A) The quantified luminescence signals representing tumor volumes. Treatment started at week 3 when tumors have grown significantly and BLI signals were about $5\times10^7$ photons/seconds. Data are plotted as mean ± SD. For statistical analysis, the levels in treated tumors were compared to the levels in untreated tumors with a Welch 2-sample t-test. *, p-value <0.05. (FIG. 22B) Representative H&E images of control tumors and tumors treated with HSP2 or control saline. Tumors are marked with light blue outlines. Scale bar: 2 mm. (FIG. 22C) Average red blood cell count in mice bearing orthotopic lung tumor xenografts treated with or without HSP2. (FIG. 22D) Average hemoglobin levels in mice bearing orthotopic lung tumor xenografts treated with or without HSP2. (FIG. 22E) Average serum ALT (alanine transaminase) levels in mice bearing orthotopic lung tumor xenografts treated with or without HSP2. (FIG. 22F) Western blots showing the levels of ALAS1 in H1299 cells bearing the control or overexpression vector for ALAS1. (FIG. 22G) Western blots showing the levels of SLC48A1 in H1299 cells bearing the control or overexpression vector for ALAS1. (FIG. 22H) Oxygen consumption rates are increased in cells overexpressing ALAS1 or SLC48A1. (FIG. 22I) overexpression of ALAS1 or SLC48A1 promotes colony formation by H1299 NSCLC cells. For statistical analysis, the levels in cells overexpressing ALAS1 or SLC48A1 were compared to the levels in control cells with a Welch 2-sample t-test. **, p-value <0.005. (FIG. 22J) The levels of heme synthesis in H1299 cells cultured in normal medium and heme-depleted medium (H dep), respectively. The level of heme synthesis in heme-depleted medium presumably represents the total cellular heme levels needed for the cells. The data show that de novo heme synthesis accounts for approximately 68% of total cellular heme levels in H1299 cells, indicating that heme uptake accounts for 32%. Data are plotted as mean ± SD. For statistical analysis, the levels in heme-depleted medium were compared to the levels in normal medium with a Welch 2-sample t-test.*, p-value, 0.05, **, p-value <0.005.

FIGS. 23A-B. HasA$_{yp}$ does not suppress NSCLC tumor growth significantly. (FIG. 23A) Images showing resected tumors from mice implanted with subcutaneous xenografts (H1299-luc cells) treated with saline (control) or HasA$_{yp}$. (FIG. 23B) Average masses for control and HasA$_{yp}$-treated tumors (n=4/group).

FIGS. 24A-B. (FIG. 24A) The transfer of heme from hemoglobin (Hb) to HeSP2 is instantaneous. Hemoglobin (Hb), Apo-HeSP2, and mixtures of Hb and Apo-HeSP2 were incubated for the indicated times and then analyzed on native PAGE, followed by staining for protein and heme, respectively. Lane 1, 20 μM Hb; lane 2, 200 μM HeSP2; lane 3, 200 μM HeSP2+200 μM Heme; lanes 4-9, 20 μM Hb+200 μM HeSP2 incubated for 1, 2, 5, 10, 20, and 30 minutes. (FIG. 24B) Detection of heme transfer from hemoglobin (Hb) to HasA$_{yp}$. Hemoglobin (Hb), apo-HasA$_{yp}$, and mixtures of Hb and HasA$_{yp}$ were analyzed on native PAGE and stained for protein and heme, respectively. Lane 1, 20 μM Hb; lane 2, 200 μM HasA$_{yp}$; lane 3, 200 μM HasA$_{yp}$+200 μM Heme; lane 4, 20 μM Hb+20 μM HasA$_{yp}$; lane 5, 20 μM Hb+50 μM HasA$_{yp}$; lane 6, 20 μM Hb+100 μM HasA$_{yp}$; lane 7, 20 μM Hb+200 μM HasA$_{yp}$.

FIG. 25. The pull-down of various HeSPs by heme agarose beads. Five hundred picomoles of indicated HeSPs were incubated with heme-agarose beads. The input (In) proteins, bound (Bu) and unbound proteins (UnB) were analyzed by SDS-PAGE and shown.

FIGS. 26A-F. The effects of HeSPs on heme absorption spectra: line 1: 5 μM heme, line 2: 5 μM heme+10 μM HeSP, line 3: 10 μM HeSP.

FIGS. 27A-F. Elution profiles of heme-HeSP mixtures on Sephadex-G50 columns: line1: 0.25 mM heme+0.25 mM HeSP (protein absorption at 280 nm), line2: 0.25 mM heme+0.25 mM HeSP (heme absorption at 400 nm), line 3: 0.25 mM (heme absorption at 400 nm).

FIGS. 28A-B. (FIG. 28A) The effects of HeSPs on heme uptake in H1299 NSCLC cells. Cells were treated with 60 μmol/L ZnPP in the presence or the absence of 40 μmol/L HeSPs. Data are plotted as mean ± SD. For statistical analysis, the levels in treated cells were compared with the levels in untreated cells with a Welch two-sample t-test (*, $P<0.05$; **, $P<0.005$). (FIG. 28B) HeSP2 remains stable in the medium during prolonged incubation with NSCLC cells. H1299 NSCLC cells were incubated with 40 μM HeSP2 in the medium for the indicated time periods. Then, the proteins in 5 μl medium were analyzed on SDS-PAGE gels. Shown in the same gel are samples from RPMI medium (RPMI), RPMI medium with HeSP2 and RPMI medium+ serum. Quantified levels of HeSP2 in the medium relative to the major serum protein albumin. For statistical analysis, the levels in 1-48 hours of incubation were compared to the levels in 0 hour of incubation with a Welch two-sample t-test. The variations are not statistically significant.

FIGS. 29A-G. HeSPs inhibit NSCLC cell proliferation in a dose-dependent manner. H1299 NSCLC cells were treated with various concentration of the following HeSPs: (FIG. 29A) HeSP2, (FIG. 29B) HeSP2H, (FIG. 29C) HeSP2C, (FIG. 29D) HeSP2del, (FIG. 29E) HeSP2pc, (FIG. 29F) HeSP2ec, and (FIG. 29G) HeSP2pf. For statistical analysis, the levels in treated cells were compared to the levels in untreated cells with a Welch two-sample t-test. (*, $P<0.05$; **, $P<0.005$).

FIGS. 31A-D. HeSPs do not cause significant toxic effects on mouse blood and liver. (FIG. 31A) Average red blood cell counts in mice bearing subcutaneous lung tumor xenografts treated with or without HeSPs. (FIG. 32B) Average hemoglobin levels in mice bearing subcutaneous lung tumor xenografts treated with or without HeSPs. (FIG. 33C) Average serum ALT (alanine transaminase) levels in mice bearing subcutaneous lung tumor xenografts treated with or without HeSPs. (FIG. 34D) Relative liver ATP levels in live cells from mice bearing subcutaneous lung tumor xenografts treated with or without HeSPs.

FIG. 32. HeSPs inhibit heme uptake in Candida albicans. C. albicans cells were treated with 60 μmol/L ZnPP in the presence or the absence of 40 μmol/L HeSPs. Data are plotted as mean ± SD. For statistical analysis, the levels in treated cells were compared with the levels in untreated cells with a Welch two-sample t-test (*, $P<0.05$; **, $P<0.005$).

DETAILED DESCRIPTION

Figure 1:
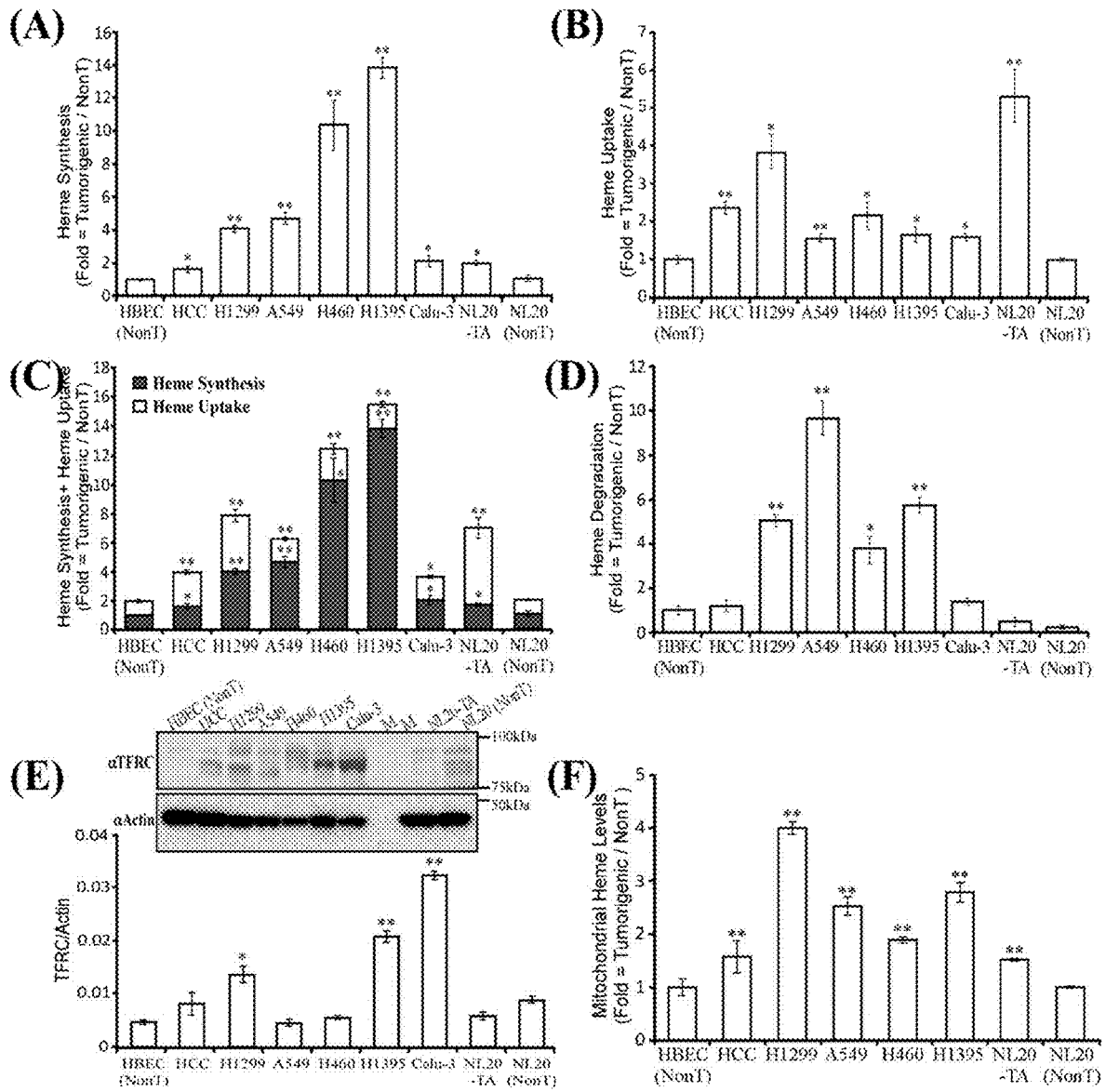
FIGS. 1A-F.

The inventor hypothesized that lowering heme supply via heme sequestration is likely to be a useful strategy to manage and treat an array of pathological conditions, including cancer. In this report, she describes studies to take advantage of bacterial hemophore HasA (Wandersman and Delepelaire, 2012; Huang and Wilks, 2017) to sequester heme and make it unavailable for tumor cells and perhaps pathogenic fungi, because HasA delivers heme only to bacteria, not host cells. While wild-type HasA is efficient for scavenging heme and delivering heme to bacteria, it may not have the best properties for heme sequestration. She reasoned that certain mutant HasA proteins that retain high heme-binding affinity but having altered properties in interaction with heme may be more effective in heme sequestration. Based on the sequence of HasA proteins from Yersinia pestis and other bacteria, a series of heme-sequestering proteins (HeSPs) were generated and verified their interaction with heme. Further, it was found that these HeSPs can strongly suppress the growth of lung tumors in human xenograft tumor models and inhibit the proliferation and biofilm formation in Candida albicans. These data show that heme sequestration can be an effective strategy for anti-cancer and anti-microbial therapies. These and other aspects of the disclosure are set out below.

I. HEME BINDING PROTEINS

Free iron is limited in vertebrate hosts, thus an alternative to siderophores has been developed by pathogenic bacteria to access host iron bound in protein complexes. Heme binding protein A, or HasA, is a secreted hemophore that has the ability to obtain iron from hemoglobin. Once bound to HasA, the heme is shuttled to the receptor HasR, which releases the heme into the bacterium. A variety of different microorganisms express a HasA molecule, including Yersinia pestis, Erwinia carotovora, Pectobacterium carotvorum and Pseudomonas fluorescens.

A. Engineered Heme Sequestering Peptides

The present inventor has designed heme sequestering peptides (HeSP's) to improve their utility as therapeutic agents. For example, the inventor has designed HeSP's using structural comparisons of known HasA's and a computational algorithm based on coevolution to identify residues whose mutations may alter but not disrupt heme-binding properties, such as sequence, bold residues represent non-*Y. pestis* sequences and lined-through residues are deleted as compared to native *Y. pestis* HasA sequence.

```
HasA from Yersinia pestis
                                        (SEQ ID NO: 1)
MSTTIQYNSNYADYSISSYLREWANNFGDIDQAPAETKDRGSFSGSSTLF

SGTQYAIGSSHSNPEGMIAEGDLKYSFMPQHTFHGQIDTLQFGKDLATNA

GGPSAGKHLEKIDITFNELDLSGEFDSGKSMTENHQGDMHKSVRGLMKGN

PDPMLEVMKAKGINVDTAFKDLSIASQYPDSGYMSDAPMVDTVGVVDCHD

MLLAA*

HasAyp
                                        (SEQ ID NO: 2)
MSTTIQYNSNYADYSISSYLREWANNFGDIDQAPAETKDRGSFSGSSTLF

SGTQYAIGSSHSNPEGMIAEGDLKYSFMPQHTFHGQIDTLQFGKDLATNA

GGPSAGKHLEKIDITFNELDLSGEFDSGKSMTENHQGDMHKSVRGLMKGN

PDPMLEVMKAKGINVDTAFKDLSIASQYPDSGYMSDAPMVDTV*

HeSP1
                                        (SEQ ID NO: 3)
MSTTIQYNSNYADYSISSYLREWANNFGDIDHAPAETKDRGSFSGSSTLF

SGTQYAIGSSHSNPEGMIAEGDLKYSFMPQHTFHGQIDTLQFGKDLATNA

GGPSAGKHLEKIDITFNELDLSGEFDSGKSMTENHQGDMHKSVRGLMKGN

PDPMLEVMKAKGINVDTAFKDLSIASQYPDSGYMSDAPMVDTV*
(Q in HasAyp is changed to H in HeSPs)

HeSP2
                                        (SEQ ID NO: 4)
MSTTIQYNSNYADYSISSYLREWANNFGDIDHAPAETKDRGSFSGSSTLF

SGTQYAIGSSHSNPEGMIAEGDLKMSFMPQHTFHGQIDTLQFGKDLATNA

GGPSAGKHLEKIDITFNELDLSGEFDSGKSMTENHQGDMHKSVRGLMKGN

PDPMLEVMKAKGINVDTAFKDLSIASQYPDSGYMSDAPMVDTV*

HeSP2H
                                        (SEQ ID NO: 5)
MSTTIQYNSNYADYSISSYLREWANNFGDIDHAPAETKDRGSFSGSSTLF

SGTQYAIGSSHSNPEGMIAEGDLKHSFMPQHTFHGQIDTLQFGKDLATNA

GGPSAGKHLEKIDITFNELDLSGEFDSGKSMTENHQGDMHKSVRGLMKGN

PDPMLEVMKAKGINVDTAFKDLSIASQYPDSGYMSDAPMVDTV*

HeSP2C
                                        (SEQ ID NO: 6)
MSTTIQYNSNYADYSISSYLREWANNFGDIDHAPAETKDRGSFSGSSTLF

SGTQYAIGSSHSNPEGMIAEGDLKCSFMPQHTFHGQIDTLQFGKDLATNA

GGPSAGKHLEKIDITFNELDLSGEFDSGKSMTENHQGDMHKSVRGLMKGN

PDPMLEVMKAKGINVDTAFKDLSIASQYPDSGYMSDAPMVDTV*

HeSP2del
                                        (SEQ ID NO: 7)
MSTTIQYNSNYADYSISSYLREWANNFGDIDHAPAETKDRGSFSGSSTLF

SGTQYAIGSSHSNPEGMIAEGDLKMSFMPQHTFHGQIDTLQFGKDLATNA

GGPSAGKHLEKIDITFNELDLSGEFDSGKSMATENHQGDMHKSVRGLMKG

NPDPMLEVMKAKGINVDTAFKDLSIASQYPDSGYMSDAPMVDTV*

HeSP2ec
Fusion protein of Y. pestis HeSP2 1-128 aa +
wild-type Erwinia carotovora HasA 133-196 aa
                                        (SEQ ID NO: 8)
MSTTIQYNSNYADYSISSYLREWANNFGDIDHAPAETKDRGSFSGSSTLF

SGTQYAIGSSHSNPEGMIAEGDLKMSFMPQHTFHGQIDTLQFGKDLATNA

GGPSAGKHLEKIDITFNELDLSGEFDSGLTVSDRGVVHDVIYGLMGGQVQ

PLLDALTNAGIDINASLDSLSFATATSDAALSADTVVDVVGV*

HeSP2pc
Fusion protein of Y. pestis HeSP2 1-136 aa + wild-
type Pectobacterium carotovorum HasA 139-196 aa
                                        (SEQ ID NO: 9)
MSTTIQYNSNYADYSISSYLREWANNFGDIDHAPAETKDRGSFSGSSTLF

SGTQYAIGSSHSNPEGMIAEGDLKMSFMPQHTFHGQIDTLQFGKDLATNA

GGPSAGKHLEKIDITFNELDLSGEFDSGKSMTENHQGVVHDVIYGLMSGQ

VQPLLDALTNAGIDINASLDSLSFATATSDAALSADTVVDVVGV*

HeSP2pf
Fusion protein of Y. pestis HeSP2 1-101 aa + wild-
type Pectobacterium fluorenscens HasA 104-194 aa
                                        (SEQ ID NO: 10)
MSTTIQYNSNYADYSISSYLREWANNFGDIDHAPAETKDRGSFSGSSTLF

SGTQYAIGSSHSNPEGMIAEGDLKMSFMPQHTFHGQIDTLQFGKDLATNA

GSNYNLVSQEVSFTNLGLNSLKEEGRAGEVHKVVYGLMSGDSSALAGEID

ALLKAIDPSLSVNSTFDDLAAAGVAHVNPAAAAAADVGLVGV*
```

C. Synthesis and Purification

Because of the size of the HeSP's, recombinant expression is the preferred method for synthesis. A variety of commercially available vectors and expression systems can be employed to generate the HeSP's including those designed for mammalian cells, insect (*Spodoptera*; Baculovirus delivered) cells and bacterial cells. A preferred method is the *E. coli* pET11a expression system. Baculovirus system may be used in future to avoid endotoxin contamination in human trials.

In certain embodiments, the HeSP's are purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95%, about 98%, about 99% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques. In purifying a protein, it may be desirable to extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide will be known to those of skill in the art in light of the present disclosure. These include, for example, determining the specific activity of an active fraction, or assessing the amount of polypeptide within a fraction by SDS/PAGE analysis. Another method for assessing the purity of a fraction is to calculate the specific activity of the fraction, to compare it to the specific activity of the initial extract and to thus calculate the degree of purity. The actual units used to represent the amount of activity will, of course, be dependent upon the particular assay technique chosen to follow the purification and whether or not the expressed protein or peptide exhibits a detectable activity. It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

II. DISEASE STATES AND TREATMENT THEREOF

A. Cancer

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the compounds of the present disclosure may be used to lead to decreased cell counts and as such can potentially be used to treat a variety of types of cancer lines. In some aspects, it is anticipated that the compounds of the present disclosure may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; in situ pulmonary adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

B. Microbial Disease

In another aspect, the disclosure relates to certain infectious diseases. Infection is the invasion of an organism's body tissues by disease-causing agents, their multiplication, and the reaction of host tissues to the infectious agents and the toxins they produce. Infectious disease, also known as transmissible disease or communicable disease, is illness resulting from an infection. Microbial infections are those caused by microbes, i.e., viruses, bacteria, fungi and certain unicellular parasitic organisms. Ascomycota, including yeasts such as *Candida*, are of particular relevance. *Cryptococcus neoformans, Candida glabrata* and *Paracoccidioides lutzii* also are known to use heme.

C. Combination Therapy

It is envisioned that the compounds of the present disclosure may be used in combination therapies with one or more other therapies or a compound which mitigates one or more of the side effects experienced by the patient. It is common in the field of medicine to combine therapeutic modalities. The following is a general discussion of therapies that may be used in conjunction with the therapies of the present disclosure.

For example, to treat cancers or other disease using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the compounds of the present disclosure may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are also contemplated. The following is a general discussion of cancer therapies that may be used combination with the compounds of the present disclosure.

1. Cancer

Chemotherapy. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin $\gamma_1$ and calicheamicin $\omega_1$; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomycins, actinomycin, authrarnycin, azaserine, bleomycins, cactinomycin, carubicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozotocin, tubercidin, ubenimex, zinostatin, or zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabine, navelbine, farnesyl-protein tansferase inhibitors, transplatinum, 5-fluorouracil, vincristine, vinblastine and methotrexate and pharmaceutically acceptable salts, acids or derivatives of any of the above.

Radiotherapy. Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

Immunotherapy. In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis*, *Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

Checkpoint inhibitor therapy is another valuable therapy for combination with the compounds of the present disclosure. Checkpoint therapy targets immune checkpoints, key regulators of the immune system that when stimulated can dampen the immune response to an immunologic stimulus. Some cancers can protect themselves from attack by stimulating immune checkpoint targets. Checkpoint therapy can block inhibitory checkpoints, restoring immune system function. The first anti-cancer drug targeting an immune checkpoint was ipilimumab, a CTLA4 blocker approved in the United States in 2011. Currently approved checkpoint inhibitors target the molecules CTLA4, PD-1, and PD-L1. PD-1 is the transmembrane programmed cell death 1 protein (also called PDCD1 and CD279), which interacts with PD-L1 (PD-1 ligand 1, or CD274). PD-L1 on the cell surface binds to PD1 on an immune cell surface, which inhibits immune cell activity. Among PD-L1 functions is a key regulatory role on T cell activities. It appears that (cancer-mediated) upregulation of PD-L1 on the cell surface may inhibit T cells that might otherwise attack. Antibodies that bind to either PD-1 or PD-L1 and therefore block the interaction may allow the T-cells to attack the tumor.

Surgery. Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believed to be particularly efficacious in reducing the reoccurrence of the tumor. Additionally, the compounds of the present disclosure can also be used in a neoadjuvant setting.

Other Agents. It is contemplated that other agents may be used with the present disclosure. These additional agents include immunomodulatory agents, agents that affect the upregulation of cell surface receptors and gap junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increased intercellular signaling by elevating the number of gap junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 41.1° C.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA's Division of Biological Standards and Quality Control of the Office of Compliance and Biologics Quality.

2. Anti-Fungal Agents

Combination therapies with the HeSP's of the present disclosure and known anti-fungal agents are also contemplated. Such agents include fluconazole (FLC), itraconazole (ITC), ketoconazole (KTC), posaconazole (POS), and voriconazole (VOR), ketoconazolev (KTC), undecylic acid (undecanoic acid), nystatin (NYS), naftifine (NAF), tolnaftate, amorolfine, butenafine (BTF), miconazole (MCZ), econazole, ciclopirox, oxiconazole, sertaconazole, efinaconazole, clotrimazole (CLO), sulconazole, tioconazole, tavaborole, terbinafine (TER), mancozeb, tricyclazole, carbendazim, hexaconazole, propineb, metalaxyl, benomyl (BEN) (Methyl 1-(butylcarbamoyl)-2-benzimidazolecarbamate), difenoconazole, propiconazole (PCZ), kitazin, tebuconazole (TER), tridemorph (TDM), and metconazole (MET).

III. FORMULATION AND ADMINISTRATION

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

IV. NON-THERAPEUTIC APPLICATIONS

A. Diagnostic

Zinc protoporphyrin (ZnPP) is a compound found in red blood cells when heme production is inhibited by lead and/or by lack of iron. Instead of incorporating a ferrous ion, to form heme, protoporphyrin IX, the immediate precursor of heme, incorporates a zinc ion, forming ZPP. The reaction to insert a ferrous ion into protoporphyrin IX is catalyzed by the enzyme ferrochelatase. Measurement of zinc protoporphyrin in red cells has been used as a screening test for lead poisoning and for iron deficiency. There are a number of specific clinical situations in which this measurement has been found to be useful.

Zinc protoporphyrin levels can be elevated as the result of a number of conditions, for instance lead poisoning, iron deficiency, sickle cell anemia, sideroblastic anemia, anemia of chronic disease, vanadium exposure, erythropoietic protoporphyria, and varying types of cancer. Because zinc proptoporphyrin has fluorescence, the inventor tested its binding to HeSP's. When bound, the fluorescence intensity is increased by about a hundred-fold. Thus, ZnPP bound with HeSP may be used to detect tumors in in vivo imaging or in biological samples for any of the other diseases described above.

B. Biofilm Treatment

Biofilms may form on a wide variety of surfaces, including living tissues, indwelling medical devices, industrial or potable water system piping, or natural aquatic systems. HeSP's can be used as cleaning agents, emulsifiers, dispersants, surfactants, or antifungal, antibiofilm, or antifouling agents to remove disease-causing organisms from external surfaces, including human and animal tissue such as skin and wounds. They can be used in different products such as soaps, detergents, deodorizers, stain removers, health and skincare products, cosmetics, antiseptics, and household, industrial, institutional, and clinical cleaners. They can also be used to remove algae, mold, or slime. HeSP's can be used alone, or in combination with other antimicrobial or antifungal agents.

A spectrum of indwelling medical devices (e.g., ocular lenses, dental implants, central venous catheters and needleless connectors, endotracheal tubes, intrauterine devices, mechanical heart valves, coronary stents, vascular bypass grafts, pacemakers, peritoneal dialysis catheters, prosthetic joints, central nervous system shunts, tympanostomy tubes, urinary catheters, and voice prostheses) or other devices used in the health-care environment have been shown to harbor biofilms, resulting in measurable rates of device-associated infections.

The HeSP's can be used on the surface of or within medical devices to provide long term protection against microbial colonization and reduce the incidence of device-related infections. These substances can also be incorporated as an anti-biofilm forming agent, in combination with an anti-fungal, into coatings for indwelling medical devices, instruments, and other clinical surfaces. Coatings will sufficiently kill or inhibit the initial colonizing organism and prevent device-related infection as long as the substance is presented in an inhibitory concentration at the device-microbe interface.

The HeSP's, either administered alone or as part of a coating or medical device, can reduce or prevent biofilms. In certain embodiments, biofilms are reduced by about 1.0 log, about 1.5 logs, about 2.0 logs, about 2.5 logs, about 3.0 logs, about 3.5 logs, about 4.0 logs, about 4.5 logs, or about 5.0 logs, or by any number bound by the range of about 1.0 to about 5.0 logs.

The medical devices which are amenable to coatings of the subject anti-biofilm substances generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings with the anti-biofilm substances. Such devices, for example bone and joint prosthesis, can be coated by cement mixture containing the subject anti-biofilm substances. During implant use, the anti-biofilm substances leach from the cement into the surrounding prosthesis surface environment.

Various methods can be employed to coat the surfaces of medical devices with the anti-biofilm substances. For example, one of the simplest methods would be to flush the surfaces of the device with a solution of the anti-biofilm substance. The flushing solution would normally be composed of sterile water or sterile normal saline solutions. Another method of coating the devices would be to first apply or adsorb to the surface of the medical device a layer of tridodecylmethyl ammonium chloride (TDMAC) surfactant followed by a coating layer of anti-biofilm substance. For example, a medical device having a polymeric surface, such as polyethylene, silastic elastomers, polytetrafluoroethylene or Darcon, can be soaked in a 5% by weight solution of TDMAC for 30 minutes at room temperature, air dried, and rinsed in water to remove excess TDMAC. Alternatively, TDMAC precoated catheters are commercially available; for example, arterial catheters coated with TDMAC are available from Cook Critical Care, Bloomington, Ind. The device carrying the absorbed TDMAC surfactant coated can then be incubated in a solution of the anti-biofilm substance for one hour or so, washed in sterile water to remove unbound anti-biofilm substance and stored in a sterile package until ready for implantation. A further method useful to coat the surface of medical devices with the subject antibiotic combinations involves first coating the selected surfaces with benzalkonium chloride followed by ionic bonding of the anti-biofilm substance composition. Alternative methods and reagents provided in U.S. Pat. Nos. 4,107,121, 4,442,133, 4,678,660 and 4,749,585, 4,895,566, 4,917,686, 4,952,419, and 5,013,30, can be used to coat devices with the anti-biofilm substances disclosed herein.

The HeSP's can be directly incorporated into the polymeric matrix of the medical device at the polymer synthesis stage or at the device manufacture stage. An HeSP can also be covalently attached to the medical device polymer.

Biofilms in industrial systems cause severe clogging, contamination, corrosion, scale, slime, and biodeterioration. Microbial contamination of the water distribution systems can occur if biofilms are sloughed off naturally or removed by treatment. Biofilms in drinking water piping systems are also common. This results in decreased water quality and increased treatment costs and health risks. Biofilms in pipes, fixtures and containers carrying water or other liquids cause reduced flow and increased resistance to flow. Formation of biofilms on probes, sensors, screens and filters results in reduced efficiency. Microbial films that grow on the walls of heat exchanger tubes create additional heat transfer and fluid flow resistances. Formation of biofilms on ship hulls leads to biofouling resulting in increased fuel consumption and cleaning costs. The food industry is also affected by the contamination caused by these films which adhere easily to the walls of food processing equipment, and on the surface of food itself. Biofilms in cooling towers results in reduced performance, degradation of material and also provides a reservoir for pathogens. Building materials such as stone, bricks and concrete or clay based roof tiles, mortars and especially all new materials for insulation and damming of humidity often contain organic compounds and are very susceptible to growth of sub-aerial biofilms creating an anesthetic biopatina and reducing durability. Chemical and physical biodeteriorative forces, phenomena and processes further create damage on old and new buildings. Depending on the environmental conditions water retention and penetration the surface biofilms may transform into networks going deeper into the material. Biocide impregnation of new materials and biocide treatments of monuments create health and environmental hazards. Biofilm on surfaces also captures pollutants, noxious particles, elements, spores, and other contaminants.

Fouling is an undesirable growth of biological material on a surface immersed in water. Fouling usually starts with adhering and spreading of populations of microbes over surfaces that are in contact with water. Such structures may include: pilings, marine markers, undersea conveyances like cabling and pipes, fishing nets, bulkheads, cooling towers, and any device or structure that operates submerged.

An HeSP can be incorporated into marine coatings to limit undesirable marine fouling. The anti-fouling coatings of this disclosure offer significant advantages over previous attempts to solve marine fouling problems. The coatings disclosed herein can be formulated so as not to contain toxic materials (such as heavy metals), and still retain their efficacy. This avoids the environmental concerns associated with the use of heavy metal biocides.

In some embodiments, the methods of the present disclosure comprise applying to a surface a composition comprising an HeSP effective to inhibit the growth of a biofilm on the surface. In some embodiments, the surface is an indwelling medical device. In some embodiments, the surface is a surface exposed to water. In some embodiments, the surface is a piece of industrial equipment.

V. EXAMPLES

The following Examples are intended to illustrate the above disclosure and should not be construed as to narrow its scope. One skilled in the art will readily recognize that the Examples suggest many other ways in which the disclosure could be practiced. It should be understood that numerous variations and modifications may be made while remaining within the scope of the disclosure. The disclosure may be further understood by the following non-limiting examples.

Example 1

Materials and Methods

Reagents. Succinyl acetone was purchased from Sigma-Aldrich (Catalog #D1415-1G). Heme was purchased from Frontier Scientific Inc. (Catalog #H651-9). Zinc (II) protoporphyrin IX (Catalog #Zn 625-9) was purchased from Frontier Scientific Inc. Tin (IV) protoporphyrin was purchased from Porphyrin Products Inc (Catalog #Sn749-9). Deferoxamine mesylate was purchased from Sigma-Aldrich (Cat #D9533-1G). Ferric chloride was purchased from Sigma-Aldrich (Catalog #157740-100G). D-Luciferin and the Opal 4 color IHC kit were purchased from PerkinElmer (USA). [4-$^{14}$C]5-aminolevulinic acid was custom synthesized by PerkinElmer. Antibodies were purchased from Santa Cruz Biotechnology, Cell Signaling Technology, Novus Biologicals, and abcam. HSP1 and HSP2 were purified with the pET11a expression system. The pET11a expression vector for *Y. pestis* HasA residues 1-193 was kindly provided by Dr. Mario Rivera (University of Kansas) (23). HSP1 contains the Q32H mutation, and HSP2 contains Q32H Y75M double mutations. The mutations were generated with the QuikChange II Site-Directed Mutagenesis Kit (Agilent Technologies). The double mutations were generated with the expression vector for the Q32H mutation. All DNA clones were confirmed by sequencing (Eurofins Genomics LLC). HSP1 and HSP2 were purified with a Q-Sepharose Fast Flow column (GE Healthcare), followed by size exclusion chromatography, as described (23). The reporter plasmids for measuring subcellular heme levels were kindly provided by Dr. Iqbal Hamza (24).

Cell culture and analyses of tumorigenic functions. HBEC30KT (RRID:CVCL_AS83) and HCC4017 (RRID:CVCL_V579) cell lines representing normal, non-tumorigenic and NSCLC cells from the same patient (25, 26), respectively, were provided by Dr. John Minna's lab (UT Southwestern Medical Center) as a gift. They were developed from the same patient and were maintained in ACL4 medium supplemented with 2% heat-inactivated, fetal bovine serum (25). A pair of bronchial epithelial cell lines consisting of normal, non-tumorigenic cell line NL20 (ATCC Cat #CRL-2503, RRID:CVCL_3756) and tumorigenic cell line NL20-TA (ATCC Cat #CRL-2504, RRID:CVCL_3757), was purchased from American Type Culture Collection (ATCC). NL20 and NL20-TA cell lines were maintained in Ham's F12 medium with 1.5 g/L sodium bicarbonate, 2.7 g/L glucose, 2.0 mM L-glutamine, 0.1 mM nonessential amino acids, 0.005 mg/ml insulin, 10 ng/ml epidermal growth factor, 0.001 mg/ml transferrin, 500 ng/ml hydrocortisone and 4% fetal bovine serum. All other NSCLC cell lines, H1299 (ATCC Cat #CRL-5803, RRID:CVCL_0060), A549 (ATCC Cat #CRM-CCL-185, RRID:CVCL_0023), H460 (ATCC Cat #HTB-177, RRID:CVCL_0459), Calu-3 (ATCC Cat #HTB-55, RRID:CVCL_0609), and H1395 (ATCC Cat #CRL-5868, RRID:CVCL_1467) were purchased from ATCC, maintained in RPMI medium, and supplemented with 5% heat-inactivated, fetal bovine serum. All experiments using cells were conducted between passages 3-5 from revival of the initial frozen stocks. experiments Cell lines expressing luciferase were generated by infection with lentiviral particles bearing the EF1a-Luciferase (firefly) gene (AMSBIO). Cell lines were authenticated by Genetica and were found to be 96% identical to the standard (authentication requires >80%). Cell lines were tested for *mycoplasma* using a MycoFluor™ *Mycoplasma* Detection Kit (Molecular Probes), and the results were negative.

For generation of stable overexpression lines overexpressing ALAS1 or SLC48A1, lentiviral vectors expressing ALAS1, SLC48A1, and eGFP (control vector) were purchased from Genecoepia. The expression vectors for ALAS1 and SLC48A1 also express eGFP, making them comparable with the control and easy for verification of positive clones. All vectors carry the neomycin selectable marker. Lentivirus particles were generated by co-transfecting 293T cells with packaging plasmids pMD2. G (addgene plasmid #12259, RRID:Addgene_12259) and psPAX2 (addgene plasmid #12260, RRID:Addgene_12260) and vector for ALAS1 or SLC48A1 using Lipofectamine 3000. pMD2. G and psPAX2 were gifts from Didier Trono. For generating stable overexpression cell lines, H1299 and A549 cells (70-80% confluent) were transduced with virus particles (2.8×10$^4$ units/well) in 48-well tissue culture plates. After series of passes and antibiotic selection stable clones were selected and verified for overexpression by Western blotting.

Cell proliferation was measured by detecting the luciferase activity in live cells and by using a hemocytometer. Cell migration and invasion assays were carried out with BD Falcon cell culture inserts (Corning Life Sciences) and the manufacturer's cell migration, chemotaxis, and invasion assay protocols. For the colony formation assay, 5000 NSCLC cells were seeded in every well in 6-well tissue culture plates in triplicates. Cells were treated with 0.5 mM succinyl acetone (Sigma Aldrich), 10 μM HSPs, 50 μM deferoxamine mesylate (DFX), 10 μM zinc (II) protoporphyrin IX, 10 μM tin (IV) protoporphyrin IX, or 50 μM ferric chloride for 6 days. For heme add-back experiments, 10 μM heme was included. Medium was changed every 3 days. After 6 days of treatment, cells were fixed with 70% ethanol and stained with 0.5% crystal violet. Images were acquired by using Carestream Gel Logic GL-112 imaging system.

Measurement of heme synthesis and uptake. Measurement of heme synthesis in cells was carried out exactly as described (27, 28). Briefly, 0.3 μC [4-$^{14}$C]-5-aminolevulinic acid (ALA) was added to each culture plate for 15 hours. Heme was subsequently extracted, and radiolabeled heme was quantified as described (29). For measuring heme uptake, a fluorescent analog of heme, zinc protoporphyrin IX (ZnPP), was used, as described previously (30, 31). Briefly, 10,000 NSCLC cells were seeded in 96-well plates. Cells were incubated for 3 hours with 60 μM ZnPP in the presence or the absence of 40 μM HSPs. Fluorescence intensity was measured with a Biotek Cytation 5 plate reader. Experiments were conducted in triplicates, and ZnPP uptake was normalized with total cellular proteins. For measuring heme levels in various organelles, the inventor used peroxidase-based reporters which express peroxidase activity along with a fluorescent marker like mCherry or eGFP in each organelle (24). Heme levels were measured exactly as described and normalized with the fluorescent signals to correct for variations, such as that in transfection efficiency. Only Calu-3 did not show sufficient fluorescent signals to allow proper measurements (24).

Measurement of Oxygen Consumption and ATP Levels. Oxygen consumption was measured, as described previously (16). Briefly, $10^6$ cells (in 350 μl) were introduced into the chamber of an Oxygraph system (Hansatech Instruments), with a Clark-type electrode placed at the bottom of the respiratory chamber. During measurements, the chamber was thermostated at 37° C. by a circulating water bath. An electromagnetic stir bar was used to mix the contents of the chamber.

Total ATP was measured with the ATP-determination kit (Molecular Probes) following the manufacturer's protocol. Briefly, cultured cells were collected and immediately placed in ice-cold lysis buffer (Cell Signaling) with protease and phosphatase inhibitors. Cell lysates were then centrifuged at 10,000 g for 10 min. 10 μl of lysates or 10 μl of ATP standard solution was added to 90 μl of reaction buffer in each well of a 96-well plate. Luminescence was measured using a Biotek Cytation 5 plate reader. All experiments were carried out in triplicate, and the background luminescence was subtracted from the measurement. ATP concentrations were calculated from the ATP standard curve and normalized with the numbers of cells used. To measure oxygen consumption rates and ATP levels from freshly isolated tumors, subcutaneous tumors were surgically resected from mice and cut into small pieces. Tumors were weighed and homogenized immediately using mechanical homogenizer to gain a homogenous cell suspension. Tissue debris was removed by gentle centrifugation. Cells were suspended in 400 ul of complete medium, and OCR was measured using a Clark-type electrode. ATP levels were measured with an ATP determination kit (Molecular probes). Both Oxygen consumption rates and ATP levels were normalized with protein amounts.

Preparation of protein extracts and Western blotting. Lung non-tumorigenic and tumorigenic cells were maintained (passage 3-5), collected, and lysed by using the RIPA buffer (Cell Signaling Technology) containing the protease inhibitor cocktail. Protein concentrations were determined by using the BCA assay kit (Thermo Scientific). 50 μg of proteins from each treatment condition were electrophoresed on 10% SDS-polyacrylamide gels, and then transferred onto the Immuno-Blot PVDF Membrane (Bio-Rad). The membranes were probed with antibodies, followed by detection with a chemiluminescence Western blotting kit (Roche Diagnostics). The signals were detected by using a Carestream image station 4000MM Pro, and quantitation was performed by using the Carestream molecular imaging software version 5.0.5.30 (Carestream Health, Inc.). Antibodies used include those to the following proteins: ALAS1 (1:1000, Novus Cat #NBP1-91656, RRID:AB_11048622), SLC46A1 (1:1000, Santa Cruz Biotechnology Cat #sc-134997, RRID:AB_11149379), SLC48A1 (1:1000, Santa Cruz Biotechnology Cat #sc-101957, RRID:AB_2191218), CYCS (1:1000, Santa Cruz Biotechnology Cat #sc-7159, RRID:AB_2090474), COX4 (1:1000, Santa Cruz Biotechnology Cat #sc-292052, RRID:AB_10843648), NRF1 (1:1000 Cell Signaling Technology Cat #46743, RRID: AB_2732888), TFAM (1:1000, Cell Signaling Technology Cat #8076S, RRID:AB_10949110), TFRC (1:1000, Novus Cat #NB100-92243, RRID; AB_1216384), SLC40A1 (1:1000, Novus Cat #NBP1-21502, RRID:AB_2302075), and β-actin (1:1000, Cell Signaling Technology Cat #4967, RRID:AB_330288).

Animals. NOD/SCID mice (IMSR Cat #CRL:394, RRID: IMSR_CRL:394) were purchased from Charles River Laboratories. Mice were bred and cared for in a University of Texas at Dallas specific pathogen-free animal facility in accordance with NIH guidelines. All animal procedures were conducted under protocols approved by Institutional Animal Care and Use Committee (IACUC) at the University of Texas at Dallas. Animals were regularly examined for any signs of stress and euthanized according to preset criteria.

Treatment of human xenograft lung tumors in NOD/SCID mice. To generate mice with NSCLC tumors in the lungs, $0.75 \times 10^6$ H1299-luc cells in serum-free medium were injected via tail vein in 6-8-week-old female NOD/SCID mice. Alternatively, $0.75 \times 10^6$ H1299-luc cells (passages 3-5) in serum-free medium containing 50% Matrigel were implanted directly on the lung. Mice were anesthetized with 2.5% isoflurane and oxygen mixture. H1299-luc cells were injected via tail vein or were injected about 1.5 cm above the lower left rib line through the intercostal region. Mice were then placed on a heating pad and observed until they revived from anesthesia. Mice were randomized into three groups (n=6 per group) that received vehicle (for control) or HSP2 (10 mg/kg, I.V., every 3 days) or HSP2 (25 mg/kg, I.V., every 3 days). Treatments started post cell implantation when lung tumors were detectable using bioluminescence imaging. Body weights were recorded once every week. Treatments were started only after BLI detected authentic signals ($>5 \times 10^6$ photons/second) to ensure the proper implantation of tumors. Treatments were stopped, and mice were sacrificed after the untreated mice with tumors appeared moribund. For detecting the toxicity of HSP2 treatment on blood and liver functions, blood was obtained from these mice via the sub-mandibular vein before sacrifice and was collected in blood collection tubes (BD microtainer tubes Cat #365963 and Cat #365974 from Fischer scientific) . Serum samples were prepared and then used for determining hemoglobin levels with a hemoglobin assay kit from Sigma-Aldrich (Cat #MAK115-1KT) and ALT levels (alanine transaminase levels) with an ALT activity assay kit from Sigma-Aldrich (MAK052-1KT), respectively. Whole blood samples were used for counting red blood cells (RBCs) using a hemocytometer. No morphological differences were observed in red cells from treated and untreated mice.

For subcutaneous tumor models, $2 \times 10^6$ H1299-luc cells or H1299 cells overexpressing eGFP (Control) or ALAS1 or SLC48A1 in serum-free medium containing 50% Matrigel were injected subcutaneously into the left flank region of 4-6 weeks old female NOD/SCID mice. Mice were randomized into treatment groups that received saline (for control) and HSP2 (I.V. 25 mg/kg every 3 days), respectively. Body masses were recorded once every week. Treatments were started only after BLI detected authentic tumor signals and tumors were visible to ensure the proper implantation of tumors. When the tumors in the control group reached 1 cm³, mice were euthanized by cervical dislocation. Tumors were resected and weighed.

In vivo bioluminescence imaging (BLI). Mice bearing lung tumor xenografts were imaged with an IVIS Lumina III In Vivo Imaging system (Perkin Elmer). Briefly, mice were anesthetized in the isoflurane chamber (2% isoflurane and oxygen), and luciferin (potassium salt; Perkin Elmer; 80 µl of 40 mg/ml) was administered subcutaneously between the scapulae. A BLI time course was acquired over 30 mins (Exposure time: auto, F Stop: 1.2, Binning: medium). The images were quantified using Living Image software version 4.5.2 (Perkin Elmer). Regions of interest (ROIs) were selected, and bioluminescence signals between 600 to 60000 counts were accepted as authentic signals. The total bioluminescent signals (photon/sec) from ROIs of mice were calculated as specified by the manufacturer's instructions.

Hematoxylin and Eosin (H&E) staining. Following the final imaging, mice were sacrificed. Lung tumors were excised and tumor tissues were prepared for histology. Paraffin embedding was performed at Histology core at University of Texas Southwestern Medical Center. The paraffin blocks were sectioned to obtain 5 µm sections which were utilized for Hematoxylin and Eosin staining. For H&E staining, tumor tissues were fixed in 4% formalin, embedded in paraffin and sectioned (5 µm). Then, sections were stained with H&E. Slides were scanned at a 40× resolution with an Olympus VS120 slide scanner and quantified using Cell Sens software from Olympus.

Immunohistochemistry (IHC). IHC was carried out exactly as described (32). Paraffin-embedded tumor tissues from mice described above were used. Six independent sets of human NSCLC grade 2 & 3 tissues and six independent sets of normal human lung tissues in paraffin slides were purchased from US Biomax, Inc. (Rockville, MD). Slides were deparaffinized, hydrated, and washed. After antigen retrieval, slides were blocked with 1×TBS/10% goat serum (16210-072, Gibco). Primary antibodies were diluted in 1×TBS/1% BSA/10% goat serum. The dilutions were 1:200 for ALAS1 (Santa Cruz Biotechnology Cat #sc-50531, RRID:AB_2225629), 1:200 for SLC48A1 (Santa Cruz Biotechnology Cat #sc-101957, RRID:AB_2191218); 1:200 for CYCS (Santa Cruz Biotechnology Cat #sc-7159, RRID: AB_2090474), 1:200 for PTGS2 (Santa Cruz Biotechnology Cat #sc-7951, RRID:AB_2084972); 1:200 for TFAM (Cell Signaling Technology Cat #8076S, RRID:AB_10949110); COX4I1 1:200, (Santa Cruz Biotechnology Cat #sc-292052, RRID:AB_10843648), NRF1 (1:1000 Cell Signaling Technology Cat #46743, RRID: AB_2732888); UQCRC2 1:100 (Santa Cruz Biotechnology Cat #sc-390378 RRID: AB_2754980) and COX5A 1:100 (Abcam Cat #ab110262 RRID:AB_10861723). Sections were incubated with primary antibodies overnight at 4° C. and then incubated with horseradish peroxidase (HRP)-conjugated goat anti-rabbit IgG (Thermo Fisher Scientific Cat #31460, RRID: AB_228341) at a dilution of 1:200 in 1× TBS/1% BSA for 45 mins at room temperature (RT). Slides were stained with tyramide signal amplification (TSA)-conjugated fluorophores, which were diluted 1:100 in 1× Plus Amplification Diluent (NEL810001KT, PerkinElmer). TSA-conjugated fluorophores were aspirated and slides were then washed. DAPI, diluted in TBST, was added to slides and incubated for 5 min at RT. Coverslips were mounted over the slides using VECTASHIELD mounting medium (Vector Laboratories), sealed, and stored in darkness at −20° C.

Slides were scanned at a 40× resolution with an Olympus VS120 slide scanner and quantified using cellSens software from Olympus. DAPI was used to visualize nuclei. Multiple regions of interest (ROIs) of equal area were drawn over tumor regions. ROIs were selected, so that equal numbers of cells (identified via nuclei) were included in each ROI. The ROIs were positioned evenly throughout tumor regions. ROIs were retested under three different filters—FITC, Cy3, and Cy5—to ensure that no artifacts were present. ROIs were re-positioned if artifacts were present under one or more filters. Minimum and maximum thresholds were set to avoid any background signal. Mean signal intensity from all ROIs were averaged, and the corresponding negative control average was subtracted to yield the signal intensity for each antigen.

Statistical analyses of data. Data from different treatment groups of cells, mice, and tissues were compared, and statistical analysis was performed with a Welch 2-sample t-test. For calculating correlation coefficients, the inventor used the Pearson formula for calculating correlation coefficient r and p-value.

$$r(X, Y) = \frac{\sum (x - \bar{x})(y - \bar{y})}{\sqrt{\sum (x - \bar{x})^2 \sum (y - \bar{y})^2}}$$

$$p = \frac{r\sqrt{n-2}}{1 - r^2}$$

Results

Heme synthesis and uptake are elevated to heterogeneous degrees in several types of NSCLC cell lines, leading to elevated mitochondrial heme levels. To gain insights into the degree of elevation and heterogeneity of heme metabolism and flux in lung tumors, the inventor measured heme biosynthesis, uptake, and degradation in several representative types of NSCLC cell lines. These include H1299 (with Nras Q61K p53 null), A549 (with Kras G12S, LKB1 Q37*), H460 (with Kras K61H LKB1 Q37*), Calu-3 (with Kras G13D p53 M237I mutations), and H1395 (with LKB1 deletion). She also used two pairs of cell lines representing normal lung epithelial cells (HBEC30KT and NL20 in FIGS. 1A-F, 2A-D, S1A-C & S2A-H) and tumorigenic cell lines (NSCLC line HCC4017 and NL20-TA in FIGS. 1A-F, 2A-D, 15A-C & 16A-H) (25). Clearly, heme biosynthesis (FIG. 1A) and uptake (FIG. 1B) were both increased in NSCLC cell lines and NL20-TA, although the increases varied considerably among different cell lines. When the folds of increase in heme biosynthesis and uptake were added for every cell line (FIG. 1C), they varied from 2- to 8-fold among different lung tumor cell lines. Increases in heme biosynthesis and uptake correlated with increases in the rate-limiting heme biosynthesis enzyme ALAS1 (FIG. 15A; r=0.90, p-value=0.0003) and the cell membrane heme uptake protein SLC46A1 (SLC46A1) (FIG. 15B; r=0.70, p-value=0.02), respectively.

Heme degradation was also elevated in NSCLC cell lines relative to non-tumorigenic cell lines, albeit to a varying degree (FIG. 1D). This increase correlated with the increase in HMOX1 enzyme (FIG. 15C; r=0.70; p-value=0.02). Iron is an essential nutrient and is closely linked to heme (33). Heme synthesis in non-erythroid cells is generally not affected by iron (34). Nonetheless, the inventor detected the levels of transferrin receptor (TFRC), which is responsible for cellular iron uptake from the circulation (35). She found that TFRC levels were increased in some, while unaffected or decreased in other NSCLC cell lines (FIG. 1E). This is consistent with the idea that iron availability is not a limiting factor in NSCLC cells.

To determine how elevated heme metabolism in NSCLC cells affects subcellular heme levels, the inventor used a series of previously developed subcellular peroxidase reporters designed to detect subcellular heme levels in mitochondria, cytosol, nuclei, and other organelles (24). All lung cell lines were efficiently transfected with the reporter plasmids, except for Calu-3, which did not allow efficient transfection of reporter plasmids. Clearly, the mitochondrial heme levels in NSCLC cell lines and the tumorigenic NL20-TA cell line were elevated relative to non-tumorigenic cell lines (FIG. 1F). The increase in heme synthesis and uptake was correlated with the increase in intracellular mitochondrial heme levels: $r=0.68$, $p$-value=0.03. Heme levels in other organelles were also increased in some tumor cell lines, but increases were not uniform (FIGS. 16A-E). The increase in heme synthesis and uptake was not correlated significantly with heme levels in other organelles. Mitochondrial heme is crucial for OXPHOS formation and function. These data suggest that increased heme synthesis and uptake in NSCLC cells leads to elevated mitochondrial heme levels.

Elevated mitochondrial heme levels lead to intensified oxygen consumption and ATP generation in NSCLC cell lines. Next, the inventor measured a series of bioenergetic and tumorigenic parameters. The rates of oxygen consumption (FIG. 2A) and levels of intracellular ATP (FIG. 2B) were elevated in tumorigenic cell lines, except for Calu-3, relative to non-tumorigenic cell lines. Elevated oxygen consumption should be accompanied by increased levels of mitochondrial OXPHOS enzymes. Increased expression of mitochondrial proteins should be facilitated by regulators promoting mitochondrial biogenesis, such as NRF1 and TFAM (36). Indeed, the levels of cytochrome c (CYCS) and COX4I1 (subunits of OXPHOS complexes), as well as the hemoprotein PTGS2, were elevated in NSCLC cell lines relative to non-tumorigenic cell lines (FIGS. 16F-H). Notably, two important regulators promoting mitochondrial biogenesis, NRF1 and TFAM (FIGS. 2C & 2D), were also upregulated in tumorigenic cell lines relative to non-tumorigenic cells lines. Thus, these observations are consistent with increased oxygen consumption rates and ATP levels in tumorigenic cell lines.

Measurements of migration (FIG. 17A) and invasion (FIG. 17B) in NSCLC cell lines showed that they exhibit varying degrees of tumorigenicity. Interestingly, the inventor found that the invasive capabilities of NSCLC cell lines, oxygen consumption rates, and intracellular ATP levels were well correlated with mitochondrial heme levels. The correlation coefficients are as follows: mitochondrial heme and oxygen consumption rates: Pearson $r=0.72$, $p$-value=0.02; mitochondrial heme and ATP levels: $r=0.78$, $p$-value=0.01; and mitochondrial heme and invasion: $r=0.71$, $p$-value=0.05. Together, these results strongly suggest that elevated heme biosynthesis and uptake in NSCLC cell lines lead to elevated levels of mitochondrial heme and OXPHOS subunits, which cause intensified oxygen consumption, ATP generation, and tumorigenic capabilities in NSCLC cells.

Figure 2:
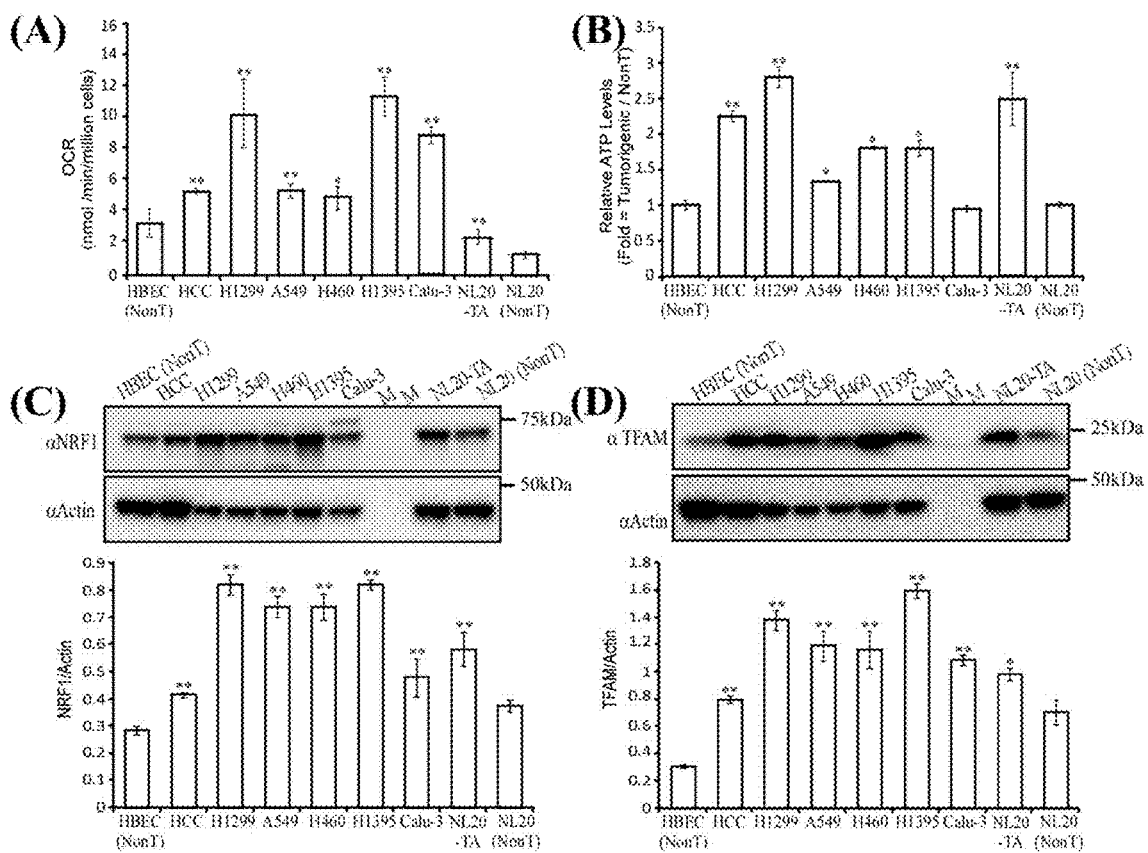
FIGS. 2A-D.

The inventor further confirmed the importance of enhanced levels of proteins/enzymes relating to heme function and mitochondrial respiration in lung cancer. FIGS. 18A-B show that the levels of the rate-limiting heme synthetic enzyme ALAS1 and the heme transporter SLC48A1 (SLC48A1) were both significantly enhanced in human NSCLC tissues relative to normal tissues. In the same vein, the heme-containing cytochrome c (FIG. 18C) and cyclooxygenase-2 (PTGS2) (FIG. 18D) were enhanced in human NSCLC tissues relative to normal tissues. Both cytochrome c (CYCS) and PTGS2 levels have previously been shown to be elevated in NSCLC cell lines and xenograft tumors (16). Notably, the levels of the mitochondrial biogenesis regulator TFAM were also enhanced in human NSCLC tissues (FIG. 18E), as is the case in NSCLC cell lines (FIG. 2D). Together, data from human NSCLC tissues, NSCLC cell lines, and xenograft tumors show that proteins/enzymes relating to heme function and mitochondrial respiration are upregulated in NSCLC cells and tumors.

Figure 3:
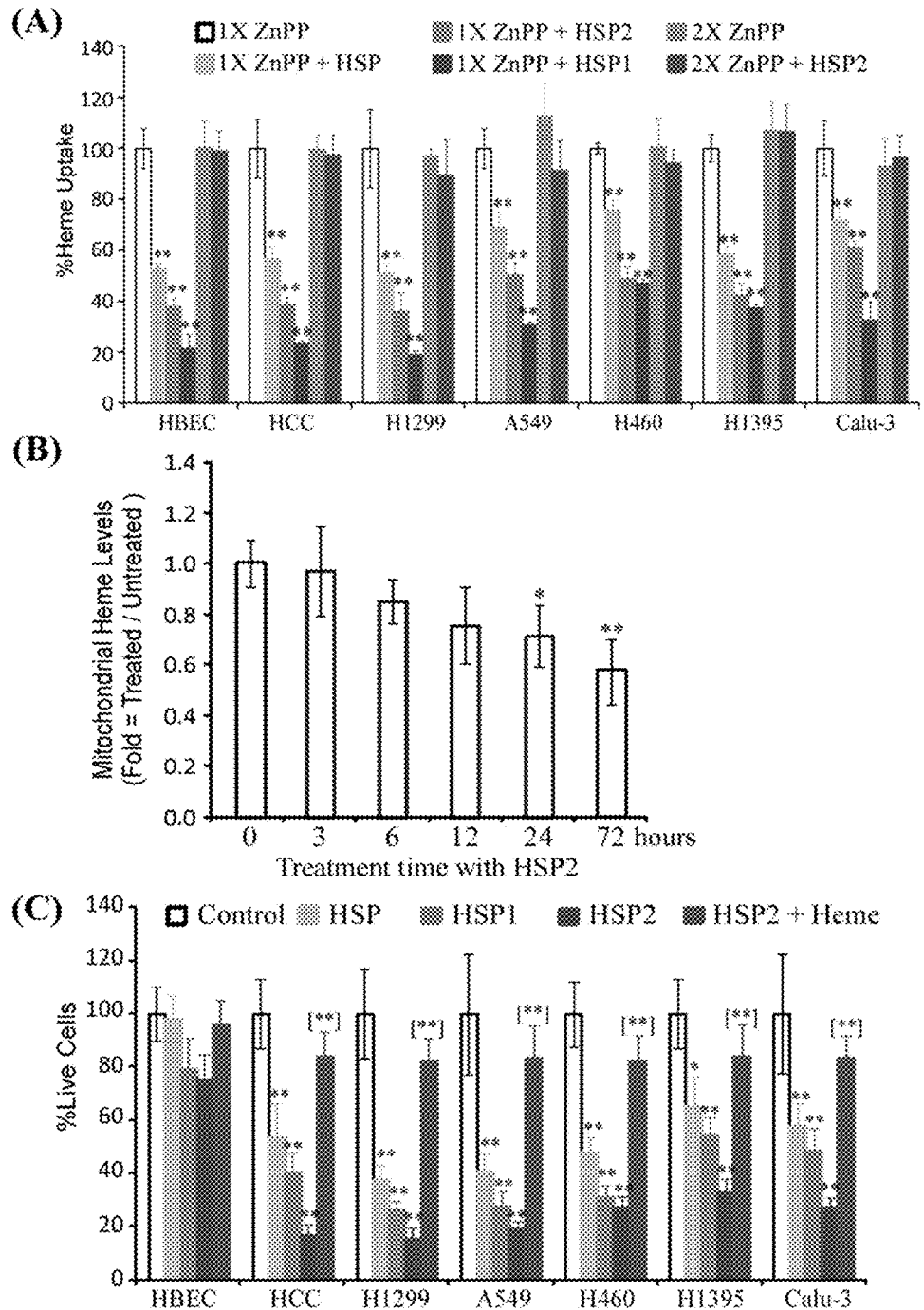
FIGS. 3A-C.
Figure 19A:
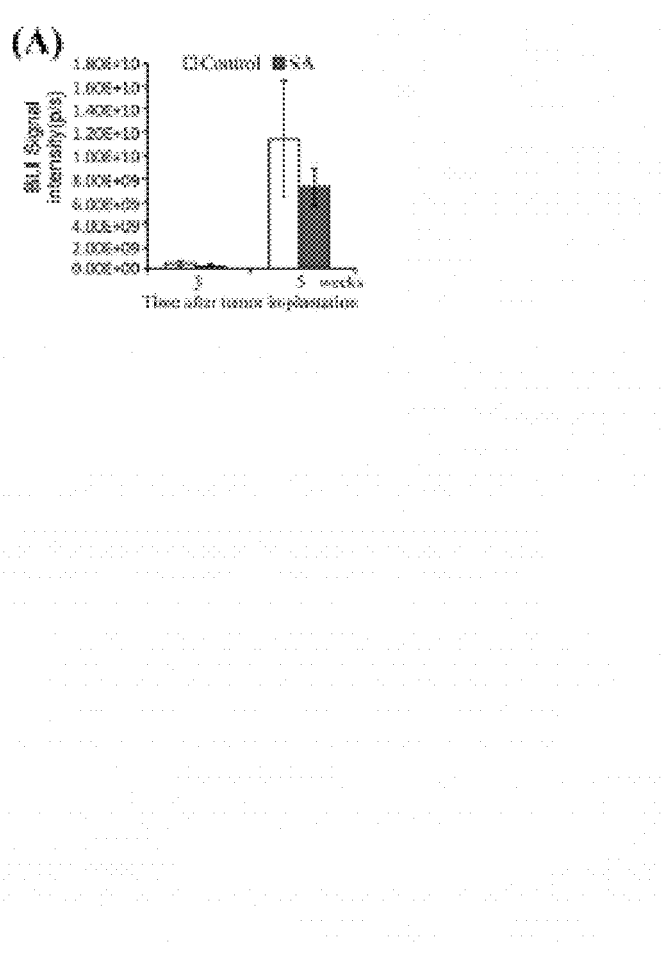
Figure 19B:
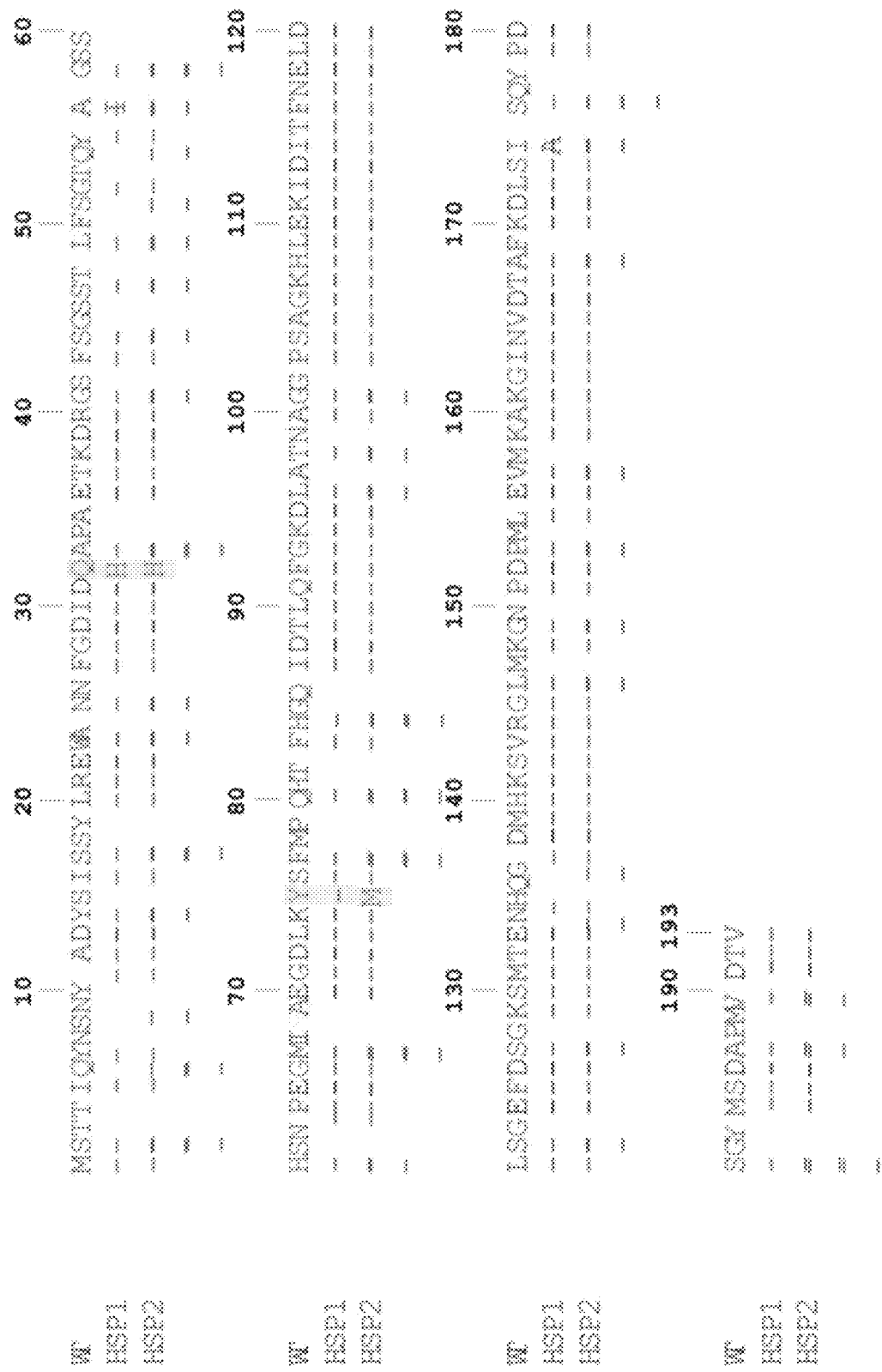

Engineered heme-sequestering peptides (HSPs) can inhibit heme uptake in NSCLC cell lines. If elevated heme metabolism is crucial for the tumorigenic functions of NSCLC cells, limiting heme availability may be effective for suppressing lung tumor growth and progression. Previous studies have identified succinyl acetone as an effective inhibitor of heme biosynthesis, as it inhibits the rate-limiting heme synthesis enzyme 5-aminolevulic synthase (ALAS1) in non-erythroid cells (37). However, succinyl acetone is not very effective in suppressing lung tumors in mice (FIG. 19A). Therefore, the inventor tried to lower heme availability by taking advantage of bacterial hemophores. The inventor took advantage of the well-characterized *Yersinia pestis* hemophore HasA (23). She used structural comparisons of known HasAs and a computational algorithm based on coevolution (38) to identify residues whose mutations may alter but not disrupt heme-binding properties. She designed several heme-sequestering peptides (HSPs), including HasA Q32H (HSP1) and HasA Q32H Y75M (HSP2) (FIG. 19B). These two peptides bind to heme strongly (FIG. 19C), like the wild-type HasA (23). The changed amino acids in HSP1 and HSP2 are known to coordinate heme well. Thus, the changes are not expected to reduce heme binding. Interestingly, HSP1 and HSP2 have enhanced capabilities to inhibit heme uptake in NSCLC cells (FIGS. 3A-C). HSP2 is the most potent in inhibiting heme uptake by NSCLC cell lines, reducing heme uptake by 5-fold in some cell lines (FIG. 3A). Furthermore, the effect of HSPs on heme uptake was reversed if more ZnPP (a heme analogue used for measuring heme uptake) was included (compare 1×ZnPP, 2×ZnPP, and 2×ZnPP+HSP2 in FIG. 3A), indicating that HSP2 does not reduce heme uptake by causing other toxicities. Note that 1×ZnPP likely saturated the capabilities of cells to uptake heme/ZnPP so that 2×ZnPP did not cause more uptake.

As a bacterial hemophore, HasA is not internalized by human host cells. Thus, HSPs are not expected to be internalized by NSCLC cells. Indeed, HSP2 remained in the medium even after prolonged incubation with NSCLC cells (FIGS. 19D-E). Fluorescent images of NSCLC cells also showed that ZnPP-HSP2 did not enter cells (FIG. 19F), while ZnPP in the medium without HSP2 entered cells and co-localized with mitotracker (FIG. 19G). Furthermore, the inventor detected the effect of HSP2 treatment on mitochondrial heme levels in NSCLC cells, because mitochondrial heme levels are correlated with heme synthesis and uptake, as well as invasion (see above results). FIG. 3B shows that mitochondrial heme levels gradually decreased as the treatment time with HSP2 increased. Together, these results strongly suggest that HSP2 acts on NSCLC cells by lowering heme uptake and mitochondrial heme levels.

HSPs effectively suppress NSCLC cell proliferation and tumorigenic functions. As expected, both HSP1 and HSP2 inhibited NSCLC cell proliferation in various NSCLC cell lines (FIG. 3C) and in a dose-dependent manner (FIGS. 20A-D). The effects of HSPs on the proliferation of the HBEC30KT cell line representing normal lung epithelial cells were much less severe relative to NSCLC cell lines (FIG. 3C and FIG. 20A). This is consistent with the idea that normal cells do not need as much heme as NSCLC cells need. The inventor also tested and compared the efficacies of HSP1, HSP2, and succinyl acetone at inhibition of tumorigenic functions in NSCLC cells. Evidently, HSP2 was more effective than succinyl acetone and HSP1 at inhibiting migration of H1299 (FIG. 4A) and A549 cells (FIG. 21A). Likewise, HSP2 was more effective than succinyl acetone and HSP1 at inhibiting invasion by H1299 (FIG. 4B) and A549 cells (FIG. 21B). Notably, addition of heme largely reversed the effects of HSP1 and HSP2, like succinyl acetone (SA), on reducing proliferation, migration and invasion of NSCLC cells (FIG. 3C, FIGS. 4A-B, FIGS. 21A-B). The reversal of HSP1 and HSP2 effects by heme addition supports the idea that the effects of HSP1 and HSP2, like SA, on migration and invasion are attributable to their effect on heme uptake. The inventor also found that SA, HSP1, and HSP2 strongly suppressed colony formation in H1299 (see FIGS. 4C-E) and A549 (FIGS. 21C-E) cells. Inhibition of heme degradation by SnPP appeared to reduce colony formation in NSCLC H1299 (FIG. 4F) and A549 (FIG. 21F) cells.

Figure 4:
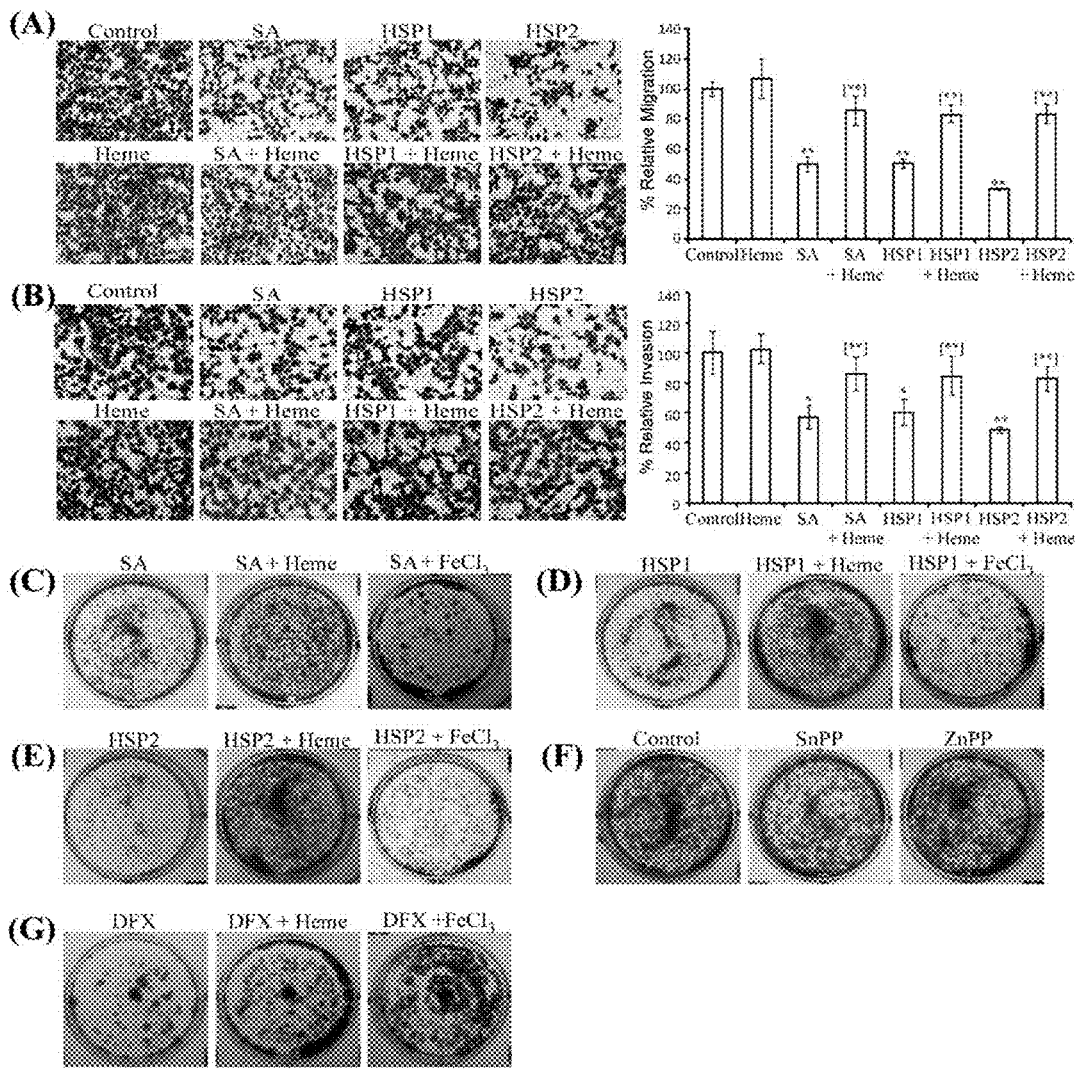
FIGS. 4A-G. HSPs inhibit migration capabilities (FIG. 4A) and invasion capabilities (FIG. 4B) in H1299 NSCLC cells. Succinyl acetone (SA) is shown for comparison. Addition of 10 mM heme largely reversed the effects of SA and HSPs. The images shown are cells that had migrated across Transwell inserts (in FIG. 4A) or had crossed invasion chambers coated with Corning Matrigel matrix and also passed Transwell inserts (in FIG. 4B). Data are plotted as mean ± SD. For statistical analysis, the levels in treated cells were compared to the levels in untreated cells with a Welch 2-sample t-test. *, p-value, 0.05, , p-value <0.005. For heme add-back experiments, the levels in cells treated with heme and HSP2 were compared to the levels in cells treated with only HSP2. [], p-value <0.005.

Addition of heme to cells treated with SA, HSP1, or HSP2 largely reversed the effects of these agents on colony formation (FIGS. 4C-E & FIGS. 21C-E), indicating that their effects are attributable to lack of heme. As expected, iron chelator deferoxamine (DFX) also reduced colony formation in NSCLC cells, and addition of iron largely reversed the effect of DFX (FIG. 4G & FIG. 21G). Addition of heme to DFX-treated cells partially reversed the effect on colony formation (FIG. 4G & FIG. 21G), but addition of iron to SA-, HSP1-, or HSP2-treated cells did not reverse the effects on colony formation (FIGS. 4C-E & FIGS. 21C-E). This is consistent with the fact that iron can be obtained via heme. However, extra iron cannot overcome the effect on heme synthesis or uptake, likely because iron is not a limiting factor in NSCLC cells, as in most non-erythroid cells (34). Consistent with this observation of differential effects of iron and heme on colony formation, data in FIGS. 21H-I show that HSP2, unlike DFX, had no significant effects on the levels of transferrin receptor TFRC and ferroportin SLC40A1.

Figure 5:
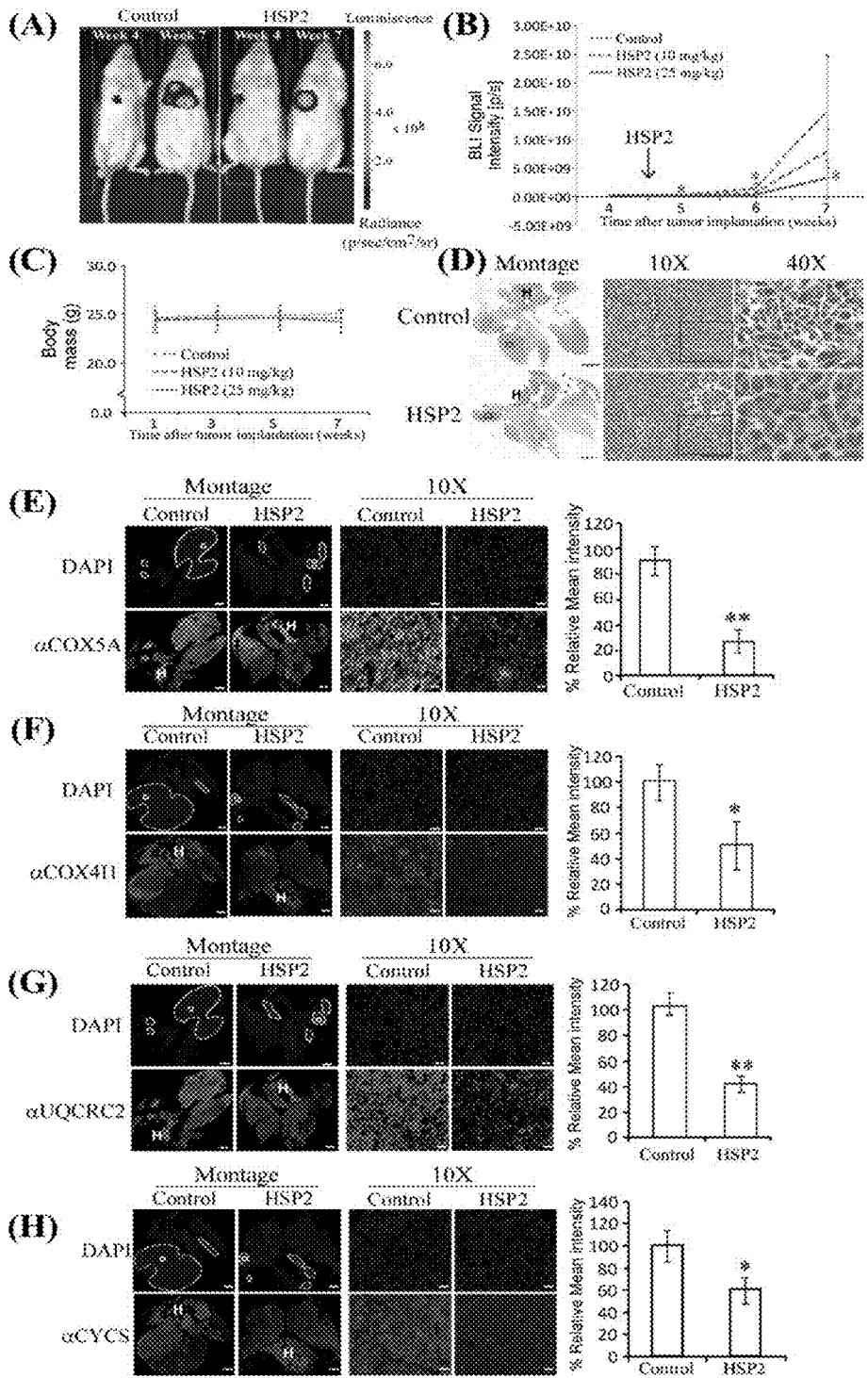
FIGS. 5A-H. The effect of HSP2 on the growth and progression of H1299 NSCLC lung tumor xenografts and on the levels of OXPHOS subunits in tumors.

HSP2 effectively suppresses the growth of human tumor xenografts in mice. To further assess the anti-tumor activity of HSP2 in vivo, the inventor examined the effects of administering HSP2 on the growth of human xenograft tumors in the lungs of NOD/SCID mice (FIGS. 5A-H). Detection of tumor growth and progression with BLI showed that HSP2 significantly suppressed lung tumor growth and progression (FIGS. 5A & 5B). HSP2 did not significantly change the body masses (FIG. 5C). Histological analysis with H&E staining confirmed that 25 mg/kg of HSP2 nearly eradicated the lung tumors (FIG. 5D). The inventor found that HSP2 was effective at suppressing tumor growth when it was administered to NOD/SCID mice with larger tumor xenografts in the lung (FIG. 22 showed 10× higher BLI signals than those in FIGS. 5A-H). HSP2 did not significantly affect red cell counts (FIG. 22C) and hemoglobin levels (FIG. 22D) in the blood, as well as liver function shown by Alanine transaminase (ALT) activity (FIG. 22E). These results show that inhibition of heme uptake by HSP2 can effectively suppress lung tumor growth and progression.

Figure 6:
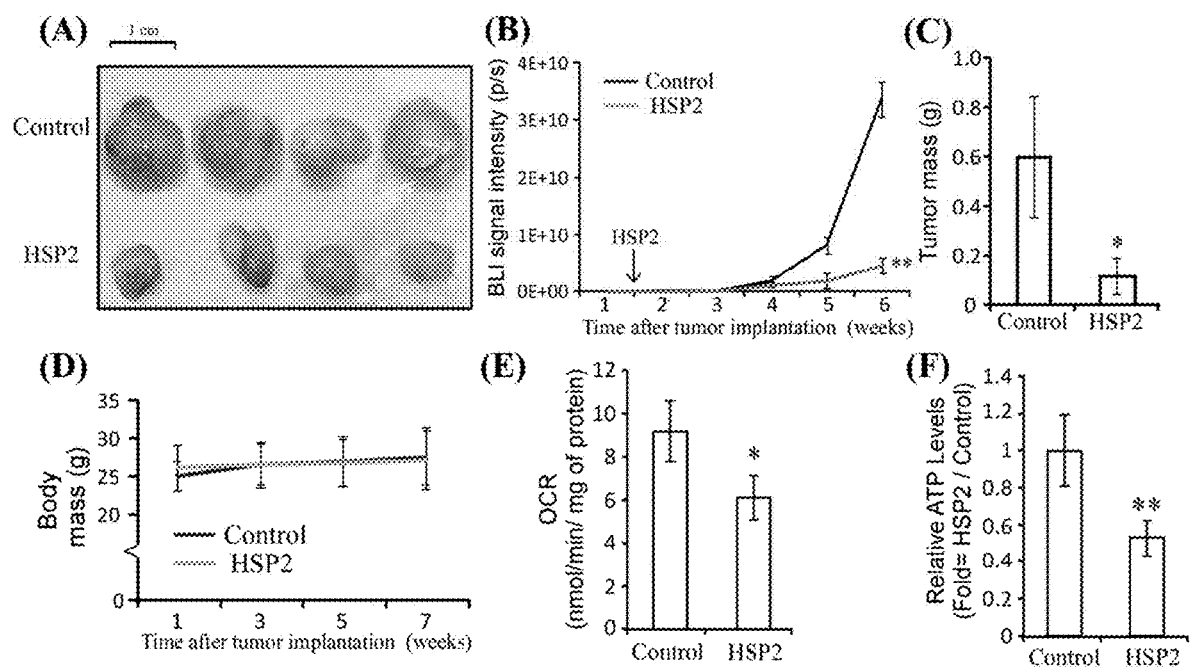
FIGS. 6A-F. HSP2 effectively suppresses the growth, oxygen consumption rates, and ATP generation in subcutaneous NSCLC tumor xenografts.

The inventor found that the levels of subunits of OXPHOS complexes, including COX5A (FIG. 5E), COX4I1 (FIG. 5F), UQCRC2 (FIG. 5G), and CYCS (FIG. 5H), were significantly reduced in HSP2-treated tumors, indicating reduced oxygen consumption. To further ascertain the effect of HSP2 on oxygen consumption, the inventor decided to directly detect oxygen consumption and ATP generation in lung tumors in mice. However, she found that it is difficult to isolate sufficient populations of tumor cells from orthotopic lung tumors or do measurements quick enough to collect valid data. To overcome these difficulties, she used subcutaneously implanted NSCLC tumors. HSP2 was very effective in suppressing subcutaneously implanted NSCLC tumors (FIGS. 6A-C). Notably, the oxygen consumption rates and ATP levels in HSP2-treated tumors were both significantly reduced relative to untreated tumors (populations of cells isolated quickly from tumors) (FIGS. 6E-F).

Figure 7:
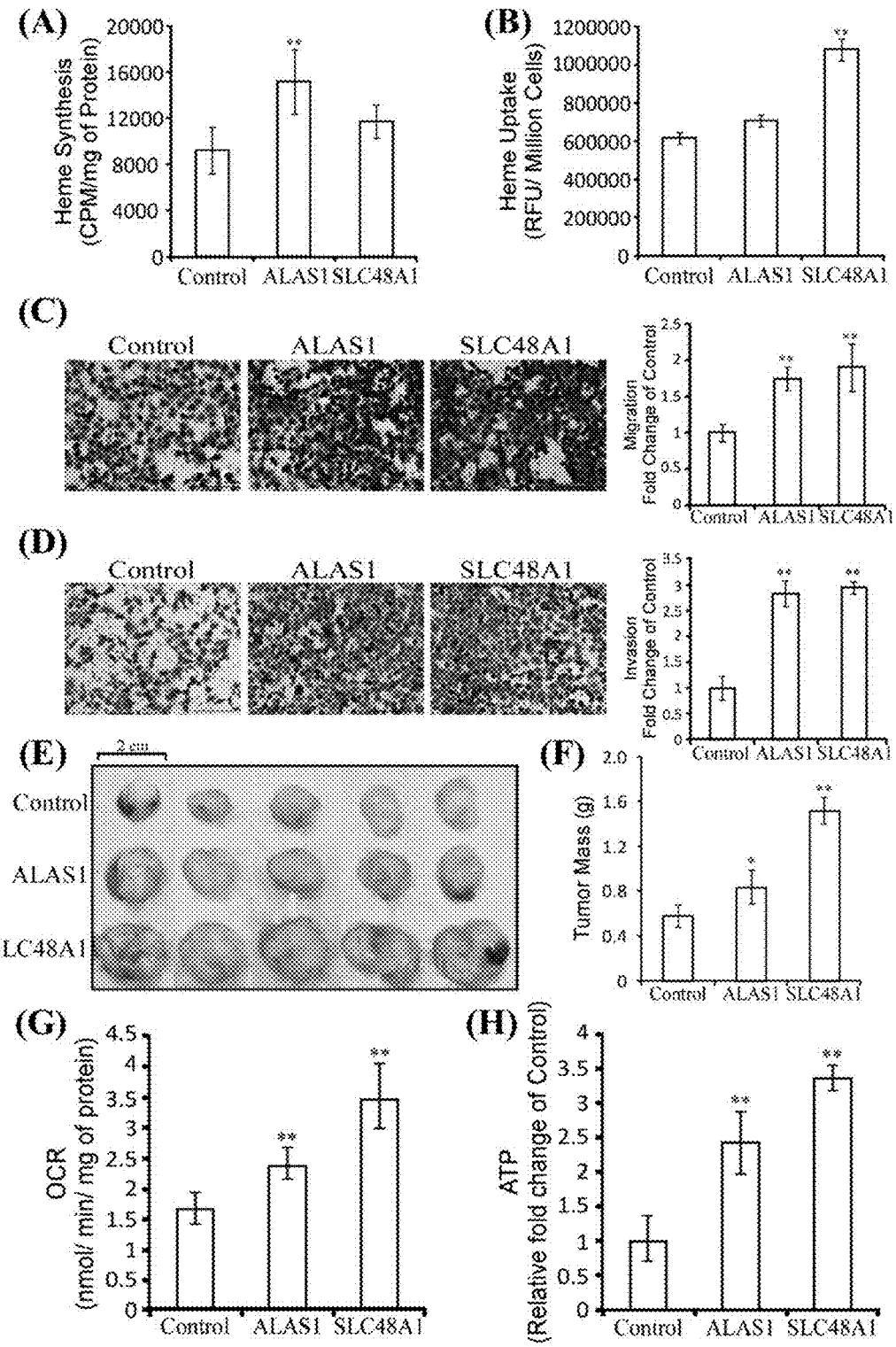
FIGS. 7A-H. The effects of overexpressing ALAS1 or SLC48A1 on heme synthesis, uptake, migration, invasion, and tumor growth of NSCLC cells.

Overexpression of ALAS1 or SLC48A1 promotes oxygen consumption, ATP generation, tumorigenic functions of NSCLC cells and tumor growth. To further ascertain the importance of heme in promoting NSCLC tumors, the inventor generated NSCLC cell lines that overexpress the rate-limiting heme synthesis enzyme ALAS1 or the heme uptake protein/transporter SLC48A1 (FIGS. 7A-H). She confirmed that relative to control cells, cells overexpressing ALAS1 exhibited elevated heme synthesis (FIG. 7A & FIG. 22F) while cells overexpressing SLC48A1 exhibited elevated heme uptake (FIG. 7B & FIG. 22G). These cells also showed elevated oxygen consumption (FIG. 22H). Importantly, these cells overexpressing ALAS1 or SLC48A1 exhibited enhanced migration (FIG. 7C), invasion (FIG. 7D), and colony formation (FIG. 22I). When these cells were implanted subcutaneously in NOD/SCID mice, they form bigger tumors than control cells (FIGS. 7E-F). Furthermore, tumors overexpressing ALAS1 or SLC48A1 exhibited elevated levels of oxygen consumption (FIG. 7G) and ATP generation (FIG. 7H). Taken together, these results strongly support the idea that increased heme availability resulting from elevated heme synthesis or uptake leads to higher oxygen consumption and ATP generation, which in turn fuels NSCLC cell tumorigenic functions and tumor growth.

Discussion

In the 1920s, Otto Warburg demonstrated that tumor cells metabolize glucose and generate lactate at higher levels than normal cells despite the presence of ample oxygen, a phenomenon called the Warburg effect (39). However, elevated glucose consumption and glycolysis in tumor cells do not necessarily lead to diminished oxidative metabolism and OXPHOS (8, 9). Numerous previous studies have shown that high glycolytic rates occur concomitantly with oxidative phosphorylation (OXPHOS) in cells of most tumors, and that function of mitochondrial OXPHOS is intact in most tumors (for a review, see (40)). More recent studies have demonstrated the importance of mitochondrial OXPHOS in the growth and progression of several types of tumors (41-43). Further, several studies demonstrated that oxidative metabolism and OXPHOS are crucial for conferring drug resistance of cancer cells and cancer stem cells. Farge et al. showed that OXPHOS contributes to acute myeloid leukemia resistance to cytarabine (13). Kuntz et al. showed that targeting mitochondrial OXPHOS eradicates drug-resistant CML stem cells (14). Lee et al. showed that MYC and MCL1 confer chemotherapy resistance by increasing mitochondrial OXPHOS in cancer stem cells in triple negative breast cancer (15).

Heme is a central molecule in mitochondrial OXPHOS and in virtually all processes relating to oxygen transport, storage, detoxification, and utilization (17, 18). Heme serves as an essential prosthetic group or cofactor for many proteins and enzymes that bind and use oxygen, such as cytochrome P450 and nitric oxide synthases (NOSs), and that detoxify ROSs, such as catalase and peroxidases. Three OXPHOS complexes, II, III, and IV, require heme for proper functioning. Multiple subunits in complexes III and IV require heme as a prosthetic group, and different forms of heme are present (40). Furthermore, heme serves as a signaling molecule that directly regulates diverse processes, including the expression and assembly of OXPHOS complexes (18, 19). Conversely, heme synthesis occurs in mitochondria and requires oxygen (34). Thus, heme and mitochondrial biogenesis are linked and are inter-dependent. Previously, the inventor showed that the levels of the rate-limiting heme biosynthetic enzyme ALAS1, heme uptake and transport proteins SLC48A1 and SLC46A1, and oxygen-utilizing hemoproteins, including CYP1B1 and PTGS2, are highly elevated in NSCLC tumors (16, 44). Other studies also showed that the expression of proteins involved in mitochondrial respiration and heme function are elevated in the tumor tissues of NSCLC patients (45, 46). Additionally, epidemiological studies indicated a positive association between intake of heme from meat and lung cancer (47).

Here, the inventor showed that the levels of heme biosynthesis and uptake, along with the levels of rate-limiting heme biosynthetic enzymes and heme transporters, are upregulated in NSCLC cells relative to non-tumorigenic lung cells (FIGS. 15A-B). This elevation causes the elevation of heme biosynthesis and uptake in NSCLC cells (FIGS. 1A-C). Increased heme biosynthesis and uptake in turn lead to elevated mitochondrial heme levels (FIG. 1F). Based on the levels of heme synthesis in normal medium and medium with heme depleted, the inventor estimates that NSCLC cells obtain about $2/3$ of heme via de novo synthesis and about $1/3$ via uptake from the medium (FIG. 22J). NSCLC cells are known to require serum for growth in culture while normal lung epithelial cells grow better in the absence of serum (25, 48). Fetal bovine serum used to culture NSCLC cells, like human blood, contains approximately 20 µM cell—free heme (49, 50). Thus, both in vitro in culture and in vivo in mice and humans, tumor cells have ample supply of heme from the medium or circulation. Heme degradation is also elevated in some NSCLC cells (FIG. 1D), and the inhibition of heme degradation by SnPP reduced colony formation in NSCLC cells (see FIG. 4F & FIG. 21F). SnPP has been shown to be a strong inhibitor for the activities of heme oxygenases (51). This result is consistent with other studies indicating a role of heme degradation in promoting tumorigenesis (52, 53). For example, a previous study showed that inhibition of heme degradation is lethal to hereditary leiomyomatosis and renal-cell cancer cells when fumarate hydratase is deficient (52). Very likely, elevated heme degradation in cancer cells promotes tumorigenic functions by increasing the production of potent antioxidants bilirubin and beliverdin, as well as iron.

Elevated mitochondrial heme levels can potentially influence mitochondrial OXPHOS in two ways: (1) by increasing the pool of heme which is incorporated into OXPHOS complexes and other hemoproteins, and (2) by upregulating the translocation and assembly of OXPHOS complexes and other enzymes. Therefore, the rates of oxygen consumption and ATP levels are both elevated in NSCLC cells relative to non-tumorigenic cells (FIGS. 2A-B). Two proteins important for mitochondrial biogenesis, NRF2 and TFAM, are increased in NSCLC cells relative to non-tumorigenic cells (FIGS. 2C-D). This is consistent with a previous study showing that loss of TFAM reduces tumorigenesis in an oncogenic Kras-driven mouse model of lung cancer (54). Elevated heme biosynthesis and uptake ultimately lead to enhanced tumorigenic capabilities in NSCLC cells (FIGS. 4A-G & FIGS. 21A-I). Therefore, the data presented here and those from previous studies all support the idea that heme is a pro-tumorigenic metabolic and signaling molecule. Hemoproteins and enzymes that are required for OXPHOS are also pro-tumorigenic. Interestingly, a recent study from the authors' lab showed that viable NSCLC tumor cells resistant to the vascular disrupting agent combretastatin A-4 phosphate exhibit further elevated levels of hemoproteins and proteins and enzymes involved in heme metabolism (32).

Thus, the inventor expected that inhibitors of heme synthesis and uptake should suppress tumorigenesis and may overcome drug resistance. Indeed, the data presented here show that inhibition of heme synthesis by succinyl acetone (SA) or inhibition of heme uptake by HSPs reduces tumorigenic functions of NSCLC cells (FIGS. 3A-C, FIGS. 4A-G, FIGS. 20A-D & FIGS. 21A-I). HSP2, which inhibits heme uptake more strongly than HSP1, diminishes tumorigenic functions of NSCLC cells most strongly. This raises the possibility that HSP2 can be a more effective agent against NSCLC cells than succinyl acetone. Indeed, HSP2 strongly suppressed the growth of both orthotopically implanted NSCLC tumors and subcutaneously implanted tumors (FIGS. 5A-H, FIGS. 6A-F & FIGS. 22A-J). Notably, addition of heme largely reverses the effects of SA and HSPs on proliferation, migration, invasion, and colony formation (FIG. 3C, FIGS. 4A-G & FIGS. 21A-I). These results strongly support the idea that the effects of SA and HSPs on NSCLC cell tumorigenic functions are attributable to their effects on heme synthesis and uptake, respectively.

The link between heme availability and NSCLC tumorigenesis is strongly supported by data obtained from examining HSP2-treated tumors (FIGS. 5A-H, FIGS. 6A-F & FIGS. 22A-J) and tumors formed by NSCLC cells overexpressing the rate-limiting heme synthesis enzyme ALAS1 or the heme uptake protein/transporter SLC48A1 (FIGS. 7A-H). HSP2-treated tumors (FIGS. 5A-H, FIGS. 6A-F & FIGS. 22A-J) show lowered levels of OXPHOS complex subunits (FIGS. 5E-5H), oxygen consumption (FIG. 6E), and ATP generation (FIG. 6F), indicating the effect of inhibited heme uptake on OXPHOS and ATP generation. Likewise, these data show that increased levels of ALAS1 or SLC48A1 cause increased heme synthesis (FIG. 7A) or uptake (FIG. 7B), respectively. This increase causes elevated oxygen consumption (FIG. 7G) and ATP generation (FIG. 7H) in NSCLC tumors, which then promotes tumor growth, as shown by increased tumor sizes and masses (FIGS. 7E-F).

Succinyl acetone has low toxicity to animals (55, 56). Likewise, data from the inventor's mouse studies suggest that HSP2 is not highly toxic to mice (FIGS. 22C-22E). HSP2 did not affect red cell counts (FIG. 22C), hemoglobin levels (FIG. 22D), and ALT activity indicative of liver function (FIG. 22E). Moreover, HSP2 did not significantly affect the proliferation of HBEC30KT cell line representing normal lung epithelial cells in the concentration range that affected the proliferation of NSCLC cells (FIG. 3C & FIG.

20A). Bacterial hemophore is not internalized by host mammalian cells. Thus, it is expected that HSP2 does not get into NSCLC cells, as indicated in FIGS. 19D-F. Notably, the data clearly showed that HSP2 inhibits heme uptake and reduces mitochondrial heme levels in NSCLC cells (FIGS. 3A-C). The lack of strong blood toxicity of HSP2 is likely attributable to the lack of the need for heme uptake in normal cells. For example, normal lung cells do not proliferate in the presence of serum, which containing cell-free heme, whereas NSCLC cells need serum for proliferation and tumorigenicity (48). The data presented here show that the levels of heme synthesis, uptake, oxygen consumption, and ATP are significantly lower in non-tumorigenic lung cells relative to NSCLC cells (FIGS. 1A-F & FIGS. 2A-D). Notably, during erythropoiesis, heme synthesis is induced prior to and is essential for globin synthesis (34, 57). Erythroid heme synthesis is very high and excessive. Previous experimental data suggested that erythrocytes produce excess heme for export and transport to other organs (57, 58). Thus, heme uptake is not needed for erythropoiesis, and erythrocytes can provide heme for other cells and tissues, including tumors. Thus, it is not surprising that heme sequestration by HSP2 does not cause erythroid toxicity during the treatment periods in mice (FIGS. 5A-H, FIGS. 6A-F & FIGS. 22A-J). It is also worth noting that suppression of tumor growth should also lower the demand for iron for tumor growth, thereby alleviating potential blood toxicity posed by HSP2.

Heme represents 97% of the functional iron pool in the human body. Iron can contribute to both tumor initiation and progression (59). Indeed, the inventor's data show that iron chelator deferoxamine (DFX) inhibited colony formation in NSCLC cells (FIG. 4G & FIG. 21G). However, addition of iron does not reverse the effects of SA or HSPs on colony formation (FIGS. 4C-E & FIGS. 21C-E), because iron cannot reverse the effects of SA and HSPs on heme synthesis or uptake. Heme and iron are linked: heme synthesis requires iron, and heme degradation releases iron. However, likely due to their respective chemical properties, the main biological functions of heme iron and non-heme iron in living organisms may have become distinct. Due to its unique property for binding oxygen, the primary functions of heme iron are for oxygen utilization, metabolism, and detoxification, particularly in OXPHOS for ATP generation. Non-heme iron, however, often exists in proteins and enzymes as iron-sulfur cluster, and has essential functions in DNA replication, repair, and cell cycle (59, 60). Thus, both iron depletion and heme depletion can have anti-tumor effects, but the mechanisms largely differ. Iron deficiency causes anemia, because red cells account for 80% of functional iron needed in humans or mammals (34). In humans and mammals, the need of other cells for iron can presumably be met by taking a small amount of iron from red cells. Indeed, iron availability affects heme synthesis in erythroid cells, but not non-erythroid cells. Furthermore, heme synthesis in erythroid and non-erythroid cells involves different ALASs and regulatory modes (34, 57). Thus, lowering heme availability should have more selective effects on NSCLC cells. Thus, targeting heme uptake and/or heme synthesis may provide a new and effective strategy for the treatment of NSCLC and perhaps other cancers resistant to existing therapies.

REFERENCES FOR EXAMPLE 1

1. Siegel R L, Miller K D, Jemal A. Cancer statistics, 2015. CA Cancer J Clin 2015; 65:5-29.
2. de Bruin E C, McGranahan N, Mitter R, Salm M, Wedge D C, Yates L, Jamal-Hanjani M, Shafi S, Murugaesu N, Rowan A J, Gronroos E, Muhammad M A, Horswell S, Gerlinger M, Varela I, Jones D, Marshall J, Voet T, Van Loo P, Rassl D M, Rintoul R C, Janes S M, Lee S M, Forster M, Ahmad T, Lawrence D, Falzon M, Capitanio A, Harkins T T, Lee C C, Tom W, Teefe E, Chen S C, Begum S, Rabinowitz A, Phillimore B, Spencer-Dene B, Stamp G, Szallasi Z, Matthews N, Stewart A, Campbell P, Swanton C. Spatial and temporal diversity in genomic instability processes defines lung cancer evolution. Science 2014; 346:251-6.
3. Brahmer J, Reckamp K L, Baas P, Crino L, Eberhardt W E, Poddubskaya E, Antonia S, Pluzanski A, Vokes E E, Holgado E, Waterhouse D, Ready N, Gainor J, Aren Frontera O, Havel L, Steins M, Garassino M C, Aerts J G, Domine M, Paz-Ares L, Reck M, Baudelet C, Harbison C T, Lestini B, Spigel D R. Nivolumab versus Docetaxel in Advanced Squamous-Cell Non-Small-Cell Lung Cancer. N Engl J Med 2015; 373:123-35.
4. Rittmeyer A, Barlesi F, Waterkamp D, Park K, Ciardiello F, von Pawel J, Gadgeel S M, Hida T, Kowalski D M, Dols M C, Cortinovis D L, Leach J, Polikoff J, Barrios C, Kabbinavar F, Frontera O A, De Marinis F, Turna H, Lee J S, Ballinger M, Kowanetz M, He P, Chen D S, Sandler A, Gandara D R. Atezolizumab versus docetaxel in patients with previously treated non-small-cell lung cancer (OAK): a phase 3, open-label, multicentre randomised controlled trial. Lancet 2017; 389:255-65.
5. Garon E B, Rizvi N A, Hui R, Leighl N, Balmanoukian A S, Eder J P, Patnaik A, Aggarwal C, Gubens M, Horn L, Carcereny E, Ahn M J, Felip E, Lee J S, Hellmann M D, Hamid O, Goldman J W, Soria J C, Dolled-Filhart M, Rutledge R Z, Zhang J, Lunceford J K, Rangwala R, Lubiniecki GM, Roach C, Emancipator K, Gandhi L. Pembrolizumab for the treatment of non-small-cell lung cancer. N Engl J Med 2015; 372:2018-28.
6. Reck M, Rodriguez-Abreu D, Robinson A G, Hui R, Csoszi T, Fulop A, Gottfried M, Peled N, Tafreshi A, Cuffe S, O'Brien M, Rao S, Hotta K, Leiby M A, Lubiniecki G M, Shentu Y, Rangwala R, Brahmer J R. Pembrolizumab versus Chemotherapy for PD-L1-Positive Non-Small-Cell Lung Cancer. N Engl J Med 2016; 375:1823-33.
7. Fan T W, Lane A N, Higashi R M, Farag M A, Gao H, Bousamra M, Miller D M. Altered regulation of metabolic pathways in human lung cancer discerned by (13)C stable isotope-resolved metabolomics (SIRM). Mol Cancer 2009; 8:41.
8. Hensley C T, Faubert B, Yuan Q, Lev-Cohain N, Jin E, Kim J, Jiang L, Ko B, Skelton R, Loudat L, Wodzak M, Klimko C, McMillan E, Butt Y, Ni M, Oliver D, Torrealba J, Malloy C R, Kernstine K, Lenkinski R E, DeBerardinis R J. Metabolic Heterogeneity in Human Lung Tumors. Cell 2016; 164:681-94.
9. Faubert B, Li K Y, Cai L, Hensley C T, Kim J, Zacharias L G, Yang C, Do Q N, Doucette S, Burguete D, Li H, Huet G, Yuan Q, Wigal T, Butt Y, Ni M, Torrealba J, Oliver D, Lenkinski R E, Malloy C R, Wachsmann J W, Young J D, Kernstine K, DeBerardinis R J. Lactate Metabolism in Human Lung Tumors. Cell 2017; 171:358-71 e9.
10. Hui S, Ghergurovich J M, Morscher R J, Jang C, Teng X, Lu W, Esparza L A, Reya T, Le Z, Yanxiang Guo J, White E, Rabinowitz J D. Glucose feeds the TCA cycle via circulating lactate. Nature 2017; 551:115-8.
11. Sotgia F, Fiorillo M, Lisanti M P. Mitochondrial markers predict recurrence, metastasis and tamoxifen-resistance in breast cancer patients: Early detection of treatment failure with companion diagnostics. Oncotarget 2017; 8:68730-45.
12. Jeon J H, Kim D K, Shin Y, Kim H Y, Song B, Lee E Y, Kim J K, You H J, Cheong H, Shin D H, Kim S T, Cheong J H, Kim S Y, Jang H. Migration and invasion of drug-resistant lung adenocarcinoma cells are dependent on mitochondrial activity. Exp Mol Med 2016; 48:e277.
13. Farge T, Saland E, de Toni F, Aroua N, Hosseini M, Perry R, Bosc C, Sugita M, Stuani L, Fraisse M, Scotland S, Larrue C, Boutzen H, Feliu V, Nicolau-Travers M L, Cassant-Sourdy S, Broin N, David M, Serhan N, Sarry A, Tavitian S, Kaoma T, Vallar L, Iacovoni J, Linares L K, Montersino C, Castellano R, Griessinger E, Collette Y, Duchamp O, Barreira Y, Hirsch P, Palama T, Gales L, Delhommeau F, Garmy-Susini B H, Portais J C, Vergez F, Selak M, Danet-Desnoyers G, Carroll M, Recher C, Sarry J E. Chemotherapy-Resistant Human Acute Myeloid Leukemia Cells Are Not Enriched for Leukemic Stem Cells but Require Oxidative Metabolism. Cancer Discov 2017; 7:716-35.
14. Kuntz E M, Baquero P, Michie A M, Dunn K, Tardito S, Holyoake T L, Helgason G V, Gottlieb E. Targeting mitochondrial oxidative phosphorylation eradicates therapy-resistant chronic myeloid leukemia stem cells. Nat Med 2017; 23:1234-40.
15. Lee K M, Giltnane J M, Balko J M, Schwarz L J, Guerrero-Zotano A L, Hutchinson K E, Nixon M J, Estrada M V, Sanchez V, Sanders M E, Lee T, Gomez H, Lluch A, Perez-Fidalgo J A, Wolf M M, Andrejeva G, Rathmell J C, Fesik S W, Arteaga C L. MYC and MCL1 Cooperatively Promote Chemotherapy-Resistant Breast Cancer Stem Cells via Regulation of Mitochondrial Oxidative Phosphorylation. Cell Metab 2017; 26:633-47 e7.
16. Hooda J, Cadinu D, Alam M M, Shah A, Cao T M, Sullivan L A, Brekken R, Zhang L. Enhanced heme function and mitochondrial respiration promote the progression of lung cancer cells. PLoS One 2013; 8:e63402.
17. Ortiz de Montellano P R. Hemes in Biology. 2009. In Wiley Encyclopedia of Chemical Biology, pp. 240-9. West Sussex: John Wiley & Sons, Ltd
18. Padmanaban G, Venkateswar V, Rangarajan P N. Haem as a multifunctional regulator. Trends Biochem Sci 1989; 14:492-6.
19. Kim H J, Khalimonchuk O, Smith P M, Winge D R. Structure, function, and assembly of heme centers in mitochondrial respiratory complexes. Biochim Biophys Acta 2012; 1823:1604-16.
20. Yao X, Balamurugan P, Arvey A, Leslie C, Zhang L. Heme controls the regulation of protein tyrosine kinases Jak2 and Src. Biochem Biophys Res Commun 2010; 403:30-5.
21. Barr I, Smith A T, Chen Y, Senturia R, Burstyn J N, Guo F. Ferric, not ferrous, heme activates RNA-binding protein DGCR8 for primary microRNA processing. Proc Natl Acad Sci USA 2012; 109:1919-24.
22. Kuhl T, Imhof D. Regulatory Fe(II/III) heme: the reconstruction of a molecule's biography. Chembiochem 2014; 15:2024-35.
23. Kumar R, Lovell S, Matsumura H, Battaile K P, Moenne-Loccoz P, Rivera M. The hemophore HasA from *Yersinia pestis* (HasAyp) coordinates hemin with a single residue, Tyr75, and with minimal conformational change. Biochemistry 2013; 52:2705-7.
24. Yuan X, Rietzschel N, Kwon H, Walter Nuno A B, Hanna D A, Phillips J D, Raven E L, Reddi A R, Hamza I. Regulation of intracellular heme trafficking revealed by subcellular reporters. Proc Natl Acad Sci USA 2016; 113:E5144-52.
25. Whitehurst A W, Bodemann B O, Cardenas J, Ferguson D, Girard L, Peyton M, Minna J D, Michnoff C, Hao W, Roth M G, Xie X J, White M A. Synthetic lethal screen identification of chemosensitizer loci in cancer cells. Nature 2007; 446:815-9.
26. Ramirez R D, Sheridan S, Girard L, Sato M, Kim Y, Pollack J, Peyton M, Zou Y, Kurie J M, Dimaio J M, Milchgrub S, Smith A L, Souza R F, Gilbey L, Zhang X, Gandia K, Vaughan M B, Wright W E, Gazdar A F, Shay J W, Minna J D. Immortalization of human bronchial epithelial cells in the absence of viral oncoproteins. Cancer Res 2004; 64:9027-34.
27. Sinclair P R, Gorman N, Jacobs J M. Measurement of heme concentration. Curr Protoc Toxicol 1999; Chapter 8:Unit 8.3.4-8.3.7.
28. Zhu Y, Hon T, Ye W, Zhang L. Heme deficiency interferes with the Ras-mitogen-activated protein kinase signaling pathway and expression of a subset of neuronal genes. Cell Growth Differ 2002; 13:431-9.
29. Hooda J, Alam M, Zhang L. Measurement of Heme Synthesis Levels in Mammalian Cells. J Vis Exp 2015: e51579.
30. Bailao E F, Parente J A, Pigosso L L, de Castro K P, Fonseca F L, Silva-Bailao M G, Bao S N, Bailao A M, Rodrigues M L, Hernandez O, McEwen J G, Soares C M. Hemoglobin uptake by *Paracoccidioides* spp. is receptor-mediated. PLoS Negl Trop Dis 2014; 8:e2856.
31. Yuan X, Protchenko O, Philpott C C, Hamza I. Topologically conserved residues direct heme transport in HRG-1-related proteins. J Biol Chem 2012; 287:4914-24.
32. Dey S, Kumari S, Kalainayakan S P, Campbell J, 3rd, Ghosh P, Zhou H, FitzGerald K E, Li M, Mason R P, Zhang L, Liu L. The vascular disrupting agent combretastatin A-4 phosphate causes prolonged elevation of proteins involved in heme flux and function in resistant tumor cells. Oncotarget 2018; 9:4090-101.
33. Beutler E, Bothwell T H, Charlton R W, Motulsky A G. Hereditary Hemochromatosis. 2009. In The metabolic and molecular bases of inherited disease, ed. C R Scriver, A L Beaudt, W S Sly, D Valle, C Barton, K W Kinzler, B Vogelstein, pp. Chapter 127: 1-79. New York: The McGraw-Hill Companies, Inc.
34. Anderson K E, Sassa S, Bishop D F, Desnick R J. Disorders of heme biosynthesis: X-linked sideroblastic anemia and the porphyrias. 2009. In The metabolic and molecular bases of inherited disease, ed. CR Scriver, A L Beaudt, W S Sly, D Valle, C Barton, K W Kinzler, B Vogelstein, pp. Chapter 124: 1-53. New York: The McGraw-Hill Companies, Inc.
35. Kawabata H. Transferrin and transferrin receptors update. Free Radic Biol Med 2018;
36. Uittenbogaard M, Chiaramello A. Mitochondrial biogenesis: a therapeutic target for neurodevelopmental disorders and neurodegenerative diseases. Curr Pharm Des 2014; 20:5574-93.
37. De Matteis F, Marks G S. The effect of N-methylprotoporphyrin and succinyl-acetone on the regulation of heme biosynthesis in chicken hepatocytes in culture. FEBS Lett 1983; 159:127-31.
38. Morcos F, Pagnani A, Lunt B, Bertolino A, Marks D S, Sander C, Zecchina R, Onuchic J N, Hwa T, Weigt M. Direct-coupling analysis of residue coevolution captures native contacts across many protein families. Proc Natl Acad Sci USA 2011; 108:E1293-301.

39. Warburg O. The Metabolism of Tumours 1930. London: Constable & Co.
40. Alam M M, Lal S, FitzGerald K E, Zhang L. A holistic view of cancer bioenergetics: mitochondrial function and respiration play fundamental roles in the development and progression of diverse tumors. Clin Transl Med 2016; 5:3.
41. Viale A, Pettazzoni P, Lyssiotis C A, Ying H, Sanchez N, Marchesini M, Carugo A, Green T, Seth S, Giuliani V, Kost-Alimova M, Muller F, Colla S, Nezi L, Genovese G, Deem A K, Kapoor A, Yao W, Brunetto E, Kang Y, Yuan M, Asara J M, Wang Y A, Heffernan T P, Kimmelman A C, Wang H, Fleming J B, Cantley L C, DePinho R A, Draetta G F. Oncogene ablation-resistant pancreatic cancer cells depend on mitochondrial function. Nature 2014; 514:628-32.
42. LeBleu V S, O'Connell J T, Gonzalez Herrera K N, Wikman H, Pantel K, Haigis M C, de Carvalho F M, Damascena A, Domingos Chinen L T, Rocha R M, Asara J M, Kalluri R. PGC-1alpha mediates mitochondrial biogenesis and oxidative phosphorylation in cancer cells to promote metastasis. Nat Cell Biol 2014; 16:992-1003, 1-15.
43. Tan A S, Baty J W, Dong L F, Bezawork-Geleta A, Endaya B, Goodwin J, Bajzikova M, Kovarova J, Peterka M, Yan B, Pesdar E A, Sobol M, Filimonenko A, Stuart S, Vondrusova M, Kluckova K, Sachaphibulkij K, Rohlena J, Hozak P, Truksa J, Eccles D, Haupt L M, Griffiths L R, Neuzil J, Berridge M V. Mitochondrial genome acquisition restores respiratory function and tumorigenic potential of cancer cells without mitochondrial DNA. Cell Metab 2015; 21:81-94.
44. Hooda J, Shah A, Zhang L. Heme, an essential nutrient from dietary proteins, critically impacts diverse physiological and pathological processes. Nutrients 2014; 6:1080-102.
45. Sotgia F, Lisanti M P. Mitochondrial markers predict survival and progression in non-small cell lung cancer (NSCLC) patients: Use as companion diagnostics. Oncotarget 2017; 8:68095-107.
46. Lam T K, Rotunno M, Ryan B M, Pesatori A C, Bertazzi P A, Spitz M, Caporaso N E, Landi M T. Heme-related gene expression signatures of meat intakes in lung cancer tissues. Mol Carcinog 2014; 53:548-56.
47. Tasevska N, Sinha R, Kipnis V, Subar A F, Leitzmann M F, Hollenbeck A R, Caporaso N E, Schatzkin A, Cross A J. A prospective study of meat, cooking methods, meat mutagens, heme iron, and lung cancer risks. Am J Clin Nutr 2009; 89:1884-94.
48. Sato M, Larsen J E, Lee W, Sun H, Shames D S, Dalvi M P, Ramirez R D, Tang H, DiMaio J M, Gao B, Xie Y, Wistuba, II, Gazdar A F, Shay J W, Minna J D. Human lung epithelial cells progressed to malignancy through specific oncogenic manipulations. Mol Cancer Res 2013; 11:638-50.
49. Oh J Y, Hamm J, Xu X, Genschmer K, Zhong M, Lebensburger J, Marques M B, Kerby J D, Pittet J F, Gaggar A, Patel R P. Absorbance and redox based approaches for measuring free heme and free hemoglobin in biological matrices. Redox Biol 2016; 9:167-77.
50. Muller-Eberhard U, Javid J, Liem H H, Hanstein A, Hanna M. Plasma concentrations of hemopexin, haptoglobin and heme in patients with various hemolytic diseases. Blood 1968; 32:811-5.
51. Wong R J, Vreman H J, Schulz S, Kalish F S, Pierce N W, Stevenson D K. In vitro inhibition of heme oxygenase isoenzymes by metalloporphyrins. J Perinatol 2011; 31 Suppl 1:S35-41.
52. Frezza C, Zheng L, Folger O, Rajagopalan K N, MacKenzie E D, Jerby L, Micaroni M, Chaneton B, Adam J, Hedley A, Kalna G, Tomlinson I P, Pollard P J, Watson D G, Deberardinis R J, Shlomi T, Ruppin E, Gottlieb E. Haem oxygenase is synthetically lethal with the tumour suppressor fumarate hydratase. Nature 2011; 477:225-8.
53. Nowis D, Bugajski M, Winiarska M, Bil J, Szokalska A, Salwa P, Issat T, Was H, Jozkowicz A, Dulak J, Stoklosa T, Golab J. Zinc protoporphyrin IX, a heme oxygenase-1 inhibitor, demonstrates potent antitumor effects but is unable to potentiate antitumor effects of chemotherapeutics in mice. BMC Cancer 2008; 8:197.
54. Weinberg F, Hamanaka R, Wheaton W W, Weinberg S, Joseph J, Lopez M, Kalyanaraman B, Mutlu G M, Budinger G R, Chandel N S. Mitochondrial metabolism and ROS generation are essential for Kras-mediated tumorigenicity. Proc Natl Acad Sci USA 2010 107:8788-93.
55. Raff R F, Storb R, Graham T, Fidler J M, Sale G E, Johnston B, Deeg H J, Pepe M, Schuening F, Appelbaum F R, et al. Pharmacologic, toxicologic, and marrow transplantation studies in dogs given succinyl acetone. Transplantation 1992; 54:813-20.
56. Bourque S L, Benjamin C D, Adams M A, Nakatsu K. Lack of hemodynamic effects after extended heme synthesis inhibition by succinylacetone in rats. J Pharmacol Exp Ther 2010; 333:290-6.
57. Dailey H A, Meissner P N. Erythroid heme biosynthesis and its disorders. Cold Spring Harb Perspect Med 2013; 3:a011676.
58. Khan A A, Quigley J G. Control of intracellular heme levels: heme transporters and heme oxygenases. Biochim Biophys Acta 2011; 1813:668-82.
59. Torti S V, Manz D H, Paul B T, Blanchette-Farra N, Torti F M. Iron and Cancer. Annu Rev Nutr 2018; 38:97-125.
60. Zhang C. Essential functions of iron-requiring proteins in DNA replication, repair and cell cycle control. Protein Cell 2014; 5:750-60.

Example 2

Materials and Methods

Purification of HeSPs, protein binding to heme-agarose beads, spectroscopic analyses, size exclusion chromatography, protease sensitivity assay. HeSPs were purified with the pET11a expression system. The pET11a expression vector for *Y. pestis* HasA residues 1-193 (HasA$_{yp}$) was kindly provided by Dr. Mario Rivera (University of Kansas)[30]. HeSP2 contains Q32H Y75M double mutations, HeSP2H contains Q32H Y75H double mutations, and HeSP2C contains Q32H Y75C double mutations. The mutations were generated with the QuikChange II Site-Directed Mutagenesis Kit (Agilent Technologies). The double mutations were generated with the expression vector for HasA$_{yp}$. HeSP2del is HeSP2 with 125-133 aa (FDSGKSMTE (SEQ ID NO: 11)) residues delated; HeSP2ec contains 1-128 aa residues of HeSP2 fused with 133-196 aa residues of *Erwinia carotovora* HasA; HeSP2pc contains 1-136aa residues of HeSP2 fused with 139-196 aa residues of *Pectobacterium carotovorum* HasA; and HeSP2pf contains 1-101aa residues of HeSP2 fused with 104-194 aa residues of *Pectobacterium fluorenscens* HasA. DNA sequences encoding the deletion and hybrid proteins were synthesized (gBlocks, Integrated DNA Technologies Inc) and cloned in pET11a expression system. All DNA clones were confirmed by sequencing (Eurofins Genomics LLC). To purify HeSPs from *E. coli*, BL21(DE3) bearing the pET-11a expression plasmids were grown to $A_{0.8}$, and induced with 1 mM isopropyl β-D-1-thiogalactopyranoside (IPTG) for 5 hours at 30° C. Cells were collected and lysed with a French Press. HeSPs were purified with a Q-Sepharose Fast Flow column (GE Healthcare), followed by size exclusion chromatography, as described[30]. All purified proteins were analyzed on SDS-PAGE gels.

To detect protein binding to heme with heme agarose beads (Sigma), 500 pmol purified proteins were incubated with 20 μl beads in 60 μl heme binding buffer (20 mM Tris pH 8.0, 500 mM NaCl, and 1% TritonX-100) for 1 hour at 4° C. After incubation, the beads were pelleted by centrifugation, and the supernatant was collected. The beads were then washed twice with heme binding buffer. Subsequently, proteins bound to the beads and in the supernatant were electrophoresed on SDS polyacrylamide gels and visualized by Coomassie blue staining. Heme absorbance spectra were measured with a Varian Cary® 50 UV-Vis Spectrophotometer. Samples contained 10 μM protein and 5 μM Heme. Protein and heme were prepared in 20 mM Tris, pH 8.0 and 500 mM NaCl; the imidazole stock was adjusted to pH 8.0 with HCl. Each sample was incubated for 30 seconds after the addition of heme, prior to absorbance measurement. Size exclusion chromatography to separate heme and heme-protein complexes were carried out using 1 ml Sephadex-G50 (Sigma) columns, as described[31]. For chymotrypsin sensitivity assay, 20 μM purified proteins were pre-incubated with or without heme (35 μg/ml) for 10 min in 20 mM Tris, pH8.0, 500 mM NaCl. Then, chymotrypsin was added to the proteins for 10 min. The reactions were stopped by adding SDS loading buffer, and samples were analyzed by SDS-PAGE.

Detection of heme transfer from hemoglobin to HasA and HeSP2 using native polyacrylamide gene electrophoresis (PAGE). Apo-HeSPs were mixed with hemoglobin to allow heme transfer. HeSP+hemoglobin were mixed and incubated for 30 minutes or indicated times at 4° C. After incubation, buffer with 5% glycerol, 4 mM Tris (pH 8.0), 40 mM NaCl, 4 mM MgCl2 was added, and samples were separated by electrophoresis on native 5% polyacrylamide gels in ⅓× Tris-borate-ethylenediaminetetraacetic acid. Hemoglobin, apo-HeSP, and heme-bound HeSP were also analyzed in parallel for controls and comparison. Native PAGE gels were subjected to heme staining and Coomassie blue staining. Heme staining was performed using the BioFX TMB One Component HRP Microwell Substrate (Surmodics).

Cell culture and measurements of heme uptake, cell proliferation, and apoptosis. NSCLC cell line H1299 (ATCC Cat #CRL-5803, RRID:CVCL_0060) was purchased from ATCC, maintained in RPMI medium, and supplemented with 5% heat-inactivated, fetal bovine serum. H1299 expressing luciferase was generated by infection with lentiviral particles bearing the EF1a-Luciferase (firefly) gene (AMSBIO)[11]. Cell lines were authenticated by Genetica and were found to be 96% identical to the standard (authentication requires >80%). Cell lines were tested for *mycoplasma* using a MycoFluor™ *Mycoplasma* Detection Kit (Molecular Probes), and the results were negative.

Cell proliferation was measured by counting live cells, as described[11]. For measuring heme uptake, a fluorescent analog of heme, zinc protoporphyrin IX (ZnPP, Frontier Scientific Inc.), was used, as described[11]. Briefly, 10,000 NSCLC cells were seeded in 96-well plates. Cells were incubated for 3 hours with 60 μmol/L ZnPP in the presence or the absence of 40 μmol/L HeSPs. Fluorescence intensity was measured with a Biotek Cytation 5 plate reader. Experiments were conducted in triplicates, and ZnPP uptake was normalized with total cellular proteins. Apoptosis was detected by using the ApoAlert™ Annexin V-FITC Apoptosis Kit (Clontech). Cells were seeded in a 96-well black wall clear bottom plate at the density of 5,000 cells per well. After one day, cells were treated with 20 μM HeSPs in the presence or the absence of 20 μM heme in fresh medium for 6 days. Medium was changed every 3 days. 6 days post treatment, apoptosis assay was performed according to manufacturer's protocol. Fluorescent images were captured using Biotek Cytation 5 plate reader.

Animals. NOD/SCID mice (IMSR Cat #CRL:394, RRID: IMSR_CRL:394) were purchased from Charles River Laboratories. Mice were bred and cared for in a University of Texas at Dallas specific pathogen-free animal facility in accordance with NIH guidelines. All animal procedures were conducted under protocols approved by Institutional Animal Care and Use Committee (IACUC) at the University of Texas at Dallas (UTD). Animals were regularly examined for any signs of stress and euthanized according to preset criteria.

Treatment of human NSCLC xenografts in NOD/SCID mice. To generate subcutaneous models, $2 \times 10^6$ H1299-Luc cells in serum-free medium containing 50% Matrigel were injected subcutaneously into the left flank region of 4-6 weeks old female NOD/SCID mice (n=6 per group). Mice were randomized into treatment groups that received saline (for control) and various HeSPs (I.V. 25 mg/kg every 3 days), respectively. Body masses were recorded once every week. When the tumors reached 1 cm$^3$ (after ~3 weeks of treatment), mice were euthanized by cervical dislocation. Tumors were resected and weighed. Tumor tissues were briefly homogenized and used for oxygen consumption rate and ATP assays.

For detecting the toxicity of HeSPs treatment on blood and liver functions, blood was obtained from mice via the sub-mandibular vein before sacrifice and was collected in blood collection tubes (BD microtainer tubes Cat #365963 and Cat #365974 from Fischer scientific). Serum samples were prepared and then used for determining hemoglobin levels with a hemoglobin assay kit from Sigma-Aldrich (Cat #294 MAK115-1KT) and ALT levels (alanine transaminase levels) with an ALT activity assay kit from Sigma-Aldrich (MAK052-1KT), respectively. Whole blood samples were used for counting red blood cells (RBCs) using a hemocytometer. No morphological differences were observed in red cells from treated and untreated mice.

In vivo bioluminescence imaging (BLI). Mice bearing lung tumor xenografts were imaged with an IVIS Lumina III In Vivo Imaging system (Perkin Elmer). Briefly, mice were anesthetized in the isoflurane chamber (2% isoflurane and oxygen), and luciferin (potassium salt; Perkin Elmer; 80 μl of 40 mg/ml) was administered subcutaneously between the scapulae. A BLI time course was acquired over 30 mins (Exposure time: auto, F Stop: 1.2, Binning: medium). The images were quantified using Living Image software version 4.5.2 (Perkin Elmer). Regions of interest (ROIs) were selected, and bioluminescence signals integrated. The total bioluminescent signals (photon/sec) from ROIs of mice were calculated as specified by the manufacturer's instructions.

Measurement of Oxygen Consumption and ATP Levels. Oxygen consumption was measured, as described previously[11]. To measure oxygen consumption rates and ATP levels from freshly isolated tumors, subcutaneous tumors were surgically resected from mice and cut into small pieces. Tumors were weighed and homogenized immediately using mechanical homogenizer to gain a homogenous cell suspension. Tissue debris was removed by gentle centrifugation. Cells were suspended in 400 ul of complete medium, and OCR was measured using a Clark-type electrode. ATP levels were measured with an ATP determination kit (Molecular probes). Liver cells were isolated and used to measure ATP levels in the same manner. All experiments were carried out in triplicate, and the background luminescence was subtracted from the measurement. ATP concentrations were calculated from the ATP standard curve and normalized with the numbers of cells used. Both Oxygen consumption rates and ATP levels were normalized with protein amounts.

Candida albicans strain, analyses of pathogenic functions, and measurement of heme uptake. *C. albicans* strain SC5314 was kindly provided by Dr. Andrew Y Koh (UT Southwestern Medical Center). *C. albicans* strain was grown overnight at 37° C. in yeast extract-peptone-glycerol (YPG) medium. For the measurement of heme uptake, a fluorescent analog of heme, zinc protoporphyrin IX (ZnPP, Frontier Scientific Inc.), was used. *C. albicans* strain was grown overnight at 37° C. in yeast extract-peptone-dextrose (YPD) medium, harvested by centrifugation, washed with PBS, and resuspended in PBS. Briefly, $10^6$ cells were incubated for 1 hour with 60 µmol/L ZnPP in the presence or the absence of 40 µmol/L HeSPs. Fluorescence intensity was measured with a Biotek Cytation 5 plate reader. Experiments were conducted in triplicates, and ZnPP uptake was normalized with total cell number.

For proliferation assays, the aforementioned overnight culture was inoculated in yeast nitrogen base (YNB)-glycerol medium or YNB-glycerol containing indicated concentrations of HeSPs. *C. albicans* cell proliferation was determined by measuring optical density at 600 nm. Data presented are averages of four replicates for the readings obtained at 96 hours. *C. albicans* biofilm formation was performed, as described previously[50]. Briefly, 100 µl of yeast suspension ($10^7$ cells/ml) in PBS was added in each well of a 96-well plate and the plate was incubated at 37° C. for 90 min for adhesion. Each well was washed twice with PBS to remove non-adherent cells. 200 µl of synthetic complete medium or synthetic complete medium containing HeSPs was added in each well and the plate was incubated at 37° C. in an orbital shaker at 75 rpm for 48 hours to form biofilm. Cells were then stained with 0.1% crystal violet for 20 minutes, and washed three times with water followed by quantification. Quantification was performed by dissolving crystal violet with 33% acetic acid. Absorbance was measured at 570 nm.

Results

Figure 8B:
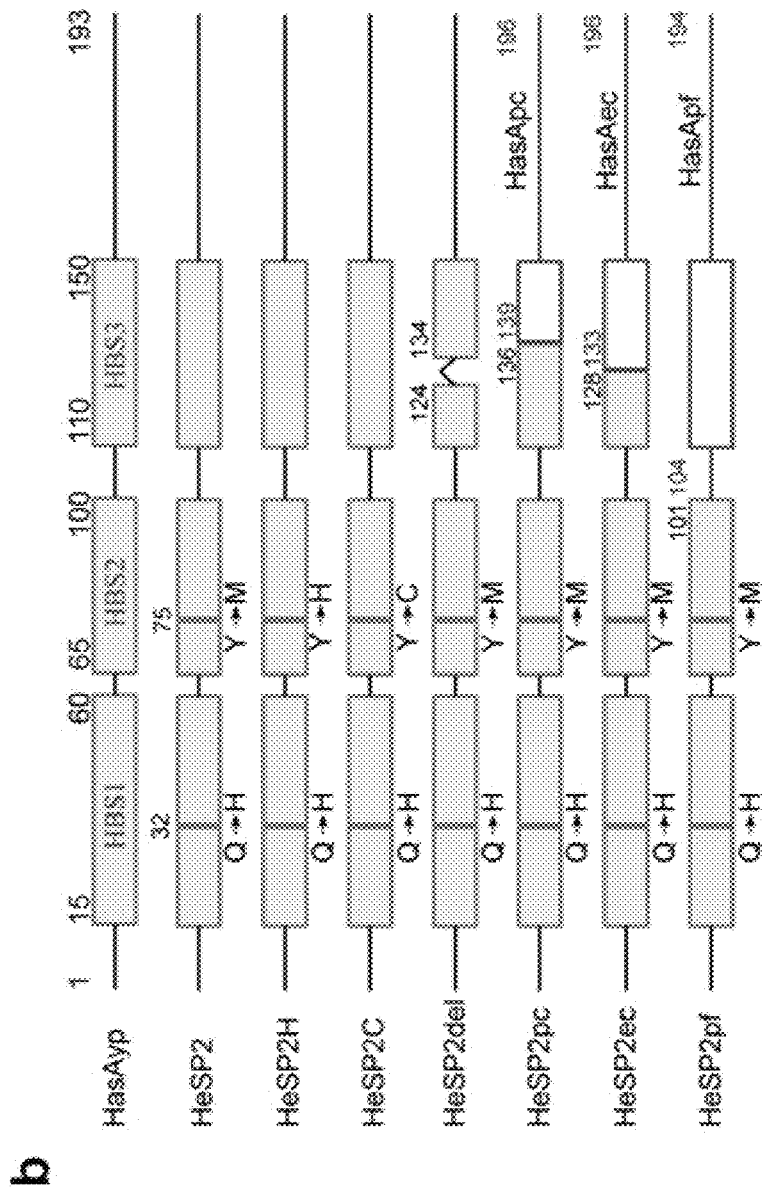
Figure 14:
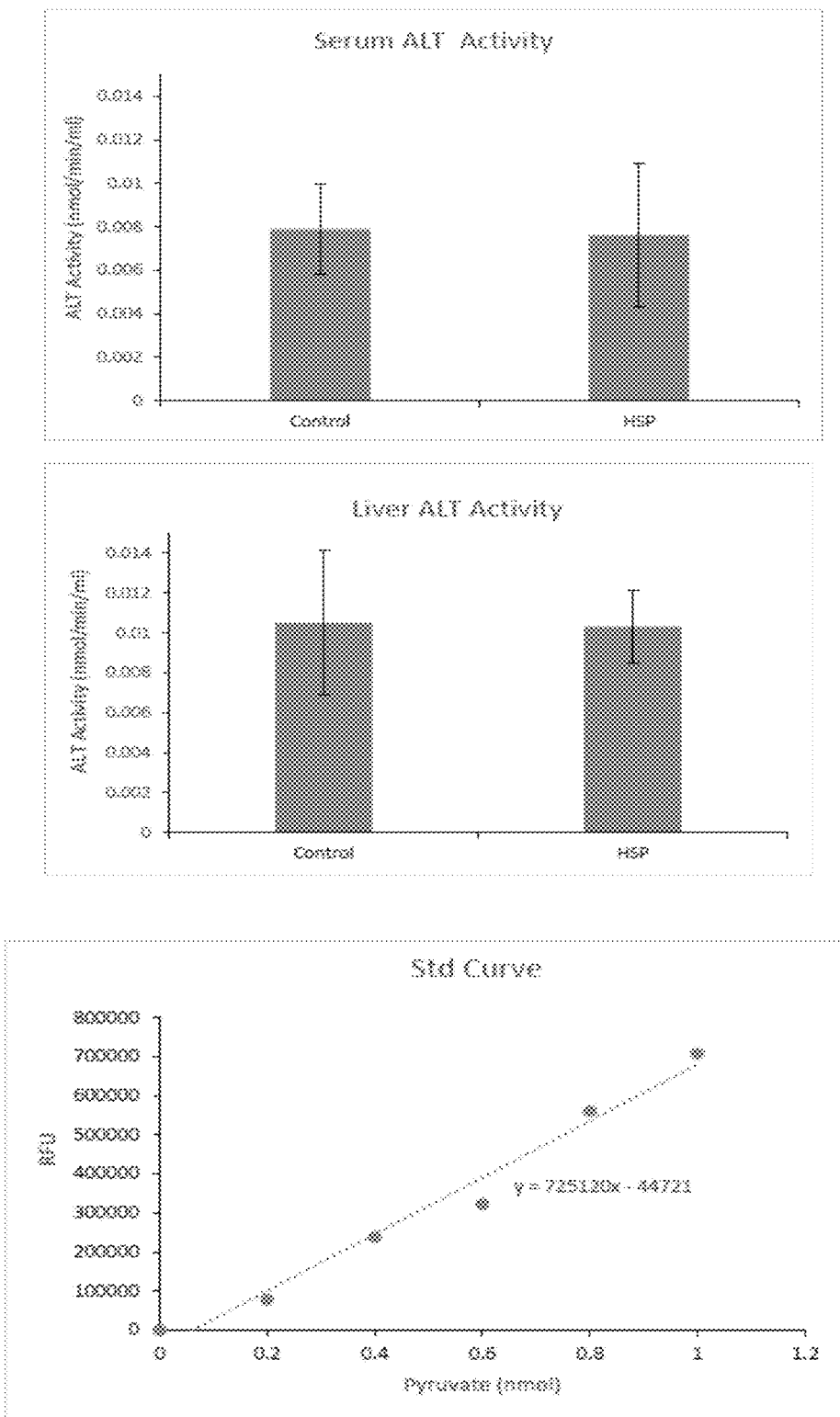
FIG. 14. Liver function test results form HSP2-treated mice. The lung cancer model, as described in the Examples, was generated by orthotopic implantation of H1299 tumor cells into NOD/SCID mice. The HSP2 peptide was administered at 25 mg/kg every three days for four weeks.

Design and biochemical characterization of heme-sequestering protein 2 (HeSP2). The hemophore HasA proteins are a family of highly conserved small proteins without homology to other known proteins (FIG. 8a)[29]. They are found in several bacteria, such as *Serratia marcescens, Yersinia pestis*, and *Pseudomonas fluorescens*. An initial test with purified HasA protein from *Yersinia pestis* showed that $HasA_{yp}$ exhibits some, but not statistically significant, anti-tumor activity (see FIGS. 23a-b). Because HasA's native function is not simply to sequester heme, the inventor reasoned that altered HasA proteins that retain heme-binding capabilities but with altered structural conformation may have better anti-tumor activity. She therefore made neutral changes in two key residues Q32 and Y75 that can directly contact heme, in the heme-binding pocket[30] (see HeSP2 in FIG. 8b). The Q32H change should not affect heme because H is the residue at that position in several HasA proteins (FIG. 8a). Additionally, the inventor made the Y75M change. Because both Y and M can chelate heme iron, this change should not affect heme binding. Indeed, she showed that HeSP2, like wild-type $HasA_{yp}$, bind to heme strongly using three previously established methods of detecting heme binding[31-33]. First, binding to heme agarose beads showed that HeSP2, like wild-type HasA, bound to heme strongly (FIG. 9a). Second, HeSP2 binding to heme shifted the peak of heme absorption Soret band from 385 nm to 408 nm (FIG. 9b). Third, size exclusion chromatography showed that heme eluted together with HeSP2, while heme per se was not eluted (FIG. 9c).

Next, the inventor examined the effects of the residue changes in HeSP2 on protein conformation by detecting protease sensitivity. As expected, heme did not considerably affect the sensitivity of β-amylase, which does not interact with heme (see FIG. 9a), to chymotrypsin (FIG. 10a). As shown in FIG. 10b, heme binding to wild-type $HasA_{yp}$ made it more resistant to chymotrypsin digestion, indicating altered conformation by heme binding. Interestingly, while the Q32H Y75M change in HeSP2 appeared to make HeSP2 more resistant to chymotrypsin, heme binding did not considerably alter the sensitivity of HeSP2 to chymotrypsin (FIG. 10c). Overall, the HeSP2-heme complex appeared to be more sensitive to chymotrypsin than the $HasA_{yp}$-heme complex (compare FIGS. 10b-c). These results suggest that the HeSP2-heme complex has a different conformation compared to the wild-type HasA-heme complex. Such a change in conformation may alter its anti-tumor property.

Further, the inventor directly showed that HeSP2 can effectively extract heme from hemoglobin. As shown in FIG. 10d, apo-HeSP2 and heme-bound HeSP2 migrated differently on a native gel (compare lanes 2 and 3 in FIG. 10d). The presence of heme was confirmed by using heme staining with TMB (N, N, N', N'-tetramethylbenzidine), as described[34]. When HeSP2 was mixed with hemoglobin, heme was transferred to HeSP2 (see lanes 4-7, FIG. 10d). The transfer of heme was instantaneous (see FIG. 24i a). Further, HeSP2 appeared to be more effective at extracting heme from hemoglobin than wild-type HasA (compare FIG. 9d with FIG. 24b).

Generation of additional HeSPs and their effects on lung cancer cells. To generate more HeSPs that may have anti-tumor activity, the inventor also changed Y75 to H and C, both of which can chelate heme, leading to two more HeSPs, HeSP2H and HeSP2C (see FIG. 8b). In addition, a loop region (residues 125-133) in $HasA_{yp}$ appears to be dispensable as shown in the structure of $HasA_{yp}$[30]. Thus, she deleted residues 125-133 to generate HeSP2del (FIG. 8b). Further, she generated three hybrid proteins with sequences from HasA proteins of *Yersinia pestis, Pseudomonas fluorescens, Erwinia carotovora*, and *Pectobacterium carotovorum*. Notably, the latter three are not pathogenic to humans[35] (see FIGS. 8a-b). HasA sequences from such bacteria may offer different pharmacological properties. The residues in the heme-binding pockets of HasA proteins are highly conserved (FIG. 8a). Thus, swapping and combining various regions of different HasA proteins may allow us to generate HeSPs with different immunogenic or pharmacological properties while they all retain high heme-sequestration capability. Thus, the inventor selected residue positions with turns (without beta sheet or alpha helix) as fusion points and generated three hybrid proteins, HeSP2ec, HeSP2pc, and HeSP2pf (FIG. 8b).

Figure 30:
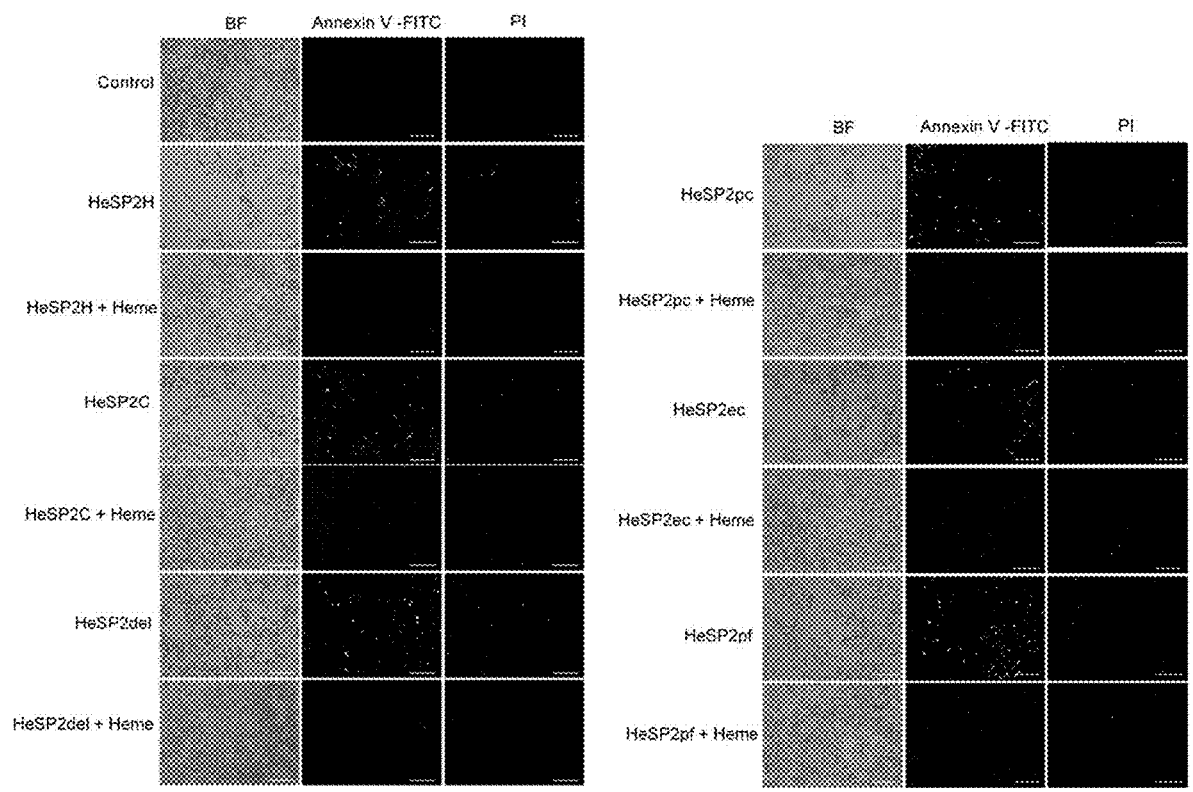
FIG. 30. HeSPs induces apoptosis in H1299 NSCLC cells, and addition of heme largely reverses the apoptosis. H1299 NSCLC cells were treated with 20 μM HeSPs in the presence or absence of 20 μM heme. Cells were subjected to apoptosis assay with Annexin V-FITC and Propidium Iodide (PI) staining. The images of cells were captured with bright field microscopy (BF) or fluorescent microscopy with a GFP or Texas Red (for PI) filters. Scale bar, 100 μm.

The inventor showed that all new HeSPs—HeSP2H, HeSP2C, HeSP2del, HeSP2ec, HeSP2pc, and HeSP2pf—bind to heme strongly, by examining heme agarose binding (FIG. 25), heme absorption spectrum (FIG. 26), and size exclusion chromatography (FIG. 27). All designed HeSPs significantly inhibited heme uptake in NSCLC cells (FIG. 28a). Importantly, all HeSPs inhibited NSCLC cell proliferation strongly, and addition of heme largely reversed the effect of HeSPs (FIG. 11a), indicating that the effects of HeSPs are attributable to heme sequestration. As expected, monitoring of HeSP2 incubated with NSCLC cells showed that HeSP2 remained stable in the medium even after prolonged incubation (FIG. 28b). The dose responses of NSCLC cell proliferation to HeSP treatments are shown in FIGS. 29a-g. Notably, as shown in FIG. 11b, treatment with HeSP2 caused apoptosis in NSCLC cells. Addition of heme reversed apoptosis, indicating that apoptosis is attributable to heme sequestration. Other HeSPs also caused apoptosis in NSCLC cells, and addition of heme reversed apoptosis (FIG. 30). These results show that HeSPs can effectively inhibit heme uptake, suppress cancer cell proliferation, and induce apoptosis in NSCLC cells.

HeSPs effectively suppress NSCLC tumor growth in mice and diminish oxygen consumption and ATP generation in tumors. The inventor directly examined the effectiveness of HeSPs to suppress tumor growth in vivo. To this end, she used subcutaneously implanted human NSCLC xenografts in NOD/SCID mice (FIG. 27). Data in FIGS. 12a-b show that all HeSPs significantly suppressed tumor growth, with the effect of HeSP2 being the strongest. The treatments of HeSPs did not cause significant changes in the whole-body masses of mice (FIG. 12c). The measurements of oxygen consumption rates (OCR) (FIG. 12d) and ATP levels (FIG. 12e) in isolated tumor cells from mice showed that all HeSPs substantially reduced OCR and ATP generation in tumors. Importantly, treatment with HeSPs did not significantly affect red cell counts (FIG. 31a) and hemoglobin levels (FIG. 31b) in the blood. Likewise, the treatments did not significantly affect liver function shown by alanine transaminase (ALT) activity (FIG. 31c). The treatments with HeSPs also did not significantly change ATP levels in liver cells isolated from mice (supplementary FIG. 31d).

HeSPs significantly inhibit the proliferation and biofilm formation in *Candida albicans*. In humans, >95% of the functional iron is in the form of heme, most of which is in hemoglobin molecules[36]. As such, pathogenic microbes have developed robust machineries to obtain iron from heme/hemoglobin[5, 6, 29]. *C. albicans* uses a heme assimilation system involving a conserved family of proteins, Rbt5, Rbt51/Pga10, Pga7, and Csa2[7, 37, 38]. These proteins are known to be important for *C. albicans* virulence[7, 38, 39]. Thus, the inventor tested whether HeSPs can influence *C. albicans* heme uptake, proliferation, and biofilm formation. As expected, HeSPs reduced heme uptake in *C. albicans* significantly (FIG. 32). As shown in FIG. 13a, HeSPs suppressed *C. albicans* proliferation significantly, and addition of heme largely reversed the effects of HeSPs, indicating that the suppression is attributable to heme sequestration. Likewise, HeSPs inhibited *C. albicans* biofilm formation significantly (FIG. 13b). Addition of heme considerably reversed the effects of HeSPs on biofilm formation, indicating that heme sequestration contributed to the suppression of biofilm formation (FIG. 13b). Together, these results suggest that heme sequestration can be a viable strategy to suppress the virulence of *C. albicans*.

Discussion

Heme has three major classes of functions in living organisms: (1) Heme serves as an essential iron source and metallonutrient for organisms ranging from pathogenic bacteria to humans[5, 10, 28, 29]. (2) Heme serves as a prosthetic group in proteins and enzymes involved in oxygen metabolism[20-22]. (3) Heme serves as a signaling molecule regulating diverse molecule and cellular processes including transcription, translation, and microRNA processing[14-17, 19]. To carry out these functions, heme needs to interact and bind, stably or transiently, to diverse cellular and extracellular proteins in living organisms. Thus, many studies have been carried out to characterize heme-protein interactions and design peptides and proteins that bind to heme stably or transiently[17, 40, 41]. In the past three decades, intense research has been carried out to design heme-binding proteins or maquettes, particularly those with four-helix bundle or β-sheet peptides[40-43]. However, these heme-binding proteins generally have heme-binding affinity in the nano to micro molar range[40, 41] much lower than HasA proteins[4]. These designed proteins would not be able to extract and sequester heme from heme proteins such as hemoglobin. While human hemopexin also binds to heme with pM affinity, heme-bound hemopexin can be internalized by human cells and utilized as an iron source[44]. Thus, hemopexin-like proteins would not be effective in sequestering heme from human tumor cells.

Here, the inventor shows that HeSP2 is very effective at extracting heme from hemoglobin (FIG. 10d). While previous experimental evidence suggested that wild-type HasA can extract heme from hemoglobin[45], the data shown in FIG. 24b (compare to FIG. 10d) suggest that wild-type HasA is less effective than HeSP2 in extracting heme from hemoglobin. The increased capability of HeSP2 to extract heme is likely attributable to the difference in protease sensitivity (indicative of protein conformation) induced by heme (FIGS. 10b-c). While heme binding to wild-type HasA$_{yp}$ caused a strong increase in the resistance of the protein to chymotrypsin (FIG. 10b), heme binding to HeSP2 did not considerably change the sensitivity of the protein to chymotrypsin (FIG. 10c). This suggests that HeSP2 may have adopted a conformation that can readily grip heme. The increased capability of HeSP2 to extract heme is also consistent with its potent anti-tumor activity (FIG. 12a) while wild-type HasA did not exhibit statistically significant anti-tumor activity (FIG. 15a-b). Two other variants of HeSP2, HeSP2H and HeSP2C (FIG. 8b), also exhibited significant anti-tumor activity and inhibited oxygen consumption and ATP generation in tumor cells (FIGS. 12a-b). Together, these results suggest that the heme binding pocket of HeSP2 likely represents an optimized structure for heme extraction and sequestration.

HeSP2del containing an internal deletion of a loop (residues 124-133) outside the HasA main structure[30] (FIG. 8b) was also stably expressed and exhibited strong activity in heme binding and inhibition of heme uptake (FIGS. 24-13a). HeSP2del exhibited significant anti-tumor activity and inhibited oxygen consumption and ATP generation in tumor cells (FIGS. 12a-e). However, shorter versions of HeSP2 with deletion of HasA residues at the C-terminus cannot be stably expressed, likely because these residues are part of the HasA compact structure, and their deletion destabilizes the overall structure. Nonetheless, these results suggest that HeSP2 variants with anti-tumor activity can be generated by making changes that do not disrupt the overall HasA protein structure. This idea is further tested by the generation of three hybrid HasA proteins: HeSP2pc, HeSP2ec, HeSP2pf (FIG. 8b). They exhibited strong activity in heme binding and inhibition of heme uptake (Supplementary FIGS. 10-13a), as well as significant anti-tumor activity (FIGS.

12a-b). These results show that functional HeSPs with strong anti-tumor activity but potentially different pharmacological properties can be generated by making hybrid HasA proteins.

It is worth noting that these engineered HeSPs can be applied for the treatment of other diseases relating to heme. Here, the inventor tested the effect of HeSPs on *C. albicans* because *C. albicans* uses heme as a nutrient[5, 6]. She found that HeSPs inhibited heme uptake (FIG. 32), cell proliferation (FIG. 13a), and biofilm formation (FIG. 13b) in *C. albicans*. Importantly, excess heme have been shown to increase the risks of cardiovascular diseases and diabetes[28]. Thus, this strategy of heme sequestration can potentially be applied to the treatment of these common diseases.

Importantly, HeSPs did not significantly affect blood and liver functions. Treatment with HeSPs in mice did not cause significant changes in RBC counts (FIG. 31a), hemoglobin levels (FIG. 31b), ALT (alanine aminotransferase) activity (FIG. 31c), or liver cell ATP levels (FIG. 31d). These results are consistent with previous studies showing that the inhibitor of heme synthesis, succinyl acetone, has low toxicity to animals[46]. Heme synthesis in erythroid and liver cells is very high[47]. Heme uptake is generally not needed for normal cells[11]. Notably, previous studies indicated that erythrocytes can provide heme for other cells and tissues[8, 48]. Thus, it is not surprising that heme sequestration by HeSPs did not cause erythroid and liver toxicity during the treatment periods in mice. Heme and iron are linked: heme synthesis requires iron, and heme degradation releases iron. However, likely due to their respective chemical properties, the main biological functions of heme iron and non-heme iron in living organisms may have become distinct. Due to its unique property for binding oxygen, the primary functions of heme iron are for oxygen utilization, metabolism, and detoxification, particularly in OXPHOS for ATP generation. Non-heme iron, however, often exists in proteins and enzymes as iron-sulfur cluster, and has essential functions in DNA replication, repair, and cell cycle[49]. Thus, both iron depletion and heme depletion can have anti-tumor effects, but the mechanisms largely differ[11]. Notably, suppression of tumor growth should also lower the demand for iron for tumor growth, thereby alleviating potential blood toxicity posed by HeSP treatment. Taken together, these results show that the strategy of heme sequestration and the use of HeSPs can be applied in the prevention and treatment of common diseases, including cancer and infection.

REFERENCES FOR EXAMPLE 2

1. Beutler, E., Bothwell, T. H., Charlton, R. W. & Motulsky, A. G. in The metabolic and molecular bases of inherited disease, Vol. 3. (eds. C. R. Scriver et al.) Chapter 127: 121-179 (The McGraw-Hill Companies, Inc., New York; 2009).
2. Oh, J. Y. et al. Absorbance and redox based approaches for measuring free heme and free hemoglobin in biological matrices. Redox Biol 9, 167-177 (2016).
3. Wandersman, C. & Delepelaire, P. Haemophore functions revisited. Mol Microbiol 85, 618-631 (2012).
4. Deniau, C. et al. Thermodynamics of heme binding to the HasA(SM) hemophore: effect of mutations at three key residues for heme uptake. Biochemistry 42, 10627-10633 (2003).
5. Bairwa, G., Jung, W. H. & Kronstad, J. W. Iron acquisition in fungal pathogens of humans. Metallomics 9, 215-227 (2017).
6. Roy, U. & Kornitzer, D. Heme-iron acquisition in fungi. Curr Opin Microbiol 52, 77-83 (2019).
7. Kuznets, G. et al. A relay network of extracellular heme-binding proteins drives *C. albicans* iron acquisition from hemoglobin. PLoS pathogens 10, e1004407 (2014).
8. Khan, A. A. & Quigley, J. G. Control of intracellular heme levels: heme transporters and heme oxygenases. Biochim Biophys Acta 1813, 668-682 (2011).
9. Chiabrando, D., Fiorito, V., Petrillo, S. & Tolosano, E. Unraveling the Role of Heme in Neurodegeneration. Front Neurosci 12, 712 (2018).
10. Reddi, A. R. & Hamza, I. Heme Mobilization in Animals: A Metallolipid's Journey. Acc Chem Res 49, 1104-1110 (2016).
11. Sohoni, S. et al. Elevated Heme Synthesis and Uptake Underpin Intensified Oxidative Metabolism and Tumorigenic Functions in Non-Small Cell Lung Cancer Cells. Cancer Res 79, 2511-2525 (2019).
12. Siegel, R. et al. Cancer treatment and survivorship statistics, 2012. CA Cancer J Clin 62, 220-241 (2012).
13. American-Cancer-Society (2019).
14. Barr, I. et al. Ferric, not ferrous, heme activates RNA-binding protein DGCR8 for primary microRNA processing. Proc Natl Acad Sci USA 109, 1919-1924 (2012).
15. Mense, S. M. & Zhang, L. Heme: a versatile signaling molecule controlling the activities of diverse regulators ranging from transcription factors to MAP kinases. Cell Res 16, 681-692 (2006).
16. Chen, J. J. & Zhang, S. Heme-regulated eIF2alpha kinase in erythropoiesis and hemoglobinopathies. Blood 134, 1697-1707 (2019).
17. Wissbrock, A., Paul George, A. A., Brewitz, H. H., Kuhl, T. & Imhof, D. The molecular basis of transient heme-protein interactions: analysis, concept and implementation. Biosci Rep 39 (2019).
18. Small, S. K., Puri, S. & O'Brian, M. R. Heme-dependent metalloregulation by the iron response regulator (Irr) protein in *Rhizobium* and other Alpha-proteobacteria. Biometals 22, 89-97 (2009).
19. Shimizu, T., Lengalova, A., Martinek, V. & Martinkova, M. Heme: emergent roles of heme in signal transduction, functional regulation and as catalytic centres. Chem Soc Rev 48, 5624-5657 (2019).
20. Ortiz de Montellano, P. R. in Wiley Encyclopedia of Chemical Biology, Vol. 2 240-249 (John Wiley & Sons, Ltd, West Sussex; 2009).
21. Kim, H. J., Khalimonchuk, O., Smith, P. M. & Winge, D. R. Structure, function, and assembly of heme centers in mitochondrial respiratory complexes. Biochim Biophys Acta 1823, 1604-1616 (2012).
22. Padmanaban, G., Venkateswar, V. & Rangarajan, P. N. Haem as a multifunctional regulator. Trends Biochem Sci 14, 492-496 (1989).
23. Farge, T. et al. Chemotherapy-Resistant Human Acute Myeloid Leukemia Cells Are Not Enriched for Leukemic Stem Cells but Require Oxidative Metabolism. Cancer Discov 7, 716-735 (2017).
24. Kuntz, E. M. et al. Targeting mitochondrial oxidative phosphorylation eradicates therapy-resistant chronic myeloid leukemia stem cells. Nat Med 23, 1234-1240 (2017).
25. Navarro, P. et al. Targeting Tumor Mitochondrial Metabolism Overcomes Resistance to Antiangiogenics. Cell Rep 15, 2705-2718 (2016).
26. Zhang, G. et al. Targeting mitochondrial biogenesis to overcome drug resistance to MAPK inhibitors. J Clin Invest 126, 1834-1856 (2016).

27. Lee, K. M. et al. MYC and MCL1 Cooperatively Promote Chemotherapy-Resistant Breast Cancer Stem Cells via Regulation of Mitochondrial Oxidative Phosphorylation. Cell Metab 26, 633-647 e637 (2017).
28. Hooda, J., Shah, A. & Zhang, L. Heme, an essential nutrient from dietary proteins, critically impacts diverse physiological and pathological processes. Nutrients 6, 1080-1102 (2014).
29. Huang, W. & Wilks, A. Extracellular Heme Uptake and the Challenge of Bacterial Cell Membranes. Annu Rev Biochem 86, 799-823 (2017).
30. Kumar, R. et al. The hemophore HasA from *Yersinia pestis* (HasAyp) coordinates hemin with a single residue, Tyr75, and with minimal conformational change. Biochemistry 52, 2705-2707 (2013).
31. Zhang, L. & Guarente, L. Heme binds to a short sequence that serves a regulatory function in diverse proteins. Embo J 14, 313-320 (1995).
32. Lal, S. et al. Heme promotes transcriptional and demethylase activities of Gis1, a member of the histone demethylase JMJD2/KDM4 family. Nucleic Acids Res 46, 215-228 (2018).
33. Kuhl, T. et al. Analysis of Fe(III) heme binding to cysteine-containing heme-regulatory motifs in proteins. ACS Chem Biol 8, 1785-1793 (2013).
34. Galmozzi, A. et al. PGRMC2 is an intracellular haem chaperone critical for adipocyte function. Nature 576, 138-142 (2019).
35. Scales, B. S., Dickson, R. P., LiPuma, J. J. & Huffnagle, G. B. Microbiology, genomics, and clinical significance of the *Pseudomonas fluorescens* species complex, an unappreciated colonizer of humans. Clin Microbiol Rev 27, 927-948 (2014).
36. Beutler, E., Bothwell, T. H., Charlton, R. W. & Motulsky, A. G. in The Online Metabolic and Molecular Bases of Inherited Disease. (eds. D. L. Valle et al.) (The McGraw-Hill Companies, Inc., New York, NY; 2014).
37. Weissman, Z. & Kornitzer, D. A family of *Candida* cell surface haem-binding proteins involved in haemin and haemoglobin-iron utilization. Mol Microbiol 53, 1209-1220 (2004).
38. Perez, A. et al. Biofilm formation by *Candida albicans* mutants for genes coding fungal proteins exhibiting the eight-cysteine-containing CFEM domain. FEMS yeast research 6, 1074-1084 (2006).
39. Okamoto-Shibayama, K., Kikuchi, Y., Kokubu, E., Sato, Y. & Ishihara, K. Csa2, a member of the Rbt5 protein family, is involved in the utilization of iron from human hemoglobin during *Candida albicans* hyphal growth. FEMS yeast research 14, 674-677 (2014).
40. Solomon, L. A., Kodali, G., Moser, C. C. & Dutton, P. L. Engineering the assembly of heme cofactors in man-made proteins. J Am Chem Soc 136, 3192-3199 (2014).
41. D'Souza, A., Wu, X., Yeow, E. K. L. & Bhattacharjya, S. Designed Heme-Cage beta-Sheet Miniproteins. Angew Chem Int Ed Engl 56, 5904-5908 (2017).
42. Gibney, B. R., Mulholland, S. E., Rabanal, F. & Dutton, P. L. Ferredoxin and ferredoxin-heme maquettes. Proc Natl Acad Sci USA 93, 15041-15046 (1996).
43. Rojas, N. R. et al. De novo heme proteins from designed combinatorial libraries. Protein Sci 6, 2512-2524 (1997).
44. Smith, A. & McCulloh, R. J. Hemopexin and haptoglobin: allies against heme toxicity from hemoglobin not contenders. Front Physiol 6, 187 (2015).
45. Letoffe, S., Nato, F., Goldberg, M. E. & Wandersman, C. Interactions of HasA, a bacterial haemophore, with haemoglobin and with its outer membrane receptor HasR. Mol Microbiol 33, 546-555 (1999).
46. Raff, R. F. et al. Pharmacologic, toxicologic, and marrow transplantation studies in dogs given succinyl acetone. Transplantation 54, 813-820 (1992).
47. Anderson, K. E., Sassa, S., Bishop, D. F. & Desnick, R. J. in The metabolic and molecular bases of inherited disease, Vol. 2. (eds. C. R. Scriver et al.) Chapter 124: 121-153 (The McGraw-Hill Companies, Inc., New York; 2009).
48. Dailey, H. A. & Meissner, P. N. Erythroid heme biosynthesis and its disorders. Cold Spring Harb Perspect Med 3, a011676 (2013).
49. Torti, S. V., Manz, D. H., Paul, B. T., Blanchette-Farra, N. & Torti, F. M. Iron and Cancer. Annu Rev Nutr 38, 97-125 (2018).
50. Jin, Y., Samaranayake, L. P., Samaranayake, Y. & Yip, H. K. Biofilm formation of *Candida albicans* is variably affected by saliva and dietary sugars. Arch Oral Biol 49, 789-798 (2004).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended claims. The specific embodiments provided herein are examples of useful embodiments of the present disclosure and it will be apparent to one skilled in the art that the present disclosure may be carried out using a large number of variations of the devices, device components, methods steps set forth in the present description. As will be recognized by one of skill in the art, methods and devices useful for the present methods can include a large number of optional composition and processing elements and steps.

What is claimed:

1. A method of treating small cell carcinoma comprising administering to said subject a recombinant heme sequestering peptide (HeSP) comprising an amino acid substitution of Q32H in the Q32 loop of *Yersinia pestis* HasA.

2. The method of claim 1, wherein said small cell carcinoma is recurrent.

3. The method of claim 1, further comprising treating said subject with another small cell carcinoma therapy selected from the group consisting of chemotherapy, radiotherapy, immunotherapy, toxin therapy, hormonal therapy, and surgery.

4. The method of claim 1, wherein said HeSP is administered local to a tumor site.

5. A method of treating cancer comprising administering to said subject (i) radiation, chemotherapy and/or immunotherapy and (ii) a recombinant heme sequestering peptide (HeSP) comprising an amino acid substitution of Q32H in the Q32 loop of *Yersinia pestis* HasA.

6. The method of claim 1, wherein the HeSP further comprises an amino acid substitution in a heme binding pocket at Y75.

7. The method of claim 1, wherein the HeSP has a single amino acid substitution of Q32H in the Q32 loop of *Yersinia pestis* HasA.

8. The method of claim 1, having only two amino acid substitutions-of Q32H and Y75M, Q32H and Y75H, or Q32H and Y75C.

9. The method of claim 1, wherein said HeSP has the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10.

10. The method of claim 1, wherein said HeSP is bound to zinc protoporphyrin.

11. The method of claim 5, wherein said cancer is lung cancer, colon cancer, head & neck cancer, brain cancer, liver cancer, pancreatic cancer, prostate cancer, ovarian cancer, testicular cancer, uterine cancer, breast cancer, skin cancer, lymphoma, or leukemia.

12. The method of claim 5, wherein said cancer is a recurrent cancer.

13. The method of claim 5, wherein said HeSP is administered local to a cancer site.

14. The method of claim 5, wherein the HeSP further comprises an amino acid substitution in a heme binding pocket at Y75.

15. The method of claim 5, wherein the HeSP has a single amino acid substitution of Q32H in the Q32 loop of *Yersinia pestis* HasA.

16. The method of claim 5, wherein the HeSP has only two amino acid substitutions, such as Q32H and Y75M, Q32H and Y75H, or Q32H and Y75C.

17. The method of claim 5, wherein said HeSP has the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10.

18. The method of claim 1, wherein said small cell carcinoma is drug resistant.

19. The method of claim 1, wherein said small cell carcinoma is primary.

20. The method of claim 1, wherein said small cell carcinoma is metastatic.

21. The method of claim 5, wherein said small cell carcinoma is drug resistant.

22. The method of claim 5, wherein said small cell carcinoma is primary.

23. The method of claim 5, wherein said small cell carcinoma is metastatic.

24. The method of claim 1, wherein said HeSP is administered regional to a tumor site.

25. The method of claim 1, wherein said HeSP is administered systemically.

26. The method of claim 5, wherein said HeSP is administered regional to a tumor site.

27. The method of claim 5, wherein said HeSP is administered systemically.

\* \* \* \* \*